(12) United States Patent
Manie et al.

(10) Patent No.: US 11,149,316 B2
(45) Date of Patent: *Oct. 19, 2021

(54) METHODS FOR DETECTING INACTIVATION OF THE HOMOLOGOUS RECOMBINATION PATHWAY (BRCA1/2) IN HUMAN TUMORS

(71) Applicants: INSTITUT CURIE, Paris (FR); INSERM (INSTITUT NATIONAL DE LA SANTE ET DE LA RECHERCHE MEDICALE), Pairs (FR)

(72) Inventors: Elodie Manie, Gentilly (FR); Marc-Henri Stern, Paris (FR); Tatiana Popova, La Varenne Saint Hilaire (FR)

(73) Assignees: Institut Curie, Paris (FR); INSERM (Institut National de la Sante et de la Recherche Medicale, Paris (FR)

( * ) Notice: Subject to any disclaimer, the term of this patent is extended or adjusted under 35 U.S.C. 154(b) by 194 days.

This patent is subject to a terminal disclaimer.

(21) Appl. No.: 15/039,699

(22) PCT Filed: Dec. 5, 2014

(86) PCT No.: PCT/EP2014/076786
§ 371 (c)(1),
(2) Date: May 26, 2016

(87) PCT Pub. No.: WO2015/086473
PCT Pub. Date: Jun. 18, 2015

(65) Prior Publication Data
US 2017/0260588 A1    Sep. 14, 2017

Related U.S. Application Data

(60) Provisional application No. 61/913,637, filed on Dec. 9, 2013.

(51) Int. Cl.
| | | |
|---|---|---|
| *C12Q 1/6886* | (2018.01) | |
| *C12Q 1/6827* | (2018.01) | |
| *A61K 33/243* | (2019.01) | |
| *A61K 31/131* | (2006.01) | |
| *A61K 31/166* | (2006.01) | |
| *A61K 31/196* | (2006.01) | |
| *A61K 31/282* | (2006.01) | |
| *A61K 31/454* | (2006.01) | |
| *A61K 31/496* | (2006.01) | |
| *A61K 31/502* | (2006.01) | |
| *A61K 31/5025* | (2006.01) | |
| *A61K 31/55* | (2006.01) | |

(52) U.S. Cl.
CPC ......... *C12Q 1/6886* (2013.01); *A61K 31/131* (2013.01); *A61K 31/166* (2013.01); *A61K 31/196* (2013.01); *A61K 31/282* (2013.01); *A61K 31/454* (2013.01); *A61K 31/496* (2013.01); *A61K 31/502* (2013.01); *A61K 31/5025* (2013.01); *A61K 31/55* (2013.01); *A61K 33/243* (2019.01); *C12Q 1/6827* (2013.01); *C12Q 2600/106* (2013.01); *C12Q 2600/112* (2013.01); *C12Q 2600/156* (2013.01)

(58) Field of Classification Search
None
See application file for complete search history.

(56) References Cited

U.S. PATENT DOCUMENTS

| | | |
|---|---|---|
| 3,590,028 A | 6/1971 | Arcamone et al. |
| 3,892,790 A | 7/1975 | Tobe et al. |
| 3,904,663 A | 9/1975 | Tobe et al. |
| 4,138,480 A | 2/1979 | Gosalvez |
| 4,946,954 A | 8/1990 | Talebian et al. |
| 4,950,738 A | 8/1990 | King et al. |
| 4,996,337 A | 2/1991 | Bitha et al. |
| 5,091,521 A | 2/1992 | Kolar et al. |
| 5,177,075 A | 1/1993 | Suto et al. |
| 5,295,944 A | 3/1994 | Teicher et al. |
| 5,434,256 A | 7/1995 | Khokhar et al. |
| 5,445,934 A | 8/1995 | Fodor et al. |
| 5,510,270 A | 4/1996 | Fodor et al. |
| 5,527,905 A | 6/1996 | Sugimura et al. |
| 5,539,083 A | 7/1996 | Cook et al. |
| 5,556,752 A | 9/1996 | Lockhart et al. |
| 5,578,832 A | 11/1996 | Trulson et al. |
| 5,633,016 A | 5/1997 | Johnson et al. |
| 5,633,243 A | 5/1997 | Sugimura et al. |
| 5,744,305 A | 4/1998 | Fodor et al. |
| RE36,397 E | 11/1999 | Zhang et al. |
| 6,040,138 A | 3/2000 | Lockhart et al. |

(Continued)

FOREIGN PATENT DOCUMENTS

| | | |
|---|---|---|
| EP | 0430402 | 6/1991 |
| EP | 1260520 | 11/2002 |
| EP | 2981624 | 2/2016 |
| JP | 2014-548965 | 10/2016 |
| JP | 2014-548965 | 8/2017 |
| JP | 6117194 | 10/2017 |
| JP | 2014-548965 | 11/2017 |
| KR | 100925337 | 11/2009 |
| WO | 1995020952 | 8/1995 |
| WO | 1998041531 | 9/1998 |

(Continued)

OTHER PUBLICATIONS

Ledermann et al (N engl J Med vol. 366 p. 1382 Apr. 12, 2012) (Year: 2012).*

(Continued)

*Primary Examiner* — Katherine D Salmon
(74) *Attorney, Agent, or Firm* — W&C IP

(57) ABSTRACT

The invention relates to methods for detecting inactivation of the DNA Homologous Recombination pathway in a patient, and in particular for detecting BRCA1 inactivation.

41 Claims, 12 Drawing Sheets

(56) References Cited

U.S. PATENT DOCUMENTS

| | | | |
|---|---|---|---|
| 6,087,340 | A | 7/2000 | Gatti et al. |
| 6,210,891 | B1 | 4/2001 | Nyren |
| 6,214,821 | B1 | 4/2001 | Daoud |
| 6,258,568 | B1 | 7/2001 | Nyren et al. |
| 6,274,320 | B1 | 8/2001 | Rothberg et al. |
| 6,403,563 | B1 | 6/2002 | Geroni et al. |
| 6,455,258 | B2 | 9/2002 | Bastian et al. |
| 6,465,177 | B1 | 10/2002 | Hoon et al. |
| 6,534,293 | B1 | 3/2003 | Barany et al. |
| 7,351,701 | B2 | 4/2008 | Helleday et al. |
| 7,485,707 | B2 | 2/2009 | Matvienko et al. |
| 7,732,491 | B2 | 6/2010 | Sherman et al. |
| 7,754,684 | B2 | 7/2010 | Stewart et al. |
| 7,759,488 | B2 | 7/2010 | Xiao et al. |
| 7,759,510 | B2 | 7/2010 | Kay et al. |
| 7,858,331 | B2 | 12/2010 | D'Andrea et al. |
| 7,868,040 | B2 | 1/2011 | Wilson et al. |
| 7,915,280 | B2 | 3/2011 | Ferraris et al. |
| 9,279,156 | B2 | 3/2016 | Gutin et al. |
| 9,574,229 | B2 | 2/2017 | Gutin et al. |
| 2003/0049613 | A1 | 3/2003 | Perucho et al. |
| 2005/0112604 | A1 | 5/2005 | Fujimoto et al. |
| 2006/0088870 | A1 | 4/2006 | Finkelstein et al. |
| 2007/0004621 | A1 | 1/2007 | Shridhar et al. |
| 2007/0070349 | A1 | 3/2007 | Harris et al. |
| 2008/0108057 | A1 | 5/2008 | Griffith et al. |
| 2009/0081237 | A1 | 3/2009 | D'Andrea et al. |
| 2009/0246789 | A1 | 10/2009 | Buckhaults et al. |
| 2010/0145894 | A1 | 6/2010 | Semizarov et al. |
| 2010/0159466 | A1 | 6/2010 | Eng et al. |
| 2012/0015050 | A1 | 1/2012 | Abkevich et al. |
| 2013/0281312 | A1 | 10/2013 | Richardson et al. |
| 2015/0080260 | A1 | 3/2015 | Abkevich et al. |

FOREIGN PATENT DOCUMENTS

| | | | |
|---|---|---|---|
| WO | 1999054498 | | 10/1999 |
| WO | 2000024933 | | 4/2000 |
| WO | 2003074723 | | 9/2003 |
| WO | 2004042032 | | 5/2004 |
| WO | 2004/075833 | A2 | 9/2004 |
| WO | 2006098978 | | 9/2006 |
| WO | 2006110855 | | 10/2006 |
| WO | 2006116341 | | 11/2006 |
| WO | 2006128195 | | 11/2006 |
| WO | 2007035893 | | 3/2007 |
| WO | 2009033178 | | 3/2009 |
| WO | 2009073869 | | 6/2009 |
| WO | 2009148528 | | 12/2009 |
| WO | 2010051318 | | 5/2010 |
| WO | 2011048495 | | 4/2011 |
| WO | 2011106541 | | 9/2011 |
| WO | 2011160063 | | 12/2011 |
| WO | 2012019000 | | 2/2012 |
| WO | 2012027224 | | 3/2012 |
| WO | 2012/092426 | A1 | 7/2012 |
| WO | 2013/096843 | A1 | 6/2013 |
| WO | 2013130347 | | 9/2013 |
| WO | 2013/182645 | | 12/2013 |
| WO | 2014/165785 | A2 | 10/2014 |
| WO | 2015/086473 | A1 | 6/2015 |
| WO | 2015/108986 | A1 | 7/2015 |

OTHER PUBLICATIONS

Garcia-Marco (Blood 1996 vol. 88 p. 1568) (Year: 1996).*
Extended European Search Report, from Application EP12860530.0, dated Jul. 24, 2015.
Fang et al. "Genomic Differences Between Estrogen Receptor (ER)-Positive and ER-Negative Human Breast Carcinoma Identified by Single Nucleotide Polymorphism Array Comparative Genome Hybridization Analysis", Cancer, vol. 117, No. 10, May 2011, pp. 2024-2034.
Farmer et al; Targeting DNA repair defect in BRCA mutant cells as a therapeutic strategy; Nature; 2005; 434(7035):917-921.
Feltmate C M et al.: "Whole-genome allelotyping identified distinct loss-of-heterozygosity patterns in mucinous ovarian and appendiceal carcinomas", Clinical Cancer Research, vol. 11, No. 21, Nov. 1, 2005 (Nov. 1, 2005), pp. 7651-7657.
Ferreira et al: "Array CGH and gene-expression profiling reveals distinct genomic instability patterns associated with DNA repair and cell-cycle checkpoint pathways in Ewing's sarcoma", Oncogene, vol. 27, No. 14, Mar. 27, 2008 (Mar. 27, 2008), pp. 2084-2090.
Filopanti et al., "Loss of heterozygosity at the SS receptor type 5 locus in human GH- and TSH-secreting pituitary adenomas," J. Endocrinol. Invest., Nov. 2004, vol. 27, No. 10, pp. 937-942.
Fontanillas et al., "Key considerations for measuring allelic expression on a genomic scale using high-throughput sequencing", Molecular Ecology, vol. 19, No. 1, Mar. 1, 2010, pp. 212-227.
Franko, J. et al., "Loss of heterozygosity predicts poor survival after resection of pancreatic adenocarcinoma," J. Gastrointest. Surg., Oct. 2008, vol. 12, No. 10, pp. 1664-1723.
Friedenson; BRCA1 and BRCA2 pathways and the risk of cancers other than breast or ovarian; MedGenMed; 2005; 7(2):60, 25 pages.
Gelmon et al; Olaparib in patients with recurrent high-grade serous or poorly differentiated ovarian carcinoma or triple-negative breast cancer: a phase 2, multicentre, open-label, non-randomised study; Lancet Oncol; 2011;12(9):852-861.
Goransson et al. "Quantification of Normal Cell Fraction and Copy Number Neutral LOH in Clinical Lung Cancer Samples Using SNP Array Data", PLOS One, vol. 4, No. 6, Jun. 26, 2009 (Jun. 26, 2009), p. e6057.
Gorringe et al. "Are there any more ovarian tumor suppressor genes? A new perspective using ultra high-resolution copy number and loss of heterozygosity analysis", Genes Chromosomes & Cancer, John Wiley & Sons, Inc, US, vol. 48, No. 10, Oct. 1, 2009 (Oct. 1, 2009), pp. 931-942.
Graziani et al. "PARP-1 inhibition to treat cancer, ischemia, inflammation", Pharmacological Research, Academic Press, London, GB, vol. 52, No. 1, Jul. 1, 2005 (Jul. 1, 2005), pp. 1-4.
Gudmundsdottir et al. "The roles of BRCA1 and BRCA2 and associated proteins in the maintenance of genomic stability", Oncogene, vol. 25, No. 43, Sep. 25, 2006 (Sep. 25, 2006), pp. 5864-5874.
Gunnarsson et al. "Large but not small copy-number alterations correlate to high-risk genomic aberrations and survival in chronic lymphocytic lukemia: a high-resolution genomic screening of newly diagnosed patients", Lukemia, vol. 24, No. 1, Jan. 1, 2010 (Jan. 1, 2010), pp. 211-215.
Hampton et al., "Simultaneous assessment of loss of heterozygosity at multiple microsatellite loci using semi-automated fluorescence-based detection: Subregional mapping of chromosome 4 in cervical carcinoma," PNAS, Jun. 1996, vol. 93, No. 13, pp. 6704-6709.
Hastings et al., Nat Rev. Genetic 10(8): 551-564 (2009). "Mechanisms of change in gene copy number."
Hastings et al., PLOS Genetics 5(1):e1000327 (2009). "A microhomology-mediated break-induced replication model for the origin of human copy number variation.", pp. 1-9.
Heap et al., "Genome-wide analysis of allelic expression imbalance in human primary cells by high-throughput transcriptome resequencing", Human Molecular Genetics, vol. 19, No. 1, Jan. 1, 2010, pp. 122-134.
Heinsohn, S. et al., "Determination of the prognostic value of loss of heterzygosity at the retinoblastoma gene in osteosarcoma," Int. J. Oncol., May 2007, vol. 30, No. 5, pp. 1205-1214.
Heiser et al., Proc Natl Aced Sci U S A. 109(8):2724-9 (2012). "Subtype and pathway specific responses to anticancer compounds in breast cancer."
Hendricks et al. "'Recombomice': The past, present, and future of recombination-detection in mice" DNA Repair, vol. 3, No. 10, Oct. 5, 2004, pp. 1255-1261.
Hennessy et al; Somatic mutations in BRCA 1 and BRCA2 could expand the No. Of patients that benefit from poly(ADP ribose) polymerase inhibitors in ovarian cancer; J Clin Oncol; 2010; 28(22):3570-3576.

(56) References Cited

OTHER PUBLICATIONS

Holstege et al; BRCA1-mutated and basal-like breast cancers have similar aCGH profiles and a high incidence of protein truncating TP53 mutations; BMC Cancer; 2010; 10:654, 15 pages.
Iafrate et al., Nat Genet. 36(9): 949-51. (2004). "Detection of large-scale variation in the human genome."
International Preliminary Report on Patentability, app. No. PCT/US2012/071380, dated Apr. 12, 2013.
International Search Report, for application PCT/EP2013/061707, dated Jul. 29, 2013.
International Search Report, for application PCT/US2011/026098, dated Nov. 25, 2011.
International Search Report, for application PCT/US2011/040953, dated Feb. 27, 2012.
International Search Report, for application PCT/US2011/048427, dated Nov. 7, 2011.
International Search Report, for application PCT/US2012/042668, dated Feb. 1, 2013.
International Search Report, for application PCT/US2012/071380, dated Apr. 12, 2013.
International Search Report, for application PCT/US2013/027295, dated Jun. 10, 2011.
International Search Report, for application PCT/US2015/045561, dated Nov. 9, 2015.
Isakoff et al., "TBCRC009: A Multicenter Phase II Clinical Trial of Platinum Monotherapy With Biomarker Assessment in Metastatic Triple-Negative Breast Cancer," J Clin Oncol, 2015, 1-8.
Janne et al. "High-resolution single-nucleotide polymorphism array and clustering analysis of loss of heterozygosity in human lung cancer cell lines", Oncogene, vol. 23, No. 15, Mar. 29, 2004 (Mar. 29, 2004), pp. 2716-2726.
Japanese Patent Application Kohyo Publication No. (JP-A) 2008-538496 (unexamined Japanese national phase publication corresponding to a non-Japanese international publication).
Johansson, P. et al., "Abstract 4833: A genomic portrait of tumor progression using next-generation sequencing", Cancer Res., Apr. 15, 2011, vol. 71, p. 4833.
Joosse et al. "Prediction of BRCA-1-association in hereditary non-BRCA1/2 breast carcinomas with array-CGH", Breast Cancer Research and Treatment, Kluwer Academic Publishers, BO, vol. 116, No. 3, Aug. 14, 2008 (Aug. 14, 2008), pp. 479-489.
Juul et al., Cancer Research, 69(24): 509S-510S (2009). "A Genomic Profile Derived Summary Measure of Chromosomal Breakpoints Predicts Response to Treatment with the DNA-Damaging Agent Cisplatin."
Kaklamani et al., "Phase II neoadjuvant clinical trial of carboplatin and eribulin in women with triple negative early-stage breast cancer (NCT01372579)," Breast Cancer Res Treat, 2015, 151:629-638.
Kalb et al., Genome Dyn. 1:218-42. (2006). "Fanconi anemia: causes and consequences of genetic instability."
Kerangueven, F. et al. Cancer Research 57, 5469-5475 (1997).
Ko et al., "Frequent loss of heterozygosity on multiple chromosomes in Chinese esophageal squamous cell carcinomas" Cancer Letters, vol. 170, No. 2, pp. 131-138 (2001).
Kolomietz et al., Genes Chromosomes Cancer. 35(2):97-112 (2002). "The role of Alu repeat clusters as mediators of recurrent chromosomal aberrations in tumors."
Kujawski et al. "Genomic complexity identifies patients with aggressive chronic lymphocytic lukemia", Blood, vol. 112, No. 5, Sep. 1, 2008 (Sep. 1, 2008), pp. 1993-2003.
Lakhani et al., Clin Cancer Res. 11(14)5175-80 (2005). "Prediction of BRCA1 status in patients with breast cancer using estrogen receptor and basal phenotype."
Lemeta et al., "Loss of Heterozygosity at 6q is Frequent and Concurrent with 3p Loss in Sporadic and Familial Capillary Hemangioblastomas," J. Neuropathol. Exp. Neurol., Oct. 2004, vol. 63, No. 10, pp. 1072-1079.
Leunen et al. "Recurrent Copy number alterations in BRCA1-mutated ovarian tumors alter biological pathways", Human Mutation, vol. 30, n. 12, Dec. 1, 2009 (Dec. 1, 2009), pp. 1693-1702.

Li C. et al. BMC Bioinformatics 2008, 9:204, pp. 1-16.
European Communication Response from Application No. 12801070.9, dated Apr. 20, 2017.
European Communication Response from Application No. 14779403.6, dated May 8, 2017.
Hansen et al., "Clinical significance of homologous recombination deficiency score testing in endometrial cancer patients", 2016, ASCO presentation.
Lheureux et al., American Association for Cancer Research, 2017, pp. 1-38.
Mills et al., Homologous Recombination Deficiency (HRD) Score Shows Superior Association with Outcome Compared to its Individual Score Components (LOH, TAI, and LST Scores) in Platinum Treated Serous Ovarian Cancer, Annual Meeting on Women's Cancer, 2016, pp. 1-19.
Shanda et al., "Homologous Recombination Deficiency (HRD) in Patients with Pancreatic Cancer and Response to Chemotherapy", 2017, ASCO presentation.
Timms et al., "DNA repair deficiencies in ovarian cancer: Genomic analysis of high grade serous ovarian tumors from the NOVA Study", 2015, ESMO presentation.
Timms et al., "The Molecular Landscape of Genome Instability in Prostate Cancer", 2016, ESMO presentation.
Timms et al., Breast Cancer Research, 2014, vol. 16, No. 475, pp. 1-9.
Timms, Declaration Under 37 C.F.R. § 1.132, 2016, pp. 1-3.
Japanese Office Action Response from Application No. 2014-548965, dated Apr. 27, 2017.
Stankiewicz et al., Am J Hum Genet. 72(5):1101-16 (2003). "Genome architecture catalyzes nonrecurrent chromosomal rearrangements."
Stefansson et al; Genomic profiling of breast tumours in relation to BRCA abnormalities and phenotypes; Breast Cancer Res; 2009; 11(4):R47, 14 pages.
Swisher et al. Cancer Res. 68(8):2581-6 (2008). "Secondary BRCA1 mutations in BRCA1-mutated ovarian carcinomas with platinum resistance."
Tai et al., "High-Throughput Loss-of-Heterozygosity Study of Chromosome 3p in Lung Cancer Using Single-Nucleotide Polymorphism Markers", Cancer Research, vol. 66, No. 8, Apr. 15, 2006, pp. 4133-4138.
Takahashi, Clinical Cancer Research, 13(1): 111-120 (2007). "Clonal and Parallel Evolution of Primary Lung Cancers and Their Metastases Revealed by Molecular Dissection of Cancer Cells."
Tan et al; 'BRCAness' syndrome in ovarian cancer: a case-control study describing the clinical features and outcome of patients with epithelial ovarian cancer associated with BRCA1 and BRCA2 mutations; J Clin Oncol; 2008;26(34):5530-5536.
Tassone et al., Br J Cancer. 88(8): 1285-91 (2003). "BRCA1 expression modulates chemosensitivity of BRCA1-defective HCC1937 human breast cancer cells."
Teh M-T et al.: "Genomewide Single Nucleotide Polymorphism Microarray Mapping in Basal Cell Carcinomas Unveils Uniparental Disomy as a Key Somatic Event", Cancer Research, vol. 65, No. 19, Oct. 1, 2005 (Oct. 1, 2005), pp. 8597-8603.
Telli et al., "Phase II Study of Gemcitabine, Carboplatin, and Iniparib as Neoadjuvan Therapy for Triple-Negative and BRCA1/2 Mutation-Associated Breast Cancer With Assessment of a Tumor-Based Measure of Genomic Instability: PrECOG0105," J Clin Oncol, 2015, 1-7.
The Cancer Genome Atlas Research Network; Integrated genomic analyses of ovarian carcinoma; Nature; 2011; 474(7353):609-615.
Tseng, R. C. et al., Genomewide loss of heterozygosity and its clinical associations in non-small cell lung cancer, Int. J. Cancer, Nov. 1, 2005, vol. 117, No. 2, pp. 241-247.
Tuna, M. et al. PLoS One 5(11):e15094 (Nov. 30, 2010).
Turner et al., Oncogene 26:2126-2132 (2007). "BRCA1 dysfunction in sporadic basal-like breast cancer."
Valeri A et al.: "High frequency of allelic losses in high-grade prostate cancer is associated with biochemical progression after radical prostatctomy", Urologic Oncology, Elsevier, New York, NY, US, vol. 23, No. 2, Mar. 1, 2005 (Mar. 1, 2005), pp. 87-92.
Van Loo et al., PNAS 107(39):16910-16915 (2010). "Allele-specific copy number analysis of tumors."

(56) References Cited

OTHER PUBLICATIONS

Volchenboum et al. "Comparison of Primary Neuroblastoma Tumors and Derivative Early-Passage Cell Lines Using Genome-Wide Single Nucleotide Polymorphism Array Analysis", Cancer Research, vol. 69, No. 10, May 12, 2009, pp. 4143-4149.
Vollenbergh et al. "Genomic instability in breast and ovarian cancers: translation into clinical predictive biomarkers", CMLS Cellular and Molecular Life Science, Birkhauser-Verlag, BA, vol. 69, No. 2, Sep. 16, 2011 (Sep. 16, 2011), pp. 223-245.
Vrieling et al., Nature Genetics 28:101-102 (2001). "Mitotic maneuvers in the light."
Walsh, C.S. et al. Clin Cancer Res 14(23):7645 (Dec. 1, 2008).
Wang et al., Cancer Research 64:64-71 (2004). "Loss of heterozygosity and it's correlation with expression in profiles in subclasses of invasive breast cancers."
Wang et al., Genome Biology 8R246 (2007). "Analysis of molecular inversion probe performance for allele copy number determination."
Wilcox et al; High-resolution methylation analysis of the BRCA1 promoter in ovarian tumors; Cancer Genet Cytogenet; 2005; 159(2): 114-122.
Wilcoxen et al., "Homologous recombination deficiency (HRD) score enriches for niraparib sensitive high grade ovarian tumors," Supplemental Abstract, 2015, 1 page.
Wilcoxen et al., "Use of homologous recombination deficiency (HRD) score to enrich for niraparib sensitive high grade ovarian tumors," J Clin Oncol, 2015, Supplemental Abstract: 5532, 2 pages.
Xiao et al., "The XIST Noncoding RNA Functions Independently of BRCA1 in X Inactivation," Cell, Mar. 2007, 128:977-989.
Xu et al., Molecular Cell 3:389-395 (1999). "Centrosome amplification and a defective G2-M cell cycle checkpoint induce genetic instability in BRCA1 Exon 11 Isoform-deficient cells."
Yang et al., Cancer Research 61:348-354 (2001). "Reconstitution of caspase 3 sensitizes MCF-7 Breast Cancer to Doxoubicin- and Etoposide-induced apoptsis."
Yaris N. et al. The Turkish Journal of Pediatrics 2004; 46: 182-185.
Zhao Q. et al., "Systematic detection of putative tumor suppressor genes through the combined use of exome and transcriptome sequencing", Genome Biol., 2010, vol. 11: R114, pp. 1-14.
Anonymous: "Myriad's HRD Test Significantly Predicts Response to Cisplatin Treatment in Patients with Triple Negative Breast Cancer in Second Research Study", Myriad, Dec. 2013.
European Communication Response, for application 15189527.3, dated Sep. 30, 2016.
European Communication, for application 128060530.0, dated Nov. 28, 2016.
Extended European Search Report, from Application EP14779403.6, dated Oct. 28, 2016.
Extended European Search Report, from Application EP16166825.6, dated Nov. 11, 2016.
Telli et al: "Abstract PD09-04: Homologous Recombination Deficiency (HRD) score predicts pathologic response following neoadjuvant platinum-based therapy in triple-negative and BRCA1/2 mutation-associated breast cancer (BC)", Cancer Research, Dec. 2012.
International Search Report and Written Opinion for International Patent Application No. PCT/EP2014/076786, dated Feb. 27, 2015.
Popova et al., "Ploidy and large-scale genomic instability consistently identify basal-like breast carcinomas with BRCA1/2 inactivation." Cancer Research, Aug. 29, 2012, XP055039519.
Abkevich et al., "Patterns of Genomic loss of heterozygosity predict homologous recombination repair defects in epithelial ovarian cancer." British Journal of Cancer, vol. 107, No. 10, Nov. 6, 2012. XP055085758.
Maxwell: Peter Maxwell and Associates, Aug. 9, 2017.
Bernardini et al: "The use of cytogenetics in understanding ovarian cancer", Biomedicine & Pharmacotherapy, vol. 58, p. 17-23, 2004.
Birbak et al: "Telomeric Allelic Imbalance Indicates Defective DNA Repair and Sensitivity to DNA-Damaging Agents", American Association for Cancer Research, Cancer Discovery, p. 366-375, Apr. 2012.
Campball et al: "A genetic variant that disrupts MET transcription is associated with autism", PNAS, vol. 103, No. 45, p. 16834-16839.
Karwatsky: Examination Search Report, CIPO, dated Jun. 6, 2017.
Courage: National Phase Application, Response, Bereskin & Parr, Aug. 22, 2017.
Duncavage et al: "Hybrid Capture and Next-Generation Sequencing Identify Viral Integration Sites from Formalin-Fixed Paraffin-Embedded Tissue", NGS Viral Insertion Site Discovery, the Journal of Molecular Diagnositcs, vol. 13, No. 3, p. 325-333, May 2011.
Helliot: Registered Letter, European Patent Office, Aug. 25, 2017.
Ripaud: Registered Letter, European Patent Office, Aug. 31, 2017.
Botz: Registered Letter, European Patent Office, Sep. 6, 2017.
Aslund: Registered Letter, European Patent Office, Nov. 23, 2017.
Gibson: Claim Amendments, European Patent Office, Sagittarius IP, Jan. 10, 2018.
Cho: PCT Papers, PCT, Jun. 7, 2017.
Johansson et al: "Targeted resequencing of candidate genes using selector probes", Nucleic Acids Research, vol. 39, No. 2, p. 1-13, 2011.
Juul et al: "Amount of Allelic Imbalance Predicts REsponse to the Cisplatin in Breast and Ovarian Cancer", Annals of Oncology, vol. 21, supplement 4, May 2010.
Kamat et al: "Chemotherapy induced microsatellite instability and loss of heterozygosity in chromosomes 2, 5, 10, and 17 in solid tumor patients", Cancer Cell International, vol. 14, No. 118, p. 1-9, 2014.
Kiialainen et al: "Performance of Microarray and Liquid Based Capture Methods for Target Enrichment for Massively Parallel Sequencing and SNP Discovery", PLOS One, vol. 6, issue 2, p. 1-10, Feb. 2011.
Kudoh et al: "Gains of 1q21-q22 and 13q12-q14 are Potential Indicators for Resistance to Cisplatin-based Chemotherapy in Ovarian Cancer Patients", American Association for Cancer, Clinical Cancer Research, vol. 5, p. 2526-2531, Sep. 1999.
Ledermann et al: "Olaparib Maintenance Therapy in PLatinum-Sensitive Relapsed Ovarian Cancer", The New England Jouranl of Medicine, vol. 366, No. 15, p. 1382-1392, Apr. 12, 2012.
Ross et al: "Comprehensive next-generation sequencing for clinically actionable mutations from formalin-fixed cancer tissues", Journal of Clinical Oncology, vol. 29, No. 15, p. 10564, May 2011.
Schweiger et al: "Genome-Wide Massively Parallel Sequencing of Formaldehyde Fixed-Paraffin Embedded (FFPE) Tumor Tissues for Copy-Number- and Mutation-Analysis", PLOS One, vol. 4, issue 5, May 2009.
Tommasi et al: "655Val and 1170Pro ERBB2 SNPs in familial breast cancer risk and BRCA1 alterations", Cellular Oncology, vol. 29, p. 241-248, 2007.
Varley et al: "Nested Patch PCR enables highly multiplexed mutation discovery in candidate genes", Cold Spring Harbor Laboratoy Press, Genome Research, vol. 18, p. 1844-1850, 2008.
Zuchner et al: "Linkage and association study of late-onset Alzheimer disease families linked to 9p21.3", National Institutes of Health, p. 1-12, Nov. 2008.
Li et al., BMC Bioinformatics 12:474 (2011). "Jetset: selecting the optimal microarray probe set to represent a gene."
Li et al., Nature Medicine 15(2):214-219 (2010). "Amplification of LAPTM4B and YWHAZ contributes to chemotherapy resistance and recurrence of breast cancer."
Lin et al. "Integrated analysis of copy number alterations and loss of heterozygosity in human pancreatic cancer using a high-resolution, single nucleotide polymorphism array", Oncology, vol. 75, No. 1-2, Sep. 1, 2008, pp. 102-112.
Loveday et al; Germline mutations in RAD51D confer susceptibility to ovarian cancer; Nat Genet; 2011; 43(9):879-882.
Luo et al., Nat Genet. 26(4):424-9 (2000). "Cancer predisposition caused by elevated mitotic recombination in Bloom mice."
Maeck et al. "Genetics instability in myelodysplastic syndrome: Detection of microsatellite instability and loss of heterozygosity in bone marrow samples with karyotype alterations" British Journal of Haematology, vol. 109, No. 4, Jun. 2000, pp. 842-846.

(56) References Cited

OTHER PUBLICATIONS

Marsit et al; Inactivation of the Fanconi anemia/BRCA pathway in lung and oral cancers: implications for treatment and survival; Oncogene; 2004; 23(4):1000-1004.
Mateo et al., "Appraising iniparib, the PARP inhibitor that never was—what must we learn?," Nature, Dec. 2013, 10: 688-696.
Matsumoto et al., "Allelic imbalance at 1P36 may predict prognosis of chemoradiation therapy for bladder preservation in patients with invasive bladder cancer", British Journal of Cancer, vol. 91, No. 6, pp. 1025-1031 (2004).
McVean et al., Philos Trans R Soc Lond B Biol Sci. 365(1544):1213-8 (2010). "What drived recombination hotspots to repeat DNA in humans?".
Meadows et al. "Genome-wide analysis of loss of heterozygosity and copy number amplification in uterine leiomyomas using the 100K single nucleotide polymorphism array", Experimental and Molecular Pathology, vol. 91, No. 1, Apr. 8, 2011 (Apr. 8, 2011), pp. 434-439.
Medri, L. et al. modern Pathology 2003;16(11):1067-1075.
Meindl et al; Germline mutations in breast and ovarian cancer pedigrees establish RAD51C as a human cancer susceptibility gene; Nat Genet; 2010; 42(5):410-414.
Mendes-Pereira et al; Synthetic lethal targeting of PTEN mutant cells with PARP inhibitors; EMBO Mol Med; 2009;1(6-7): 315-322.
Mukhopadhyay et al., "Clinicopathological Features of Homologous Recombination-Deficient Epithelial Ovarian Cancers: Sensitivity to PARP Inhibitors, Platinum, and Survival," Cancer Research, 2012, 5675-5682.
Murayama-Hosokawa, S. et al., "Genome-wide single-nucleotide polymorphism arrays in endometrial carcinomas associate extensive chromosomal instability with poor prognosis and unveil frequent chromosomal imbalances involved in the PI3-kinase pathway," Oncogene, Apr. 1, 2010, vol. 29, No. 13, pp. 1897-908.
Nannya et al. "A Robust Algorithm for Copy Number Detection Using High-Density Oligonucleotide Single Nucleotide Polymorphism Genotyping Arrays", Cancer Research, American Association for Cancer Research, US, vol. 65, No. 14, Jul. 14, 2005 (Jul. 14, 2005), pp. 6071-6079.
Narayan et al; Frequent promoter of methylation of CDH1,DAPK,RARB, and HIC1 genes in carcinoma of cervix uteri: its relationship to clinical outcome; Mol Cancer; 2003;2:24, 12 pages.
Norquist et al; Secondary somatic mutations restoring BRCA1/2 predict chemotherapy resistance in hereditary ovarian carcinomas; J Clin Oncol;2011; 29(22): 3008-3015.
Novak Urban et al: "A high-resolution allelotype of B-cell chronic lymphocytic leukemia (B-CLL)", Blood, American Society of Hematology, US, vol. 100, No. 5, Sep. 1, 2002, pp. 1787-1794.
Ogston et al., Breast. 2(5):320-7 (2003). "A new histological grading system to assess response of breast cancers to primary chemotherapy, prognostic significance and survival."
Osborne et al., "A genome-wide map showing common regions of loss of heterozygosity/allelic imbalance in breast cancer", Cancer Research, vol. 60, No. 14, pp. 3706-3712 (2000).
O'Shaugnessy et al; Iniparib plus chemotherapy in metastatic triple-negative breast cancer; N Engl J Med; 2011; 364(3):205-214.
Ott et al., Clinical Cancer Research, the American Association for Cancer Research, US, 9(6):2307-2315 (2003). "Chromosomal Instability rather than p53 mutation is associated with response to neoadjuvant cisplatin-based chemotherapy in gastric carcinoma".
Patel et al., "Failure of Iniparib to Inhibit Poly(ADP-Ribose) Polymerase in Vitro," Clin Cancer Res, Mar. 2012, 1655-1662.
Patocs, A. et al., "Breast-cancer stromal cells with TP53 mutations and nodal metastases", N. Engl. J. Med., 2007, vol. 357, pp. 2543-2551.
Peng et al., "Genome-wide transcriptome profiling of homologous recombination DNA repair," Nature Communications, 2014, 1-11.
Penning et al. "Discovery and SAR of 2-(1-propylpiperidin-4-yl)-1H-benzimidazole-4-carboxamide: A potent inhibitor of poly(ADP-ribose) polymerase (PARP) for the treatment of cancer", Bioorganic & Medicinal Chemistry, Pergamon, GB, vol. 16, No. 14, Jul. 15, 2008 (Jul. 15, 2008), pp. 6965-6975.
Pfeifer et al. "Genome-wide analysis of DNA copy number changes and LOH in CLL using high-density SNP arrays", Blood, vol. 109, No. 3, Oct. 5, 2006 (Oct. 5, 2006), pp. 1202-1210.
Popova et al. "Genome Alteration Print (GAP): a tool to visualize and mine complex cancer genomic profiles obtained by SNP arrays", Genome Biology, Biomed Central Ltd., London, GB, vol. 10, No. 11, Nov. 11, 2009 (Nov. 11, 2009), p. R128.
Puliti et al., Mutat Res. 686(1-2):74-83 (2010). "Low-copy repeats on chromosome 22q11.2 show replication timing switches, DNA flexibility peaks and stress inducible asynchrony, sharing instability features with fragile sites."
R. Mei: "Genome-wide detection of Allelic Imbalance Using Human SNPs and High-density DNA arrays", Genome Research, vol. 10, No. 8, Aug. 1, 2000, pp. 1126-1137.
Rakha et al. "Basal-like breast cancer: a critical review", Journal of Clinical Oncology, American Society of Clinical Oncology, US, vol. 26, No. 14, May 20, 2008 (May 20, 2008), pp. 2568-2581.
Ramirez, C. et al., "Loss of 1p, 19q, and 10q heterozygosity prospectively predicts prognosis of oligodendroglial tumors—towards individualized tumor treatment?" Neuro. Oncol., May 2010, vol. 12, No. 5, pp. 490-499.
Richard et al., Micro Biol Rev. 72(4):686-727 (2008). "Comparitive genomics and molecular dynamics of DNA repeats in eukaryotes."
Richardson et al., Cancer Cell 9:121-132 (2006). "X chromosomal abnormalities in basal-like human breast cancer."
Ryan et al, 2009 ASCO Annual Meeting, http://meetinglibrary.asco.org/content/34135-65, (2009). "Neoadjuvant cisplatin and bevacizumab in triple negative breast cancer (TNBC): Safety and efficacy."
Sakai et al; Functional restoration of BRCA2 protein by secondary BRCA2 mutations in BRCA2-mutated ovarian carcinoma; Cancer Res; 2009; 69(16):6381-6386.
Sakai et al; Secondary mutations as a mechanism of cisplatin resistance in BRCA2-mutated cancers; Nature; 2008; 451(7182):1116-1120.
Samouelian et al., Cancer Chemother Pharmacol. 54(6): 497-504 (2004). "Chemosensitivity and radiosensitivity profiles of four new human epithelial ovarian cancer cell lines exhibiting genetic alterations in BRCA2, TGFbetaRII, KRAS2, TP53 and/or CDNK2A."
Santana-Davila, R. et al. Journal of Hematology & Oncology 3:42 (Oct. 27, 2010).
Schouten et al., "Challengers in the Use of DNA Repair Deficiency as a Biomarker in Breast Cancer," Journal of Clinical Oncology, 2015, 33(17): 1867-1869.
Schwartz et al., Genes Development 19:2715-2726 (2005). "Homologous recombination and nonhomologous end-ioining repair pathways regulate fragile site stability."
Sebat et al., Science. 305(5683):525-8 (2004). "Large-scale copy number polymorphism in the human genome."
Silva et al., "Loss of heterozygosity in BRCA1 and BRCA2 markers and high-grade malignancy in breast cancer," Breast Cancer Res. & Treatment, Jan. 1999, vol. 53, No. 1, pp. 9-17.
Silver et al. "Efficacy of Neoadjuvant Cisplatin in Triple-Negative Breast Cancer", J. Clin. Oncol. vol. 28, 2010, pp. 1145-1153.
Silver et al., Cell 128(5):991-1005 (2007). "Further evidence for BRCA1 communication with the inactive X chromosome."
Smid et al. "Patterns and incidence of chromosomal instability and their prognostic relevance in breast cancer subtypes", Breast Cancer Research and Treatment, Kluwer Academic Publishers, BO, vol. 128, No. 1, Jul. 15, 2010 (Jul. 15, 2010), pp. 23-30.
Sorlie et al., PNAS 100(14):8418-8423 (2003). "Repeated observation of breast tumor subtypes in independent gene expression data set."
Soule H.D. et al. Cancer Research, 50. 6075-6086. Sep. 15, 1990.
Abkevich et al. "Supplemental Material: Table S1: Validation of copy number determinations by Real Time PCR SNP ID Adjacent Gene Sample Copy Number by Real-Time PCR Copy Number by CCNT SNP A", -1712744 CDKN2A HF505 0.010 0.47 HF1382 0.14 0, Oct. 1, 2006 (Oct. 1, 2006), pp. 5-1713144, XP055085899, Retrieved from the Internet: URL: http://cancerres.aacijournals.org/content/suppl/2006/10/04/66.19.9428.DC2/Supplementary_Tables_1-5.pdf [retrieved on Oct. 29, 2013].

(56) References Cited

OTHER PUBLICATIONS

Al-Mulla et al., "Metastatic recurrence of early-stage colorectal cancer is linked to loss of heterozygosity on chromosomes 4 and 14q" Journal of Clinical Pathology, vol. 59, No. 6, pp. 624-630 (2006).
Argos et al. "Genomewide scan for loss of heterozygosity and chromosomal amplification in breast carcinoma using single-nucleotide polymorphism arrays", Cancer Genetics and Cytogenetics, Vo. 182, No. 2, Apr. 15, 2008, pp. 69-74.
Arlt et al., Molecular and Cellular Biology, 24(15):6701-6709 (2004). "BRCA1 is required for common-fragile-site stability via its G2M checkpoint function."
Ashworth et al. "A Synthetic Lethal Therapeutic Approach: Poly(ADP) Ribose Polymerase Inhibitors for the Treatment of Cancers Deficient in DNA Double-Strand Break Repair", Journal of Clinical Oncology, vol. 26, No. 22, Aug. 1, 2008 (Aug. 1, 2008), pp. 3785-3790.
Bamford et al., British Journal of Cancer 91:355-358 (2004). "The COSMIC (Catalogue of Somatic Mutations in Cancer) database and website."
Beder L B et al.: "Genome-wide analyses on loss of heterozygosity in head and neck squamous cell carcinomas", Laboratory Investigation, vol. 83, No. 1, 2003, pp. 99-105.
Bell et al., Nature 474:609-615 (2011). "Integrated genomic analyses of ovarian carcinoma."
Bengtsson et al., Bioinformatics 25(17):2149-2156 (2009). "A single-array preprocessing methods for estimating full-resolution raw copy numbers from all affymetrix genotyping arrays including genomeWideSNP 5 &6."
Bentsson et al., BMC Bioinformatics 11:245-262 (2010). "TumorBoost: Normalization of allele-specific tumor copy numbers from a single pair of tumor-normal genotyping microarrays."
Beroukhim et al. "Inferring Loss-of-Heterozygosity from Unpaired Tumors Using High-Density Oligonucleotide SNP Arrays", Bioinformatics, vol. 19, No. 5, Jan. 1, 2006 (Jan. 1, 2006), p. 2397.
Birbak et al., Cancer Research, 72(8):1, (2012). Abstract 4823: copy number gain and increased expression of BLM and FANCI is associated with sensitivity to genotoxic chemotherapy in triple negative breast and serous ovarian cancer.
Birkbak et al. "Telomeric allelic imbalance indicates defective DNA repair and sensitivity to DNA-damaging agents"; Cancer Discov; 2012; 2(4): 366-375.
Bouwman et al., Nature Structural and Molecular Biology 17(6):688-696 (2010). "53BP1 loss rescues BRCA1 deficiency and is associated with triple-negative and BRCA-mutated breast cancers."
Bryant et al. "Specific killing of BRCA2-deficient tumours with inhibitors of poly(ADP-ribose) polmerase"; Nature; 2005; 434(7035):913-917.
Buch H N et al.: "Prediction of recurrence of nonfunctioning pituitary tumours by loss of heterozygosity analysis", Clinical Endocrinology, vol. 61, 2004, p. 19-22.
Bunting et al., Cell 141(2):243-54 (2010). "53BP1 inhibits homologous recombination in Brca1-deficient cells by blocking resection of DNA breaks."
Burger et al. Drug Resistance Updates 14:22-34 (2011). "Drug transporters of platinum-based anticancer agents and their clinical significance."
Byrski et al., Breast Cancer Res Treat. 115(2):359-63. (2009). "Response to neoadjuvant therapy with cisplatin in BRCA1-positive breast cancer patients."
Calvert et al. "245 Invited PARP inhibitors in cancer treatment", European Journal of Cancer. Supplement, Pergamon, Oxford, GB, vol. 6, No. 12, Oct. 1, 2008 (Oct. 1, 2008), p. 80.
Carr J. et al. Cancer Genetics and Cytogenetics 172 (2007) 127-138.
Cass et al., Cancer 97(9):2187-95 (2002). "Improved survival in women with BRCA-associated ovarian carcinoma."
Cerbinskaite et al; Defective homologous recombination in human cancers; Cancer Treat Rev; 2012; Epub 2011; 38(2): 89-100.
Cha et al., Science; 297(5581):602-6 (2002). "ATR homolog Mec1 promotes fork progression, thus averting breaks in replication slow zones."
Chang et al., "Assessment of plasma DNA levels, allelic imbalance, and CA 125 as diagnostic tests for cancer", Journal of the National Cancer Institute, vol. 94, No. 22, pp. 1697-1703 (2002).
Cheung T H et al.: "Clinicopathologic significance of loss of heterozygosity on chromosome 1 in cervical cancer" Gynecologic Oncology, Academic Press, London, GB, vol. 96, No. 2, Feb. 1, 2005 (Feb. 1, 2005), pp. 510-515.
Choi et al., "Genetic Classification of Colorectal Cancer Based on Chromosomal Loss and Microsatellite Instability Predicts Survival," Clinical Cancer Research, Jul. 2002, 8: 2311-2322.
Dann et al; BRCA1/2 mutations and expression: response to platinum chemotherapy in patients with advanced stage epithelial ovarian cancer; Gynecol Oncol; 2012;125(3):677-682.
De Preter et al. Cancer Letters 197 (2003) 53-61.
De Soto et al. "The inhibition and treatment of breast cancer with poly (ADP-ribose) polymerase (PARP-1) inhibitors", International Journal of Biological Sciences, Ivyspring International Publisher, AU, vol. 2, No. 4, Jun. 10, 2006 (Jun. 10, 2006), pp. 179-185.
Edwards et al; Resistance to therapy caused by intragenic deletion in BRCA2; Nature; 2008; 451(7182):1111-1115.
Etemadmoghadam et al: "Integrated genome-wide DNA copy number and expression analysis identifies distinct mechanisms of primary chemoresistance in ovarian carcinomas", Clinical Cancer Research, the American Association for Cancer Research, US, vol. 15, No. 4, Feb. 15, 2009 (Feb. 15, 2009), pp. 1417-1427.
European Communication Response for application 11757992.0, dated Mar. 21, 2014.
European Communication Response for application 11757992.0, dated Dec. 9, 2014.
European Communication Response for application 11796544.2, dated Sep. 28, 2015.
European Communication Response, for application 11796544.2, dated Feb. 1, 2016.
European Communication Response for application 11796544.2, dated Aug. 3, 2015.
European Communication Response, for application 12860530.0, dated Feb. 10, 2016.
European Communication, for application 11757992.0, dated Aug. 5, 2014.
European Communication, for application 11757992.0, dated Dec. 10, 2013.
European Communication, for application 11796544.2, dated Jan. 20, 2016.
European Communication, for application 11796544.2, dated May 11, 2015.
European Communication, for application 11796544.2, dated Sep. 11, 2015.
European Communication, for application 12801070.9, dated Apr. 1, 2016.
European Intention to Grant, for application 11757992.0, dated Jul. 28, 2015.
European Intention to Grant, for application 11796544.2, dated Mar. 31, 2016.
Extended European Search Report, app. No. 12801070.9, dated Dec. 3, 2014.
Extended European Search Report, for application EP11796544.2, dated Nov. 18, 2013.
Extended European Search Report, for application EP15189527.3, dated Mar. 31, 2016.
Extended European Search Report, from Application EP11748075.6, dated Jul. 29, 2013.
European Communication from Application No. 12801070.9, dated Dec. 22, 2016.
Birkbak et al., "Amount of Allelic Imbalance Predicts Response to Cisplatin in Breast and Ovarian Cancer", Annals of Oncology 21 (2010).
Canadian Office Action from Application No. 2,802,882, dated Feb. 24, 2017.
European Communication Response, for application 12860530.0, dated Mar. 17, 2017.

(56) References Cited

OTHER PUBLICATIONS

Canadian Office Action from Application No. 2,860,312 dated Oct. 15, 2018, 6 pages.
European Communication Response from Application No. 17194403.6, dated Nov. 5, 2018, 5 pages.
Australian Office Action from application No. 2012358244, dated Apr. 24, 2018, 4 pages.
Australian Office Action Response from application No. 2012358244, dated Apr. 19, 2018, 9 pages.
Australian Voluntary Amendment from application No. 2014248007, dated Apr. 20, 2018, 14 pages.
Beroukhim et al., PNAS, 2007, vol. 104, No. 50, pp. 20007-20012.
Canadian Office Action from Application No. 2,839,210, dated Feb. 28, 2018, 4 pages.
European Communication Response from Application No. 12801070.9, dated Feb. 9, 2018, 3 pages.
European Communication Response from Application No. 12860530.0, dated Mar. 12, 2018, 6 pages.
European Communication Response from Application No. 14779403.6, dated Feb. 12, 2018, 10 pages.
Extended European Search Report from Application No. EP17194403.6, dated Feb. 8, 2018, 15 pages.
Haluska et al., European Journal of Cancer, 2014, vol. 50 Supplement, pp. 72-73.
Horiuchi et al., Acta Obstetrica et Gynaecologica Japonica, 2008, vol. 60, No. 11, pp. 1844-1854.
International Preliminary Report on Patentability and Written Opinion from Application No. PCT/US2011/040953, dated Jan. 3, 2013, 6 pages.
International Preliminary Report on Patentability and Written Opinion from Application No. PCT/US2011/048427, dated Mar. 7, 2013, 11 pages.
International Preliminary Report on Patentability and Written Opinion from Application No. PCT/US2012/042668, dated Jan. 3, 2014, 7 pages.
International Preliminary Report on Patentability and Written Opinion from Application No. PCT/US2014/033014, dated Oct. 15, 2015, 6 pages.
International Preliminary Report on Patentability and Written Opinion from Application No. PCT/US2015/045561, dated Mar. 2, 2017, 8 pages.
International Preliminary Report on Patentability and Written Opinion from Application No. PCT/US2015/064473, dated Jun. 22, 2017, 10 pages.
International Search Report and Written Opinion from Application No. PCT/US2014/033014, dated Aug. 12, 2014, 6 pages.
International Search Report and Written Opinion from Application No. PCT/US2015/064473, dated Apr. 14, 2016, 14 pages.
Japanese Office Action from Application No. 2016-506657, dated Jan. 31, 2018, 3 pages.
O'Brien et al., "Converting cancer mutations into therapeutic opportunities," EMBO Mol. Med. 1:297-299 (2009).
Roscillli et al., Annual Meeting of the American Association for Cancer Research, Apr. 17-21, 2010, No. 685, 5 pages.
Sandhu et al., Lancet Oncology, 2013, vol. 14, pp. 882-892.
Timms et al., (10.1158/0008-5472.SABCS13-P6-05-10 Published Dec. 2013 Abstracts: Thirty-Sixth Annual CTRC-AACR San Antonio Breast Cancer Symposium—Dec. 10-14, 2013, 2 pages.
European Communication from Application No. 14809384.2, dated Sep. 6, 2018, 5 pages.
European Communication Response from Application No. 14779403.6, dated Sep. 26, 2018, 12 pages.
Japanese Office Action Response from Application No. 2016-506657, dated Jul. 27, 2018, 10 pages.
Lieberfarb, M.E. et al. Cancer Research 63:4781 (Aug. 2003).
Stronach et al., Molecular Cancer Research, 2018, vol. 16, No. 7, pp. 1103-1111.
M William Audeh, "Novel treatment strategies in triple-negative breast cancer: specific role of poly(adenosine diphosphate-ribose) polymerase inhibition", Pharmacogenomics and Personalized Medicine, 2014:7 pp. 307-316.
Australian Office Action response—Application No. 2012358244, dated Jul. 30, 2018.
European Communication—Application No. 12801070.9-1118, dated Jul. 18, 2018.
European Communication—Application No. 12860530.0-1111, dated May 11, 2018.
European Communication—Application No. 14779403.6-1118, dated Jun. 13, 2018.
European Communication—Application No. 15757372.6-1111, dated Jun. 14, 2018.
European Communication—Application No. 158664755-1111 / 3230472 PCT/US2015064473, dated Jun. 1, 2018.
European Patent Office response—Application No. 12860530.0-1403, dated May 15, 2018.
European Patent Office response—Application No. 12860530.0-1111, dated Jun. 27, 2018.
European Patent Office response—Application No. 15757372.6-1403, dated Jun. 1, 2018.
European Search Report—Application No. 15866475.5-1111 /3230472 PCT/US2015064473, dated May 14, 2018.
Sharoni Jacobs, "Genome-Wide, High-Resolution Detection of Copy Number, Loss of Heterozygosity, and Genotypes from Formalin-Fixed, Paraffin-Embedded Tumor Tissue Using Microarrays", Research Article, 67:6, Mar. 15, 2007, pp. 2544-2551.

* cited by examiner

US 11,149,316 B2

METHODS FOR DETECTING INACTIVATION OF THE HOMOLOGOUS RECOMBINATION PATHWAY (BRCA1/2) IN HUMAN TUMORS

RELATED PATENT APPLICATIONS

The present patent application is filed pursuant to 35 U.S.C § 371 as a U.S. National Phase application of International Patent Application No. PCT/EP2014/076786, which was filed on Dec. 5, 2014, claiming the benefit of priority to U.S. Provisional Patent Application No. 61/913,637 filed on Dec. 9, 2013. The content of each of the aforementioned patent applications is incorporated herein by reference in its entirety.

FIELD OF THE INVENTION

The invention relates to methods for detecting a predisposition to develop cancer and methods for treating cancer.

BACKGROUND OF THE INVENTION

Cancer is a class of diseases in which a group of cells display the traits of uncontrolled growth (growth and division beyond the normal limits), invasion (intrusion on and destruction of adjacent tissues), and sometimes metastasis (spread to other locations in the body via lymph or blood). Cancers can be classified according to the organ, tissue and cell-type from which the cancerous cells originate: lung, colon, liver, skin etc.

Cancer represents one of the leading causes of death in the world. Successful treatment relies on the diagnosis of the disease at very early stages and on the choice of adapted therapies. A plurality of risk factors (lifestyle related, genetic etc.) has been identified for certain types of cancers.

As just one example, basal-like breast carcinomas (BLCs) are generally described as high grade ductal carcinomas, having so-called triple negative (TNBC) phenotype (absence of estrogen receptor [ER], progesterone receptor [PR] and HER2/ERBB2 overexpression) and characterized by the markers expressed by the normal basal/myoepithelial cells of the mammary gland (such as cytokeratins 5/6, 14, 17 and EGFR (for review,[1,2]).

There is an unfulfilled need in the art for methods for detecting homologous recombination deficiency and/or BRCA-deficiency, as well as diagnosing a particular prognosis or likelihood of response to a particular treatment, in basal-like, luminal, and HER2-overexpressing breast carcinomas and other cancers.

SUMMARY OF THE INVENTION

The inventors have discovered that detection of large-scale chromosome breaks, especially at least some number of breaks, can detect Homologous Recombination (HR) deficiency, regardless of the mechanism of inactivation.

Hence, in one aspect, the invention relates to a method for detecting deficiency in the DNA homologous recombination (HR) pathway in a patient suffering from cancer, comprising quantifying the number of rearrangements in the genomic DNA (e.g., Large Scale Transitions (LSTs)) of a tumor sample obtained from said patient, wherein the number of rearrangements corresponds to the number (e.g., per genome) of breakpoints resulting in segments of at least 3, 4, 5, 6, 7, 8, 9, 10, 11, 12, 13, 14, 15, 16, 17, 18, 19, or 20 megabases.

In another aspect, the present invention provides a method of predicting the status of BRCA1 and BRCA2 genes in a cancer cell. The method comprises, or consists essentially of, determining, in one or more cancer cells, the total number of rearrangements (e.g., LSTs) in at least one pair of human chromosomes, wherein the number of rearrangements corresponds to the number (e.g., per genome) of breakpoints resulting in segments of at least 3, 4, 5, 6, 7, 8, 9, 10, 11, 12, 13, 14, 15, 16, 17, 18, 19, or 20 megabases; and diagnosing an increased likelihood of a deficiency in the BRCA1 or BRCA2 gene in a cell having a total number of rearrangements that are greater than a reference number.

In another aspect, the present invention features a method for assessing cancer cells of a patient for the presence of rearrangements (e.g., LSTs) in the genomic DNA of a tumor sample obtained from a patient. The method comprises, or consists essentially of, (a) detecting the number of rearrangements in the genomic DNA of a tumor sample obtained from said patient, wherein the number of rearrangements corresponds to the number (e.g., per genome) of breakpoints resulting in segments of at least 3, 4, 5, 6, 7, 8, 9, 10, 11, 12, 13, 14, 15, 16, 17, 18, 19, or 20 megabases, and (b) identifying the patient as having cancer cells with the rearrangement.

In another aspect, the present invention features a method for detecting HR deficiency (sometimes called herein an HR deficient status) in cancer cells of a patient. The method comprises, or consists essentially of, (a) detecting a number of rearrangements (e.g., LSTs) in the genomic DNA of a tumor sample obtained from said patient, wherein the number of rearrangements corresponds to the number (e.g., per genome) of breakpoints resulting in segments of at least 3, 4, 5, 6, 7, 8, 9, 10, 11, 12, 13, 14, 15, 16, 17, 18, 19, or 20 megabases, and (b) diagnosing the patient as having cancer cells with the HR deficient status.

In another aspect, the present invention features a method for assessing cancer cells of a patient for the presence of a genetic mutation within a gene from an HR pathway. The method comprises, or consists essentially of, (a) detecting a number of rearrangements (e.g., LSTs) in the genomic DNA of a tumor sample obtained from said patient, wherein the number of rearrangements corresponds to the number (e.g., per genome), of breakpoints resulting in segments of at least 3, 4, 5, 6, 7, 8, 9, 10, 11, 12, 13, 14, 15, 16, 17, 18, 19, or 20 megabases, and (b) identifying the patient as having cancer cells with the genetic mutation.

In another aspect, the present invention features a method for performing a diagnostic analysis of a cancer cell of a patient. The method comprises, or consists essentially of, (a) detecting a number of rearrangements (e.g., LSTs) in the genomic DNA of a tumor sample obtained from said patient, wherein the number of rearrangements corresponds to the number (e.g., per genome), of breakpoints resulting in segments of at least 3, 4, 5, 6, 7, 8, 9, 10, 11, 12, 13, 14, 15, 16, 17, 18, 19, or 20 megabases, and (b) diagnosing the patient as having cancer cells with a genomic rearrangement signature.

In another aspect, the present invention features a method for performing a diagnostic analysis of a cancer cell of a patient. The method comprises, or consists essentially of, (a) detecting a number of rearrangements (e.g., LSTs) in the genomic DNA of a tumor sample obtained from said patient, wherein the number of rearrangements corresponds to the number (e.g., per genome), of breakpoints resulting in segments of at least 3, 4, 5, 6, 7, 8, 9, 10, 11, 12, 13, 14, 15, 16, 17, 18, 19 or 20 megabases, and (b) diagnosing the patient as having cancer cells with a HR deficient status.

In another aspect, the present invention features a method for performing a diagnostic analysis of a cancer cell of a patient. The method comprises, or consists essentially of, (a) detecting a number of rearrangements (e.g., LSTs) in the genomic DNA of a tumor sample obtained from said patient, wherein the number of rearrangements corresponds to the number (e.g., per genome), of breakpoints resulting in segments of at least 3, 4 5, 6, 7, 8, 9, 10, 11, 12, 13, 14, 15, 16, 17, 18, 19 or 20 megabases, and (b) diagnosing the patient as having cancer cells with a genetic mutation within a gene from an HR pathway.

In another aspect, the present invention features a method for performing a diagnostic analysis of a cancer cell of a patient to determine if the cancer patient is likely to respond to a cancer treatment regimen comprising administering radiation or a drug selected from the group consisting of DNA damaging agents, anthracyclines, topoisomerase I inhibitors, and PARP inhibitors. The method comprises, or consists essentially of, (a) detecting a number of rearrangements (e.g., LSTs) in the genomic DNA of a tumor sample obtained from said patient, wherein the number of rearrangements corresponds to the number (e.g., per genome), of breakpoints resulting in segments of at least 3, 4, 5, 6, 7, 8, 9, 10, 11, 12, 13, 14, 15, 16, 17, 18, 19 or 20 megabases, and (b) diagnosing the patient as being likely to respond to the cancer treatment regimen.

In another aspect, the present invention features a method for diagnosing a patient as having cancer cells having a rearrangement (e.g., an LST) in the genomic DNA of a tumor sample. The method comprises, or consists essentially of, (a) detecting a number of rearrangements (e.g., LSTs) in the genomic DNA of a tumor sample obtained from said patient, wherein the number of rearrangements corresponds to the number (e.g., per genome), of breakpoints resulting in segments of at least 3, 4, 5, 6, 7, 8, 9, 10, 11, 12, 13, 14, 15, 16, 17, 18, 19 or 20 megabases, and (b) diagnosing the patient as having cancer cells with the rearrangement in the genomic DNA of a tumor sample.

In another aspect, the present invention features a method for diagnosing a patient as having cancer cells with an HR deficient status. The method comprises, or consists essentially of, (a) determining that the patient comprises one or more cancer cells having the HR deficiency status, wherein the presence of more than a reference number of rearrangements (e.g., LSTs) in the genomic DNA of the tumor sample indicates that the cancer cells have the HR deficiency status, and (b) diagnosing the patient as having cancer cells with the HR deficient status.

In another aspect, the present invention features a method for diagnosing a patient as having cancer cells with a genetic mutation within a gene from an HR pathway. The method comprises, or consists essentially of, (a) determining that the patient comprises one or more cancer cells having the genetic mutation, detecting a number of rearrangements (e.g., LSTs) in the genomic DNA of a tumor sample obtained from said patient, wherein the presence of more than a reference number of rearrangements in the genomic DNA of the tumor sample indicates that the cancer cells have the HR deficiency status, and (b) diagnosing the patient as having cancer cells with the genetic mutation.

In another aspect, the present invention features a method for diagnosing a patient as being a candidate for a cancer treatment regimen comprising administering radiation or a drug selected from the group consisting of DNA damaging agents, anthracyclines, topoisomerase I inhibitors, and PARP inhibitors. The method comprises, or consists essentially of, (a) determining that the patient comprises one or more cancer cells having the genetic mutation, detecting a number of rearrangements (e.g., LSTs) in the genomic DNA of a tumor sample obtained from said patient, wherein the presence of more than a reference number of rearrangements in the genomic DNA of the tumor sample indicates that the cancer cells have the HR deficiency status, and (b) diagnosing, based at least in part on the presence of the genomic DNA rearrangement, the patient as being likely to respond to the cancer treatment regimen.

The invention also relates to a method for treating cancer in a patient wherein said cancer is linked to a deficiency in the HR pathway, wherein said treatment comprises a PARP inhibitor, an alkylating agent, a DNA damaging agent, an anthracycline, a topoisomerase I inhibitor, and/or radiation, and wherein said method comprises the step consisting of predicting deficiency on the HR pathway as described above. The method comprises, or consists essentially of, determining, in a cancer cell from the cancer patient, the number of rearrangements (e.g., LSTs) in at least one pair of human chromosomes of a cancer cell, wherein the number of rearrangements corresponds to the number (e.g., per genome), of breakpoints resulting in segments of at least 3, 4, 5, 6, 7, 8, 9, 10, 11, 12, 13, 14, 15, 16, 17, 18, 19, or 20 megabases; and correlating the total number that is greater than a reference number with an increased likelihood that the cancer patient will respond to the cancer treatment regimen. In some embodiments, the patients are treatment naïve patients. The DNA damaging agent can be a platinum-based chemotherapy drug, the anthracycline can be epirubincin or doxorubicin, the topoisomerase I inhibitor can be campothecin, topotecan, or irinotecan, or the PARP inhibitor can be iniparib, olaparib or velapirib. In some embodiments, the patients are treatment naïve patients.

The invention also relates to a method for predicting the efficacy of a treatment in a patient suffering from cancer, wherein said treatment comprises a PARP inhibitor, an alkylating agent, a DNA damaging agent, an anthracycline, a topoisomerase I inhibitor, and/or radiation, and wherein said method comprises the step consisting of predicting deficiency on the HR pathway as described above. The method comprises, or consists essentially of, determining, in one or more cancer cells from the cancer patient, the number of rearrangements (e.g., LSTs) in at least one pair of human chromosomes of a cancer cell, wherein the number of rearrangements corresponds to the number (e.g., per genome), of breakpoints resulting in segments of at least 3, 4, 5, 6, 7, 8, 9, 10, 11, 12, 13, 14, 15, 16, 17, 18, 19, or 20 megabases; and correlating the total number that is greater than a reference number with an increased likelihood that the cancer patient will respond to the cancer treatment regimen. The DNA damaging agent can be a platinum-based chemotherapy drug, the anthracycline can be epirubincin or doxorubicin, the topoisomerase I inhibitor can be campothecin, topotecan, or irinotecan, or the PARP inhibitor can be iniparib, olaparib or velapirib. In some embodiments, the patients are treatment naïve patients.

In another aspect, this invention features the use of a plurality of oligonucleotides capable of hybridizing to a plurality of polymorphic regions of human genomic DNA in a cancer cell, in the manufacture of a diagnostic kit useful for determining a total number of rearrangements (e.g., LSTs) in at least one pair of human chromosomes, wherein the number of rearrangements corresponds to the number (e.g., per genome), of breakpoints resulting in segments of at least 3, 4, 5, 6, 7, 8, 9, 10, 11, 12, 13, 14, 15, 16, 17, 18, 19, or 20 megabases; and for detecting (a) an increased likelihood of a deficiency in the BRCA1 or BRCA2 gene in the cancer cell, (b) an increased likelihood of a deficiency in HR in the cancer cell, or (c) an increased likelihood that a cancer patient will respond to cancer treatment regimen comprising a DNA damaging agent, an anthracycline, a topoisomerase I inhibitor, radiation, or a PARP inhibitor. The cancer cell can be an ovarian or breast cancer cell.

In another aspect, the invention provides a computer program product embodied in a computer readable medium that, when executed on a computer, provides instructions for detecting the presence or absence of rearrangements (e.g., LSTs) in the genomic DNA of a tumor sample obtained from a patient, wherein the number of rearrangements corresponds to the number (e.g., per genome), of breakpoints resulting in segments of at least 3, 4 5, 6, 7, 8, 9, 10, 11, 12, 13, 14, 15, 16, 17, 18, 19, or 20 megabases. The computer program product can include other instructions. The cancer cell can be an ovarian, breast, or esophageal cancer cell. The DNA damaging agent can be a platinum-based chemotherapy drug, the anthracycline can be epirubincin or doxorubicin, the topoisomerase I inhibitor can be campothecin, topotecan, or irinotecan, or the PARP inhibitor can be iniparib, olaparib or velapirib.

In another aspect, the invention features a system for determining the number of rearrangements (e.g., LSTs) in the genomic DNA of a tumor sample obtained from said patient, wherein the number of rearrangements corresponds to the number (e.g., per genome), of breakpoints resulting in segments of at least 3, 4, 5, 6, 7, 8, 9, 10, 11, 12, 13, 14, 15, 16, 17, 18, 19, or 20 megabases. The system comprises, or consists essentially of, (a) a sample analyzer configured to produce a plurality of signals about genomic DNA of at least one pair of human chromosomes of the cancer cell, and (b) a computer sub-system programmed to calculate, based on the plurality of signals, the number of rearrangements in the genomic DNA of a tumor sample. The computer sub-system can be programmed to compare the number of rearrangements in the genomic DNA of a tumor sample to a reference number to determine (a) a likelihood of a deficiency in BRCA1 and/or BRCA2 genes in the cancer cell, (b) a likelihood of a deficiency in HR in the cancer cell, or (c) a likelihood that the cancer patient will respond to cancer treatment regimen comprising a DNA damaging agent, an anthracycline, a topoisomerase I inhibitor, radiation, or a PARP inhibitor. The system can comprise an output module configured to display the likelihood of (a), (b), or (c). The system can comprise an output module configured to display a recommendation for the use of the cancer treatment regimen. The Indicator Rearrangement Regions can be determined in at least two, five, ten, or 21 pairs of human chromosomes. The cancer cell can be an ovarian, breast, lung, or esophageal cancer cell. The DNA damaging agent can be a platinum-based chemotherapy drug, the anthracycline can be epirubincin or doxorubicin, the topoisomerase I inhibitor can be campothecin, topotecan, or irinotecan, or the PARP inhibitor can be iniparib, olaparib or velapirib.

In another aspect, the present invention provides a diagnostic kit. The kit comprises, or consists essentially of, at least 500 oligonucleotides capable of hybridizing to a plurality of polymorphic regions of human genomic DNA; and a computer program product provided herein. The computer program product can be embodied in a computer readable medium that, when executing on a computer, provides instructions for detecting rearrangements in genomic DNA of a tumor sample obtained from a patient, wherein the number of rearrangements corresponds to the number (e.g., per genome), of breakpoints resulting in segments of at least 3, 4, 5, 6, 7, 8, 9, 10, 11, 12, 13, 14, 15, 16, 17, 18, 19, or 20 megabases.

DESCRIPTION OF THE DRAWINGS

FIG. 11A. 317 near-diploid tumors. FIG. 11B. 139 near-tetraploid tumors.

DETAILED DESCRIPTION OF THE INVENTION

Figure 1:
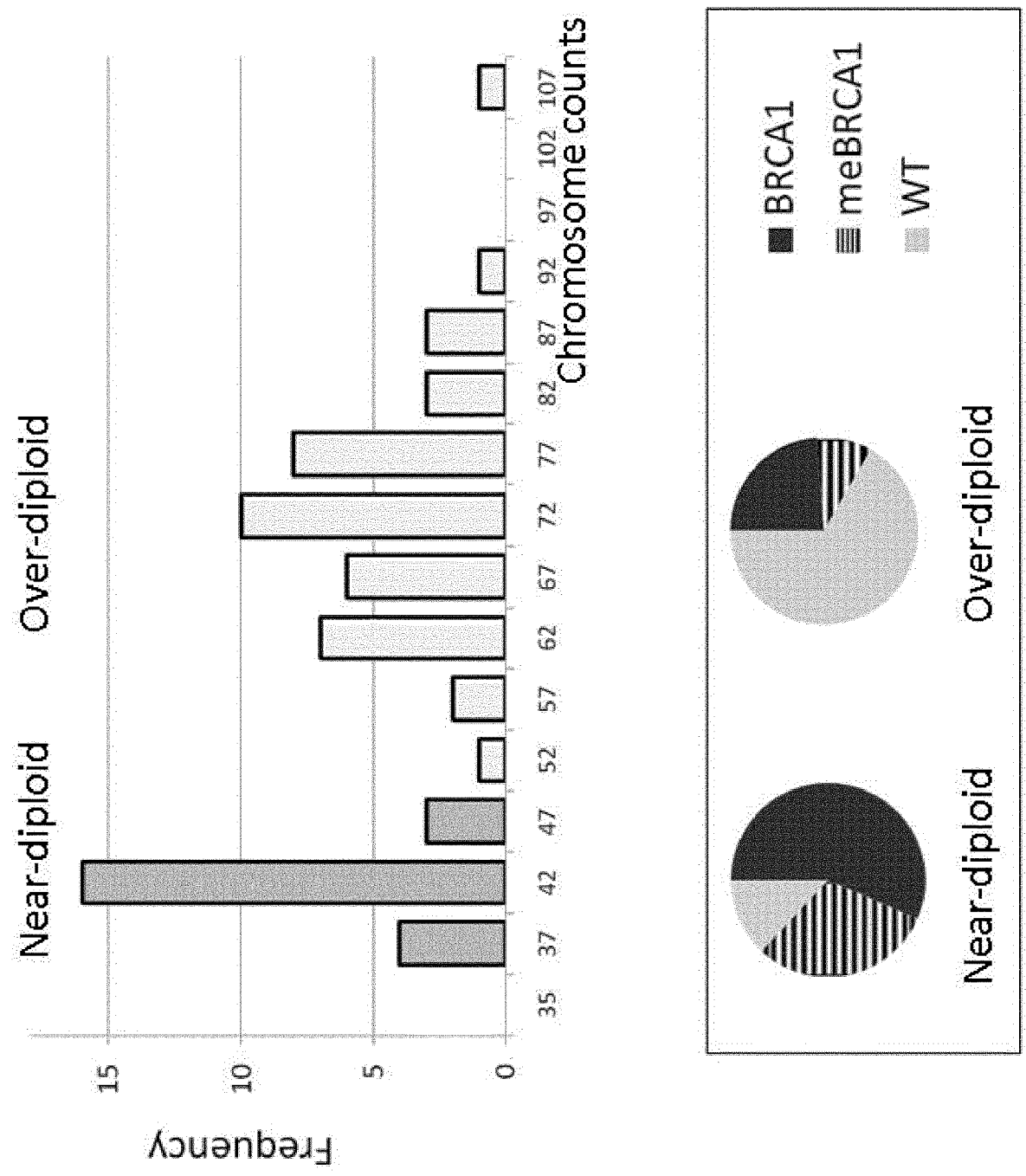
FIG. 1. Chromosome content and BRCA1 status in BLCs. A. Distribution of the chromosome content in the set of BLCs displayed two modes, which evidences 2 populations of tumors with different ploidy status. B. Near-diploid tumors (<50 chromosomes) and over-diploid tumors (>=50 chromosomes) showed different proportions of proven BRCA1-inactivated tumors. WT correspond to non BRCA1.

Methods for Predicting Deficiency in the DNA Homologous Recombination Pathway

In one aspect, the invention relates to a method for detecting deficiency in the DNA homologous recombination (HR) pathway in a patient suffering from cancer, comprising quantifying the number of rearrangements (e.g., LSTs) in the genomic DNA of a tumor sample obtained from said patient, wherein the number of rearrangements corresponds to the number (e.g., per genome), of breakpoints resulting in segments of at least 3, 4, 5, 6, 7, 8, 9, 10, 11 12, 13, 14, 15, 16, 17, 18, 19 or 20 megabases.

A rearrangement can be a large-scale transition (LST). LST refers to any somatic copy number transition (e.g., breakpoint) along the length of a chromosome where is between two regions of at least some minimum length (e.g., at least 3, 4, 5, 6, 7, 8, 9, 10, 11 12, 13, 14, 15, 16, 17, 18, 19 or 20 or more megabases) after filtering out regions shorter than some maximum length (e.g., 0.1, 0.2, 0.3, 0.4, 0.5, 0.6, 0.7, 0.8, 0.9, 1, 1.5, 2, 2.5, 3, 3.5, 4 or more megabases). For example, if after filtering out regions shorter than 3 megabases the somatic cell has a copy number of 1:1 for, e.g., at least 10 megabases and then a breakpoint transition to a region of, e.g., at least 10 megabases with copy number 2:2, this is an LST. An alternative way of defining the same phenomenon is as an LST Region, which is genomic region with stable copy number across at least some minimum length (e.g., at least 3, 4, 5, 6, 7, 8, 9, 10, 11 12, 13, 14, 15, 16, 17, 18, 19 or 20 megabases) bounded by breakpoints (e.g., transitions) where the copy number changes for another region also at least this minimum length. For example, if after filtering out regions shorter than 3 megabases the somatic cell has a region of at least 10 megabases with copy number of 1:1 bounded on one side by a breakpoint transition to a region of, e.g., at least 10 megabases with copy number 2:2, and bounded on the other side by a breakpoint transition to a region of, e.g., at least 10 megabases with copy number 1:2, then this is two LSTs. Notice that this is broader than allelic imbalance because such a copy number change would not be considered allelic imbalance (because the copy proportions 1:1 and 2:2 are the same, e.g., there has been no change in copy proportion). LST and its use in determining HRD is described in detail in Popova et al., Ploidy and large-scale genomic instability consistently identify basal-like breast carcinomas with BRCA1/2 inactivation, CANCER RES. (2012) 72:5454-5462.

Typically, the method of the invention comprises the step of comparing the number of rearrangements (e.g., per genome) to a reference, wherein a number of rearrangements (e.g., per genome) greater than said reference is indicative of HR deficiency.

As used herein, the term "patient" denotes a mammal, such as a rodent, a feline, a canine, a bovine, an equine, a sheep, a porcine or a primate. Preferably, a patient according to the invention is a human.

The inventors have invented methods, systems, etc. for detecting BRCA deficiency, HR deficiency, likelihood of treatment response, etc. in patients whose cells (e.g., tumor cells) have a genome that contains a greater number of breakpoints than cells or tumors from control patients (e.g., patients suffering from cancers which do not harbor such BRCA deficiency, HR deficiency, etc.).

More specifically, the inventors have demonstrated that the relevant breakpoints are those which result in genomic DNA segments of at least 3, 4, 5, 6, 7, 8, 9, 10, 11 12, 13, 14, 15, 16, 17, 18, 19 or 20 megabases (often referred to herein as "large-scale transitions" or "LSTs"). According to some embodiments of the invention, the breakpoints which result in smaller segments are not taken into account. In some embodiments, the location of breakpoints along the genome is not important in the detection and breakpoints with local concentration are not correlated with the homologous recombination status. In such embodiments, it is the genome-wide number of breakpoints that can be used to detect HR deficiency.

As used herein, the expression "DNA homologous recombination (HR) pathway" has its general meaning in the art. It refers to the cellular pathway through which Double Stranded DNA breaks (DSB) are repaired by a mechanism called Homologous Recombination. Inside mammalian cells, DNA is continuously exposed to damage arising from exogenous sources such as ionizing radiation or endogenous sources such as byproducts of cell replication. All organisms have evolved different strategies to cope with these lesions. One of the most deleterious forms of DNA damage is DSB. In mammalian cells, there are two major pathways to repair DSB: Homologous recombination (HR) and Non Homologous End Joining (NHEJ). HR is the most accurate mechanism to repair DSB because it uses an intact copy of the DNA from the sister chromatid or the homologous chromosome as a matrix to repair the break.

Cells (e.g., cancer cells) identified as having genomic DNA rearrangements (e.g., LSTs) according to the present disclosure can be classified as having an increased likelihood of having an HR deficiency and/or as having an increased likelihood of having a deficient status in one or more genes in the HR pathway. For example, cancer cells identified as having increased genomic DNA rearrangements can be classified as having an increased likelihood of having an HR deficient status. In some cases, cancer cells identified as having increased genomic DNA rearrangements can be classified as having an increased likelihood of having a deficient status for one or more genes in the HR pathway. As used herein, deficient status for a gene means the sequence, structure, expression and/or activity of the gene or its product is/are deficient as compared to normal. Examples include, but are not limited to, low or no mRNA or protein expression, deleterious mutations, hypermethylation, attenuated activity (e.g., enzymatic activity, ability to bind to another biomolecule), etc. As used herein, deficient status for a pathway (e.g., HR pathway) means at least one gene in that pathway (e.g., BRCA1) has a deficient status. Examples of highly deleterious mutations include frameshift mutations, stop codon mutations, and mutations that lead to altered RNA splicing. Deficient status in a gene in the HR pathway may result in deficient or reduced HR activity in cells (e.g., cancer cells).

Examples of genes in the HR pathway include, without limitation, the genes listed in Table 1, and BRCA1, BRCA2, PALB2/FANCN, BRIP1/FANCJ, BARD1, RAD51 and RAD51 paralogs (RAD51B, RAD51C, RAD51D, XRCC2, XRCC3) are proteins that are important for the repair of double-strand DNA breaks by the HR pathway. When the gene for any such protein is, e.g., mutated or under-expressed, the change can lead to errors in DNA repair that can eventually cause cancer. Although not yet found recurrently mutated in human tumors, other actors of the HR pathway may potentially be deregulated in cancers, such as FANCA, FANCB, FANCC, FANCD2, FANCE, FANCG, FANCI, FANCL, FANCM, FAN1, SLX4/FANCP or ERCC1.

TABLE 1

Selected HR Pathway Genes

| Gene Name | Entrez Gene Symbol (if assigned) | Entrez Gene Id |
|---|---|---|
| BLM | BLM | 641 |
| BRCA1 | BRCA1 | 672 |
| BRCA2 | BRCA2 | 675 |
| CtIP | RBBP8 | 5932 |
| DNA polymerase delta | POLD1 | 5424 |
|  | POLD2 | 5424 |
|  | POLD3 | 10714 |
|  | POLD4 | 57804 |
| DNA polymerase eta | POLH | 5429 |
| DNA2 | DNA2 | 1763 |
| EME1 | EME1 | 146956 |
| ERCC1 | ERCC1 | 2067 |
| EXO1 | EXO1 | 9156 |
| FANCM | FANCM | 57697 |
| GEN1 | GEN1 | 348654 |
| MRE11 | MRE11A | 4361 |
| MUS81 | MUS81 | 80198 |
| NBS1 | NBN | 4683 |
| PALB2 | PALB2 | 79728 |
| PCNA | PCNA | 5111 |
| RAD50 | RAD50 | 10111 |
| RAD51 | RAD51 | 5888 |
| RAD51AP1 | RAD51AP1 | 10635 |
| RAD51B | RAD51B | 5890 |
| RAD51C | RAD51C | 5889 |
| RAD51D | RAD51D | 5892 |
| RAD54 | ATRX | 546 |
| RAD54B | RAD54B | 25788 |
| RMI1 | RMI1 | 80010 |
| RMI2 | C16orf75 | 116028 |
| RPA | RPA1 | 6117 |
| RTEL1 | RTEL1 | 51750 |
| SLX1 |  |  |
| SLX2 |  |  |

TABLE 1-continued

Selected HR Pathway Genes

| Gene Name | Entrez Gene Symbol (if assigned) | Entrez Gene Id |
|---|---|---|
| SLX4 | SLX4 | 84464 |
| TOP2A | TOP2A | 7153 |
| XPF | ERCC4 | 2072 |
| XRCC2 | XRCC2 | 7516 |
| XRCC3 | XRCC3 | 7517 |

Examples of genetic mutations that can be present within a gene of the HR pathway include, without limitation, those listed in Table 2.

TABLE 2

Possible genetic mutations within selected genes of the HR pathway.

| Gene | Mutation | Entrez Gene ID |
|---|---|---|
| BRCA1 | C24F | 672 |
| BRCA1 | E29X | 672 |
| BRCA2 | R3052W | 675 |
| BRCA2 | 2881delG | 675 |
| RAD51C | G125V | 5889 |
| RAD51C | L138F | 5889 |
| RAD51C | Y75XfsX0 | 5889 |

Thus, the expression "deficiency in the HR pathway", as used herein, refers to a condition in which one or more of the proteins involved in the HR pathway for repairing DNA is deficient or inactivated.

Proteins involved in the HR pathway can encompass, but are not limited to, inactivation of at least one of the following genes: BRCA1, BRCA2, PALP2/FANCN, BRIP1/FANCJ, BARD1, RAD51, RAD51 paralogs (RAD51B, RAD51C, RAD51D, XRCC2, XRCC3), FANCA, FANCB, FANCC, FANCD2, FANCE, FANCG, FANCI, FANCL, FANCM, FAN1, SLX4/FANCP and ERCC1, and the genes listed in Tables 1 and 2.

Unless stated otherwise, as used herein the expressions "deficiency in the HR pathway" or "tumor deficiency in the HR pathway" are used interchangeably. That is, the invention generally relates to detecting deficiencies in tumor cells and so any discussion should be automatically assumed to extend to tumor cells.

As used herein the term "inactivation", when referring to a gene, can mean any type of deficiency of said gene. It includes but is not limited to germline mutations in the coding sequence, somatic mutations in the coding sequence, mutations in the promoter and methylation of the promoter.

In one embodiment of the invention, the deficiency in the HR pathway is a BRCA1 mutation. Several BRCA1 mutations have already been described in the art and are known to be associated with certain types of cancer, such as breast and ovary cancers[55]. In another embodiment of the invention, the deficiency in the HR pathway is a BRCA2 mutation[56]. In yet another embodiment of the invention, the deficiency in the HR pathway is hypermethylation of the BRCA1 promoter[57].

As used herein, the term "cancer" has its general meaning in the art. It refers to the pathological condition in mammals that is characterized by unregulated cell growth.

Examples of cancer can include, but are not limited to, solid tumors or a carcinoma. Preferably, the solid tumor is selected from breast cancer, colon cancer, lung cancer, prostate cancer, renal cancer, metastatic or invasive malignant melanoma, brain tumor, bladder cancer, head and neck cancer, and liver cancer. Carcinoma includes bladder, breast, colon, kidney, liver, lung, ovary, pancreas, stomach, cervix, thyroid or skin carcinoma, including squamous cell carcinoma. However, the present invention also contemplates hematopoietic tumors such as leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, Burkitt's lymphoma, acute and chronic myelogenous leukemias and promyelocytic leukemia.

In one embodiment, said cancer is selected from the group consisting of breast cancer, ovary cancer, pancreas cancer, head and neck cancer and melanoma.

In a preferred embodiment, said cancer is selected from the group consisting of breast cancer, ovary cancer, cervix cancer, pancreas cancer and lung cancer.

In a more preferred embodiment, said cancer is a breast cancer. The breast cancer can be basal-like, luminal, or HER2-overexpressing breast carcinoma.

The tumor sample suitable for carrying out the method of the invention may be any physical specimen from a patient containing cancer cells. This may include, but is not limited to, a biopsy obtained from the diseased tissue or organ (or even the entire organ if such organ has been removed) of the patient suffering from cancer.

Quantification of the Number of Rearrangements

The step of quantifying the number of rearrangements (e.g., LSTs) in the genomic DNA of a sample can be performed by any suitable method in the art.

As mentioned above, the inventors have demonstrated that the relevant breakpoints are those which result in genomic DNA segments of at least 3 megabases. Indeed, preferred cut-off points comprised between 9 and 11, even more preferably about 10 megabases, have been described in the Examples below, but similar results were obtained with cutoff value between 3 megabases and 20 megabases. According to some embodiments of the invention, the breakpoints which result in segments of less than these cutoff points are not taken into account.

The skilled person can readily select techniques for quantifying genomic rearrangements (e.g., LSTs) and filter out the breakpoints that result in genomic DNA segments of less than 3, 4, 5, 6, 7, 8, 9, 10, 11, 12, 13, 14, 15, 16, 17, 18, 19, or 20 megabases. Such techniques will generally measure copy number at a plurality of loci across the genome in order to identify copy number transitions between genomic regions of a certain size (e.g., LSTs). Suitable methods for quantifying rearrangements include, but are not limited to, those described in Le Scouarnec & Gribble, EREDITY (2012) 108:75-85.

In some embodiments, an array-based assay can be used to quantify copy number and LSTs in a sample. Such arrays may comprise nucleic acid probes capable of detecting genotypes (e.g., copy number) at a plurality of genomic loci. Such loci may be known polymorphic loci such as Single/Simple Nucleotide Polymorphisms (SNPs). In some cases the array can be configured for use in comparative genomic hybridization (CGH). Examples of SNP arrays useful according to the invention include the 300K Illumina SNP-array (Human Hap300-Duo) and the Affymetrix SNPChip6.0 array. In the case of the Illumina array, raw data may be processed (e.g., Allele specific signals processed into Log R ratio and B allele frequency) for use in the invention using tQN algorithm. In the case of the Affymetrix array, cell files may be processed by Genotyping Console 3.0.2. Log 2Ratio and Allele Difference profiles resulted from Copy Number and LOH analysis performed with the reference model file HapMap270 (GenomeWideSNP_6.hapmap270.na29) provided by Affymetrix.

In some embodiments, the step of quantifying LSTs is carried out by sequencing techniques, including but not limited to, next-generation sequencing using mate paired libraries or longer reads.[58] For example, genomic DNA from a cell sample (e.g., a cancer cell sample) can be extracted and optionally fragmented. Any appropriate method can be used to extract and optionally fragment genomic nucleic acid including, without limitation, commercial kits such as QIAamp™ DNA Mini Kit (Qiagen™), MagNA™ Pure DNA Isolation Kit (Roche Applied Science™) and GenElute™ Mammalian Genomic DNA Miniprep Kit (Sigma-Aldrich™). Once extracted, either targeted or untargeted sequencing can be done to determine the sample's genotypes (e.g., copy number) at a plurality of loci. For example, whole genome, whole transcriptome, or whole exome sequencing can be done to determine genotypes at millions or even billions of base pairs (e.g., base pairs can be "loci" to be evaluated).

In some embodiments, targeted sequencing of known polymorphic loci (e.g., SNPs and surrounding sequences) can be done as an alternative to microarray analysis. For example, the genomic DNA can be enriched for those fragments containing a locus (e.g., SNP location) to be analyzed using kits designed for this purpose (e.g., Agilent SureSelect™, Illumina TruSeq Capture™, and Nimblegen SeqCap EZ Choice™). For example, genomic DNA containing the loci to be analyzed can be hybridized to biotinylated capture RNA fragments to form biotinylated RNA/genomic DNA complexes. Alternatively, DNA capture probes may be utilized resulting in the formation of biotinylated DNA/genomic DNA hybrids. Streptavidin coated magnetic beads and a magnetic force can be used to separate the biotinylated RNA/genomic DNA complexes from those genomic DNA fragments not present within a biotinylated RNA/genomic DNA complex. The obtained biotinylated RNA/genomic DNA complexes can be treated to remove the captured RNA from the magnetic beads, thereby leaving intact genomic DNA fragments containing a locus to be analyzed. These intact genomic DNA fragments containing the loci to be analyzed can be amplified using, for example, PCR techniques. The amplified genomic DNA fragments can be sequenced using a high-throughput sequencing technology or a next-generation sequencing technology such as Illumina HiSeq™, Illumina MiSeq™, Life Technologies SoLID™ or Ion Torrent™, or Roche 454™.

Computational techniques can also be used to determine the presence of genomic DNA rearrangements (e.g., LSTs). For example, algorithms such as those described elsewhere can be used to detect rearrangement using information from SNP arrays (Nannya et al., Cancer Res. (2005) 65:6071-6079 (2005)). These algorithms often do not explicitly take into account contamination of tumor samples with benign tissue. Cf. International Application No. PCT/US2011/026098 to Abkevich et al.; Goransson et al., PLoS One (2009) 4(6):e6057. This contamination is often high enough to make the detection of rearrangements challenging. Improved analytical methods according to the present invention for identifying rearrangements, even in spite of contamination, include those embodied in computer software products as described below.

In some cases, a selection process can be used to select loci (e.g., SNP loci) to be evaluated using an assay configured to identify genomic rearrangements (e.g., SNP array-based assays and sequencing-based assays). For example, any human SNP location can be selected for inclusion in a SNP array-based assay or a sequencing-based assay configured to identify genomic rearrangements within the genome of cells. In some cases, 0.01, 0.02, 0.03, 0.04, 0.05, 0.075, 0.1, 0.2, 0.3, 0.4, 0.5, 1.0, 1.5, 2.0, 2.5 million or more SNP locations present within the human genome can be evaluated to measure copy number across the genome, including in some embodiments those SNPs that (a) are not present on the Y chromosome, (b) are not mitochondrial SNPs, (c) have a minor allele frequency of at least about five percent in Caucasians, (d) have a minor allele frequency of at least about one percent in three races other than Caucasians (e.g., Chinese, Japanese, and Yoruba), and/or (e) do not have a significant deviation from Hardy Weinberg equilibrium in any of the four races. In some cases, more than 100,000, 150,000, or 200,000 human SNPs can be selected that meet criteria (a) through (e). Of the human SNPs meeting criteria (a) through (e), a group of SNPs (e.g., top 100,000 SNPs) can be selected such that the SNPs have a high degree of allele frequency in a population of interest (e.g., Caucasians), cover the human genome in a relatively evenly spaced manner (e.g., at least one SNP every about 25 kb to about 500 kb), and are not in linkage disequilibrium with another selected SNP in the relevant population. In some cases, about 40, 50, 60, 70, 80, 90, 100, 110, 120, 130 thousand or more SNPs can be selected (e.g., this number of SNPs these criteria) and included in an assay configured to identify genomic rearrangements across a human genome. For example, between about 70,000 and about 90,000 (e.g., about 80,000) SNPs can be selected for analysis with a SNP array-based assay, and between about 45,000 and about 55,000 (e.g., about 54,000) SNPs can be selected for analysis with a sequencing-based assay.

As described herein, a cell sample can be assessed to determine if the genome of cells of the sample contains a genomic DNA rearrangement (e.g., LSTs). Any appropriate type of sample can be assessed. For example, a sample containing cancer cells can be assessed to determine if the genome of the cancer cells contains a genomic DNA rearrangement. Examples of samples containing cancer cells that can be assessed as described herein include, without limitation, tumor biopsy samples (e.g., breast tumor biopsy samples), formalin-fixed, paraffin-embedded (FFPE) tissue samples containing cancer cells, core needle biopsies, fine needle aspirates, and samples containing cancer cells shed from a tumor (e.g., blood, urine or other bodily fluids). For formalin-fixed, paraffin-embedded tissue samples, the sample can be prepared by DNA extraction using a genomic DNA extraction kit optimized for FFPE tissue, including but not limited to those described above (e.g., QuickExtract™ FFPE DNA Extraction Kit (Epicentre™), and QIAamp™ DNA FFPE Tissue Kit (Qiagen™)).

In some cases, laser dissection techniques can be performed on a tissue sample to minimize the number of non-cancer cells within a cancer cell sample to be assessed. In some cases, antibody based purification methods can be used to enrich for cancer cells and/or deplete non-cancer cells. Examples of antibodies that could be used for cancer cell enrichment include, without limitation, anti-EpCAM, anti-TROP-2, anti-c-Met, anti-Folate binding protein, anti-N-Cadherin, anti-CD318, anti-antimesencymal stem cell antigen, anti-Her2, anti-MUC1, anti-EGFR, anti-cytokeratins (e.g., cytokeratin 7, cytokeratin 20, etc.), anti-Caveolin-1, anti-PSA, anti-CA125, and anti-surfactant protein antibodies.

Any type of cancer cell can be assessed using the methods and materials described herein. For example, breast cancer cells, ovarian cancer cells, liver cancer cells, esophageal cancer cells, lung cancer cells, head and neck cancer cells, prostate cancer cells, colon, rectal, or colorectal cancer cells, and pancreatic cancer cells can be assessed to determine if the genome of the cancer cells a genomic DNA rearrangement. In some embodiments, the cancer cells are primary or metastatic cancer cells of ovarian cancer, breast cancer, lung cancer or esophageal cancer.

When assessing the genome of cancer cells for a genomic rearrangement (e.g., an LST), one or more (e.g., one, two, three, four, five, six, seven, eight, nine, ten, eleven, twelve, 13, 14, 15, 16, 17, 18, 19, 20, 21, 22, or 23) pairs of chromosomes can be assessed. In some cases, the genome of cancer cells is assessed for a genomic rearrangement using one or more (e.g., one, two, three, four, five, six, seven, eight, nine, ten, eleven, twelve, 13, 14, 15, 16, 17, 18, 19, 20, 21, 22, 23) pairs of chromosomes.

In some cases, it can be helpful to exclude certain chromosomes from this analysis. For example, in the case of females, a pair to be assessed can include the pair of X sex chromosomes; whereas, in the case of males, a pair of any autosomal chromosomes (e.g., any pair other than the pair of X and Y sex chromosomes) can be assessed.

In some embodiments a reference number (e.g., reference number of LSTs) is or has been previously derived from a relevant reference population. Such reference populations may include patients (a) with the same cancer as the patient being tested, (b) with the same cancer sub-type, (c) with cancer having similar genetic or other clinical or molecular features, (d) who responded to a particular treatment, (e) who did not respond to a particular treatment, (f) who are apparently healthy (e.g., do not have any cancer or at least do not have the tested patient's cancer), etc. The reference number (or length, value or score) may be (a) representative of the number (or value or score) found in the reference population as a whole, (b) an average (mean, median, etc.) of the number (value or score) found in the reference population as a whole or a particular sub-population, (c) representative of the number (value or score) (e.g., an average such as mean or median) found in terciles, quartiles, quintiles, etc. of the reference population as ranked by (i) their respective number (value or score) or (ii) the clinical feature they were found to have (e.g., strength of response, prognosis (including time to cancer-specific death), etc.).
Evaluation of the Ploidy In one embodiment, the method of the invention further comprises a step wherein the ploidy of the tumor sample is evaluated in addition to determining the presence of LSTs, for HR evaluation.

As used herein, the term "ploidy" has its general meaning in the art. It refers to the mean number of copies of each locus in the genome.

Typically, a healthy cell (and therefore a healthy tissue sample) is diploid, e.g. it contains two copies/two alleles of each locus. Certain types of cancer can exhibit whole genome duplication during cancer progression, resulting in over-diploid (tetraploid or more) tumor cells (Ref 40). Thus, tumor samples can be split into diploid tumors or near-diploid tumors on the one hand and over-diploid tumors in the other hand.

The inventors have detected near-diploid tumor genomes in more than 75% of the cases with BRCA1 inactivation (by mutation or by promoter methylation). Thus, the methods, systems, etc. of the invention can be used to detect HR deficiency in tumors found to be diploid or near-diploid tumors (e.g., in high grade breast carcinoma).

Typically, a tumor or tumor cell is deemed to be "diploid or near-diploid" if the genome of said tumor or cell carries on average less than 50 chromosomes and/or if it has a DNA index close to 1. Typically, a tumor or tumor cell is considered as "over-diploid" if its genome carries more than or equal to 50 chromosomes and/or has a DNA index higher than 1.2.

As used herein, the term "DNA index" represents the ratio of DNA content of the tumor cell and DNA content of a normal cell.

The skilled person can evaluate the ploidy of a tumor sample according to any standard technique in the art. Suitable techniques for evaluating ploidy can include, but are not limited to, measuring the amount of DNA per cell, by example by Fluorescence Activated Cell Sorting. In this technique, DNA is labeled by incorporation of an intercalating agent such as ethidium bromide or DAPI. The cells are then sorted according to the fluorescence intensity, which is proportional to the amount of DNA in each cell.

A suitable technique for evaluating ploidy can also include karyotyping. Conventional karyotypes can be obtained by staining the chromosomes (with stains such as Giemsa) and counting the number of chromosomes of each type in a cell.

A suitable technique for evaluating ploidy can also include virtual karyotyping using arrays such as array-CGH or Single Nucleotide Polymorphism array (SNP array). The arrays themselves can be genome-wide (probes distributed over the entire genome) or targeted (probes for genomic regions known to be involved in a specific disease) or a combination of both. Further, arrays used for karyotyping may use non-polymorphic probes, polymorphic probes (e.g., SNP-containing), or a combination of both. Non-polymorphic probes can provide only copy number information, while SNP arrays can provide both copy number and loss-of-heterozygosity (LOH) status in one assay. Commercially available oligonucleotide SNP arrays can be solid phase (Affymetrix, Santa Clara, Calif., USA) or bead-based (Illumina, San Diego, Calif., USA). Despite the diversity of platforms, ultimately they all use genomic DNA from disrupted cells to recreate a high resolution karyotype in silico. The end product does not yet have a consistent name, and has been called virtual karyotyping, digital karyotyping, molecular allelokaryotyping, and molecular karyotyping. Other terms used to describe the arrays used for karyotyping include SOMA (SNP oligonucleotide microarrays) and CMA (chromosome microarray). A suitable technique for evaluating ploidy can also include Next Generation Sequencing. High throughput methods for sequence the genome or the complete coding region are available. Whole genome or exome deep sequencing approaches can in some embodiments generate copy number and allelic imbalance profiles similar to or even more precise than SNP arrays.

According to one embodiment of the invention, the step of evaluating the ploidy of the tumor sample is carried out by a technique selected from the group consisting of FACS, karyotyping, and SNP array.

In one embodiment, both the step of evaluating the ploidy and the step of quantifying the number of large-scale rearrangement are performed by SNP array.

In a preferred embodiment, both the step of evaluating the ploidy and the step of quantifying the number of large-scale rearrangement are performed by SNP array, followed by GAP analysis.

Genome Alteration Print (GAP) is a bioinformatics tool which has been developed by Popova et al. (Genome Biology, 2009, 10:R128) for automatic detection of absolute segmental copy numbers and genotype status in complex cancer genome profiles measured with SNP-array. This method performs well even for poor-quality data, low tumor content and highly rearranged tumor genomes.

Rearrangement Comparisons

In one embodiment of the invention, the method comprises the step of comparing the number of rearrangements (e.g., LSTs) to a reference, and diagnosing HR deficiency in a cell having a number of rearrangements resulting in segments of at least 3 megabases (or at least 4, 5, 6, 7, 8, 9, 10, 11, 12, 13, 14, 15, 16, 17, 18, 19 or 20) greater than said reference.

Typically, the reference can have different values. Thus, in a preferred embodiment, the method comprises the step comparing the number of rearrangements (e.g., LSTs) in the genomic DNA to a reference, wherein said reference has a first value (reference1) and wherein said reference has a second value (reference2).

Typically, reference1 (as determined using segments at least 3, 4, 5, 6, 7, 8, 9, 10, 11, 12, 13, 14, 15, 16, 17, 18, 19 or 20 megabases in size, reference value being dependent on the chosen segment size) can be 15 Large-Scale Transitions (LST) (e.g., per genome), or 16, 17, 18, 19 or 20 or more LST (e.g., per genome).

Typically, the value of reference1 may vary, depending on how the number of rearrangements or LSTs is defined. Hence, in one embodiment of the invention, reference 1 is defined as follows: if the number of LSTs is defined as the number of rearrangements resulting in segments of at least 6 megabases, reference1 may be 17, 18 or 19; if the number of LSTs is defined as the number of rearrangements resulting in segments of at least 7 megabases, reference1 may be 15, 16 or 17; if the number of LSTs is defined as the number of rearrangements resulting in segments of at least 8 megabases, reference1 may be 14; if the number of LSTs is defined as the number of rearrangements resulting in segments of at least 9 megabases, reference1 may be 11, 12, 13 or 14; if the number of LSTs is defined as the number of rearrangements resulting in segments of at least 10 megabases, reference1 may be 11.

Typically, reference2 (as determined using segments longer than 10 megabases, reference value being dependent on the chosen segment size) can be 20 Large-Scale Transitions (LST) (e.g., per genome), preferably 21, even more preferably 22, 23, 24 or 25 LST (e.g., per genome).

Typically, the value of reference2 may vary, depending on how the number of rearrangements or LSTs is defined. Hence, in one embodiment of the invention, reference 2 is defined as follows: if the number of LSTs is defined as the number of rearrangements resulting in segments of at least 6 megabases, reference1 may be 32; if the number of LSTs is defined as the number of rearrangements resulting in segments of at least 7 megabases, reference1 may be 27, 28 or 29; if the number of LSTs is defined as the number of rearrangements resulting in segments of at least 8 megabases, reference1 may be 26; if the number of LSTs is defined as the number of rearrangements resulting in segments of at least 9 megabases, reference1 may be 19, 20, 21, 22, 23, 24 or 25; if the number of LSTs is defined as the number of rearrangements resulting in segments of at least 10 megabases, reference1 may be 18, 19, 20, 21, 22.

Optimum references may depend on the size of the LSTs in order to arrive at optimal specificity and sensitivity according to the tumor type. For example, optimum references for breast carcinoma may include 7/17/29, 8/14/26, 9/14/29 or 10/11/22, whereas optimum reference in ovarian carcinoma may include 6/19/32 or 7/17/29 (LST number/ reference1/reference2).

Indeed, the inventors have developed a 2-step process for detecting HR deficiency by classifying patients according to the number of large-scale transitions in the tumor genome (or optionally according to the ploidy of the tumor).

The invention therefore relates to a method comprising the steps of: determining the ploidy of the tumor; and comparing the number of rearrangements (e.g., LSTs) to a reference, wherein a number of rearrangements resulting in segments of at least 3 megabases superior to said reference is indicative of HR deficiency.

Advantageously, the method according to the invention is able to detect deficiency in the HR pathway with good specificity (few false positives) and good sensitivity (few false negatives).

Methods for Predicting the Efficacy of a Treatment and Methods of Treatment

The method described above has several major and direct clinical applications.

Firstly, tumor genomic profiling can now be used as criteria for genetic testing and council. This is especially important in absence of familial context of tumor predisposition, a situation found in as much as half of mutation-carrier patients[53].

Secondly with the emerging therapeutic perspective exploiting HR defects by targeting complementary pathways (for instance, PARP inhibitors (PARPi)[13], and alkylating agents, which provoke DNA damage), the question of efficient predictive markers of BRCAness or HR deficiency becomes important[16]. The disappointing efficiency of PARPi in unselected BLC/TNBC[54] supports the necessity to better stratify patients, which could be easily implemented using this SNP-array based marker.

Because it is possible to predict whether a given patient suffers from a cancer which is associated with deficiency in the DNA homologous recombination pathway, it is also possible to select the appropriate therapy for said patient.

As described herein, patients having cancer cells identified as having a genomic DNA rearrangement (e.g., LSTs) can be classified as being likely to respond to a particular cancer treatment regimen. For example, patients having cancer cells with a genome containing a genomic DNA rearrangement can be classified, as being likely to respond to a cancer treatment regimen that includes the use of a DNA damaging agent, a synthetic lethality agent (e.g., a PARP inhibitor), radiation, or a combination thereof. Preferably, the patients are treatment naïve patients. Examples of DNA damaging agents include, without limitation, platinum-based chemotherapy drugs (e.g., cisplatin, carboplatin, oxaliplatin, and picoplatin), anthracyclines (e.g., epirubicin and doxorubicin), topoisomerase I inhibitors (e.g., campothecin, topotecan, and irinotecan), DNA crosslinkers such as mitomycin C, and triazene compounds (e.g., dacarbazine and temozolomide). Synthetic lethality therapeutic approaches typically involve administering an agent that inhibits at least one critical component of a biological pathway that is especially important to a particular tumor cell's survival. For example, when a tumor cell has a deficient homologous repair pathway (e.g., as determined according to the present invention), inhibitors of poly ADP ribose polymerase (or platinum drugs, double strand break repair inhibitors, etc.) can be especially potent against such tumors because two pathways critical to survival become obstructed (one biologically, e.g., by BRCA1 mutation, and the other synthetically, e.g., by administration of a pathway drug). Synthetic lethality approaches to cancer therapy are described in, e.g., O'Brien et al., *Converting cancer mutations into therapeutic opportunities*, EMBO MOL. MED. (2009) 1:297-299. Examples of synthetic lethality agents include, without limitation, PARP inhibitors or double strand break repair inhibitors in homologous repair-deficient tumor cells, PARP inhibitors in PTEN-deficient tumor cells, methotrexate in MSH2-deficient tumor cells, etc. Examples of PARP inhibitors include, without limitation, olaparib, iniparib, and veliparib. Examples of double strand break repair inhibitors include, without limitation, KU55933 (ATM inhibitor) and NU7441 (DNA-PKcs inhibitor). Examples of information that can be used in addition to a positive genomic DNA rearrangement to base a classification of being likely to respond to a particular cancer treatment regimen include, without limitation, previous treatment results, germline or somatic DNA mutations, gene or protein expression profiling (e.g., ER/PR/HER2 status, PSA levels), tumor histology (e.g., adenocarcinoma, squamous cell carcinoma, papillary serous carcinoma, mucinous carcinoma, invasive ductal carcinoma, ductal carcinoma in situ (non-invasive), etc.), disease stage, tumor or cancer grade (e.g., well, moderately, or poorly differentiated (e.g., Gleason, modified Bloom Richardson), etc.), number of previous courses of treatment, etc. Increased likelihood of responding can refer, for example, to an increased likelihood of response as compared to any reference patient/population, or an increased likelihood of responding as compared to a specific reference patient/population.

Once classified as being likely to respond to a particular cancer treatment regimen (e.g., a cancer treatment regimen that includes the use of a DNA damaging agent, a PARP inhibitor, radiation, or a combination thereof), the cancer patient can be treated with such a cancer treatment regimen. In some embodiments, the patients are treatment naïve patients. Any appropriate method for treating the cancer at issue can be used to treat a cancer patient identified as having cancer cells having a genomic DNA rearrangement. For example, platinum-based chemotherapy drugs or a combination of platinum-based chemotherapy drugs can be used to treat cancer as described elsewhere (see, e.g., U.S. Pat. Nos. 3,892,790, 3,904,663, 7,759,510, 7,759,488 and 7,754, 684. In some cases, anthracyclines or a combination of anthracyclines can be used to treat cancer as described elsewhere (see, e.g., U.S. Pat. Nos. 3,590,028, 4,138,480, 4,950,738, 6,087,340, 7,868,040, and 7,485,707. In some cases, topoisomerase I inhibitors or a combination of topoisomerase I inhibitors can be used to treat cancer as described elsewhere (see, e.g., U.S. Pat. Nos. 5,633,016 and 6,403, 563. In some cases, PARP inhibitors or a combination of PARP inhibitors can be used to treat cancer as described elsewhere (see, e.g., U.S. Pat. Nos. 5,177,075, 7,915,280, and 7,351,701. In some cases, radiation can be used to treat cancer as described elsewhere (see, e.g., U.S. Pat. No. 5,295,944). In some cases, a combination comprising different agents (e.g., a combination comprising any of platinum-based chemotherapy drugs, anthracyclines, topoisomerase I inhibitors, and/or PARP inhibitors) with or without radiation treatments can be used to treat cancer. In some cases, a combination treatment may comprise any of the above agents or treatments (e.g., a DNA damaging agent, a PARP inhibitor, radiation, or a combination thereof) together with another agent or treatment—e.g., a taxane agent (e.g., doxetaxel, paclitaxel, abraxane), a growth factor or growth factor receptor inhibitor (e.g., erlotinib, gefitinib, lapatinib, sunitinib, bevacizumab, cetuximab, trastuzumab, panitumumab), and/or an antimetabolite (e.g., 5-flourouracil, methotrexate).

In some cases, patients identified as having cancer cells with a genome lacking a genomic DNA rearrangement (e.g., LSTs) can be classified, based at least in part on a negative genomic DNA rearrangement status, as being less likely to respond to a treatment regimen that includes a DNA damaging agent, a PARP inhibitor, radiation, or a combination thereof. In turn, such a patient can be classified as likely to respond to a cancer treatment regimen that includes the use of one or more cancer treatment agents not associated with HR, such as a taxane agent (e.g., doxetaxel, paclitaxel, abraxane), a growth factor or growth factor receptor inhibitor (e.g., erlotinib, gefitinib, lapatinib, sunitinib, bevacizumab, cetuximab, trastuzumab, panitumumab), and/or an antimetabolite agent (e.g., 5-flourouracil, methotrexate). In some embodiments, the patients are treatment naïve patients. Once classified as being likely to respond to a particular cancer treatment regimen (e.g., a cancer treatment regimen that includes the use of a cancer treatment agent not associated with HR), the cancer patient can be treated with such a cancer treatment regimen. Any appropriate method for the cancer being treated can be used to treat a cancer patient identified as having cancer cells having a negative genomic DNA rearrangement status. Examples of information that can be used in addition to a negative genomic DNA rearrangement status to base a classification of being likely to respond to a particular cancer treatment regimen include, without limitation, previous treatment results, germline or somatic DNA mutations, gene or protein expression profiling (e.g., ER/PR/HER2 status, PSA levels), tumor histology (e.g., adenocarcinoma, squamous cell carcinoma, papillary serous carcinoma, mucinous carcinoma, invasive ductal carcinoma, ductal carcinoma in situ (non-invasive), etc.), disease stage, tumor or cancer grade (e.g., well, moderately, or poorly differentiated (e.g., Gleason, modified Bloom Richardson), etc.), number of previous courses of treatment, etc. Increased likelihood of responding can refer, for example, to an increased likelihood of response as compared to any reference patient/population, or an increased likelihood of responding as compared to a specific reference patient/population.

In one aspect, the invention relates to a method for treating cancer in a patient, comprising the steps of: quantifying the number of rearrangements (e.g., LSTs) in the genomic DNA of a tumor sample obtained from said patient, wherein the number of rearrangements corresponds to the number (e.g., per genome), of breakpoints resulting in segments of at least 3 megabases, preferably at least 4 megabases, even more preferably at least 5, 6, 7, 8 9, 10, 11 12, 13, 14, 15, 16, 17, 18, 19 or 20 megabases; comparing said number of rearrangements to a predetermined reference; and administering a therapeutically effective amount of a PARP inhibitor and/or an alkylating agent, if said patient has a number of rearrangements superior to said reference.

Said reference may also differ, depending on the minimum size of the segments taken into account for determining the number of rearrangements (or "LSTs").

By a "therapeutically effective amount" of an agent which increases the level of deoxyuridine is meant a sufficient amount to treat cancer, at a reasonable benefit/risk ratio applicable to any medical treatment. It will be understood, however, that the total daily usage of an agent which increases the level of deoxyuridine will be decided by the attending physician within the scope of sound medical judgment. The specific therapeutically effective dose for any particular subject in need thereof will depend upon a variety of factors including other cancer predisposition markers, lifestyle-related risk factors and the activity of the specific agent which increases the level of deoxyuridine to be used, the age, body weight, general health, sex and diet of the subject, the time of administration, route of administration, the duration of the treatment; drugs used in combination or coincidental with the and like factors well known in the medical arts.

Once treated for a particular period of time (e.g., between one to six months), the patient can be assessed to determine whether or not the treatment regimen has an effect. If a beneficial effect is detected, the patient can continue with the same or a similar cancer treatment regimen. If a minimal or no beneficial effect is detected, then adjustments to the cancer treatment regimen can be made. For example, the dose, frequency of administration, or duration of treatment can be increased. In some cases, additional anti-cancer agents can be added to the treatment regimen or a particular anti-cancer agent can be replaced with one or more different anti-cancer agents. The patient being treated can continue to be monitored as appropriate, and changes can be made to the cancer treatment regimen as appropriate.

It is believed that a treatment which causes double strand breaks in the DNA (such as alkylating agents) or a treatment which inhibits the alternative DNA repair pathway (such as PARPi) will be more efficient if the tumor is deficient for the HR pathway.

In addition, the inventors have shown that the number of LSTs is a good predictor or response to treatment with an alkylating agent such as cisplatin (see Example 3).

Therefore, another aspect of the present invention concerns a method for predicting the efficacy of a treatment in a patient suffering from cancer, wherein said treatment comprises a PARPi and/or an alkylating agent, and wherein said method comprises the step consisting of predicting deficiency on the HR pathway as described above.

The invention also relates to a PARPi and/or an alkylating agent for use in a method for treating cancer in patient wherein said cancer is linked to deficiency in the HR pathway.

As used herein the term "PARP inhibitor" has its general meaning in the art. It refers to a compound which is capable of inhibiting the activity of the enzyme polyADP ribose polymerase (PARP), a protein that is important for repairing single-strand breaks ('nicks' in the DNA). If such nicks persist unrepaired until DNA is replicated (which must precede cell division), then the replication itself will cause double strand breaks to form. Drugs that inhibit PARP cause multiple double strand breaks to form in this way, and in tumors with BRCA1, BRCA2 or PALB2 mutations these double strand breaks cannot be efficiently repaired, leading to the death of the cells.

Typically, the PARP inhibitor according to the invention can be selected from the group consisting of iniparib, olaparib, rocaparib, CEP 9722, MK 4827, BMN-673, and 3-aminobenzamide.

As used herein, the term "alkylating agent" or "alkylating antineoplastic agent" has its general meaning in the art. It refers to compounds which attach an alkyl group to DNA. Typically, the alkylating agent according to the invention can be selected from platinum complexes such as cisplatin, carboplatin and oxaliplatin, chlormethine, chlorambucil, melphalan, cyclophosphamide, ifosfamide, estramustine, carmustine, lomustine, fotemustine, streptozocin, busulfan, pipobroman, procarbazine, dacarbazine, thiotepa and temozolomide.

The invention also relates to a pharmaceutical composition comprising a PARP inhibitor and/or an alkylating agent for use in a method of treating cancer in a patient, wherein said cancer is linked to deficiency in the HR pathway.

In the pharmaceutical compositions of the present invention for oral, sublingual, subcutaneous, intramuscular, intravenous, transdermal, local or mucosal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and oral administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

In one embodiment, the PARP inhibitor and/or alkylating agent is administered in combination with another active agent.

Typically, the PARP inhibitor and the other active agent can be formulated separately. Alternatively, they can be formulated together in a pharmaceutical composition.

In one embodiment, the PARP inhibitor and/or alkylating agent is administered to a patient who is subjected to radiation therapy and/or surgery in order to remove the tumor.

As described herein, the present invention also provides methods for assessing patients for cells (e.g., cancer cells) having a genome containing a genomic DNA rearrangement (e.g., an LST). In some embodiments, the patients are treatment naïve patients. For example, one or more clinicians or medical professionals can determine if a patient contains cancer cells having a genome containing a genomic DNA rearrangement. In some cases, one or more clinicians or medical professionals can determine if a patient contains cancer cells having a genome containing a genomic DNA rearrangement by obtaining a cancer cell sample from the patient and assessing the genome of cancer cells of the cancer cell sample to determine the presence or absence of a genomic DNA rearrangement as described herein.

In some cases, one or more clinicians or medical professionals can obtain a cancer cell sample from a patient and provide that sample to a testing laboratory having the ability to assess the genome of cancer cells of the cancer cell sample to provide an indication about the presence or absence of a genomic DNA rearrangement as described herein. In some embodiments, the patients are treatment naïve patients. In such cases, the one or more clinicians or medical professionals can determine if a patient contains cancer cells having a genome containing a genomic DNA rearrangement by receiving information about the presence or absence of a genomic DNA rearrangement directly or indirectly from the testing laboratory. For example, a testing laboratory, after assessing the genome of cancer cells for presence or absence of a genomic DNA rearrangement as described herein, can provide a clinician or medical professional with, or access to, a written, electronic, or oral report or medical record that provides an indication about the presence or absence of a genomic DNA rearrangement for a particular patient being assessed. Such a written, electronic, or oral report or medical record can allow the one or more clinicians or medical professionals to determine if a particular patient being assessed contains cancer cells having a genome containing a genomic DNA rearrangement.

Once a clinician or medical professional or group of clinicians or medical professionals determines that a particular patient being assessed contains cancer cells having a genome containing a genomic DNA rearrangement (e.g., an LSTs), the clinician or medical professional (or group) can classify that patient as having cancer cells whose genome contains the presence of a genomic DNA rearrangement. In some embodiments, the patients are treatment naïve patients. In some cases, a clinician or medical professional or group of clinicians or medical professionals can diagnose a patient determined to have cancer cells whose genome contains the presence of a genomic DNA rearrangement as having cancer cells likely to be deficient in HR. Such a diagnosis can be based solely on a determination that a particular patient being assessed contains cancer cells having a genome containing a genomic DNA rearrangement or can be based at least in part on a determination that a particular patient being assessed contains cancer cells having a genome containing a genomic DNA rearrangement. For example, a patient determined to have cancer cells whose genome contains the presence of a genomic DNA rearrangement can be diagnosed as likely to be deficient in HR based on the combination of a positive a genomic DNA rearrangement status and deficient status in one or more tumor suppressor genes (e.g., BRCA1/2, RAD51C), a family history of cancer, or the presence of behavioral risk factors (e.g., smoking).

In some cases, a clinician or medical professional or group of clinicians or medical professionals can diagnose a patient determined to have cancer cells whose genome contains the presence of a genomic DNA rearrangement (e.g., an LST) as having cancer cells likely to contain genetic mutations in one or more genes in the HR pathway. In some embodiments, the patients are treatment naïve patients. Such a diagnosis can be based solely on a determination that a particular patient being assessed contains cancer cells having a genome containing a genomic DNA rearrangement or can be based at least in part on a determination that a particular patient being assessed contains cancer cells having a genome containing a genomic DNA rearrangement. For example, a patient determined to have cancer cells whose genome contains the presence of a genomic DNA rearrangement can be diagnosed as having cancer cells likely to contain genetic mutations in one or more genes in the HR pathway based on the combination of a positive a genomic DNA rearrangement status and a family history of cancer, or the presence of behavioral risk factors (e.g., smoking).

In some cases, a clinician or medical professional or group of clinicians or medical professionals can diagnose a patient determined to have cancer cells whose genome contains the presence of a genomic DNA rearrangement (e.g., an LST) as having cancer cells likely to respond to a particular cancer treatment regimen. In some embodiments, the patients are treatment naïve patients. Such a diagnosis can be based solely on a determination that a particular patient being assessed contains cancer cells having a genome containing a genomic DNA rearrangement or can be based at least in part on a determination that a particular patient being assessed contains cancer cells having a genome containing a genomic DNA rearrangement. For example, a patient determined to have cancer cells whose genome contains the presence of a genomic DNA rearrangement can be diagnosed as being likely to respond to a particular cancer treatment regimen based on the combination of the presence of genomic DNA rearrangement and deficient status in one or more tumor suppressor genes (e.g., BRCA1/2, RAD51), a family history of cancer, or the presence of behavioral risk factors (e.g., smoking). As described herein, a patient determined to have cancer cells whose genome contains the presence of a genomic DNA rearrangement can be diagnosed as likely to respond to a cancer treatment regimen that includes the use of a platinum-based chemotherapy drug such as cisplatin, carboplatin, oxaliplatin, or picoplatin, an anthracycline such as epirubicin or doxorubicin, a topoisomerase I inhibitor such as campothecin, topotecan, or irinotecan, a PARP inhibitor, radiation, a combination thereof, or a combination of any of the preceding with another anti-cancer agent. In some embodiments, the patients are treatment naïve patients. Increased likelihood of responding can refer, for example, to an increased likelihood of response as compared to any reference patient/population, or an increased likelihood of responding as compared to a specific reference patient/population.

Once a clinician or medical professional or group of clinicians or medical professionals determines that a particular patient being assessed contains cancer cells having a genome lacking a genomic DNA rearrangement (e.g., an LST), the clinician or medical professional (or group) can classify that patient as having cancer cells whose genome contains an absence of a genomic DNA rearrangement. In some embodiments, the patients are treatment naïve patients. In some cases, a clinician or medical professional or group of clinicians or medical professionals can diagnose a patient determined to have cancer cells containing a genome that lacks the presence of a genomic DNA rearrangement as having cancer cells likely to have functional HR. In some cases, a clinician or medical professional or group of clinicians or medical professionals can diagnose a patient determined to have cancer cells containing a genome that lacks the presence of a genomic DNA rearrangement as having cancer cells that do not likely contain genetic mutations in one or more genes in the HR pathway. In some cases, a clinician or medical professional or group of clinicians or medical professionals can diagnose a patient determined to have cancer cells containing a genome that lacks the presence of a genomic DNA rearrangement or contains an increased number of genomic DNA rearrangements that cover the whole chromosome as having cancer cells that are less likely to respond to a platinum-based chemotherapy drug such as cisplatin, carboplatin, oxalaplatin, or picoplatin, an anthracycline such as epirubincin or doxorubicin, a topoisomerase I inhibitor such as campothecin, topotecan, or irinotecan, a PARP inhibitor, or radiation and/or more likely to respond to a cancer treatment regimen that includes the use of a cancer treatment agent not associated with HR such as one or more taxane agents, growth factor or growth factor receptor inhibitors, anti-metabolite agents, etc. In some embodiments, the patients are treatment naïve patients.

Increased likelihood of responding can refer, for example, to an increased likelihood of response as compared to any reference patient/population, or an increased likelihood of responding as compared to a specific reference patient/population.

As described herein, the present invention also provides methods for performing a diagnostic analysis of a nucleic acid sample (e.g., a genomic nucleic acid sample or amplified genomic nucleic acid sample) of a cancer patient to determine if cancer cells within the patient have a genome containing a genomic DNA rearrangement (e.g., an LST). In some embodiments, the patients are treatment naïve patients. For example, one or more laboratory technicians or laboratory professionals can detect the presence or absence of a genomic DNA rearrangement in the genome of cancer cells of the patient or the presence or absence of a genomic DNA rearrangement in the genome of cancer cells of the patient. In some cases, one or more laboratory technicians or laboratory professionals can detect the presence or absence of a genomic DNA rearrangement or the presence or absence of a genomic DNA rearrangement in the genome of cancer cells of the patient by (a) receiving a cancer cell sample obtained from the patient, receiving a genomic nucleic acid sample obtained from cancer cells obtained from the patient, or receiving an enriched and/or amplified genomic nucleic acid sample obtained from cancer cells obtained from the patient and (b) performing an analysis (e.g., a SNP array-based assay or a sequencing-based assay) using the received material to detect the presence or absence of a genomic DNA rearrangement. In some cases, one or more laboratory technicians or laboratory professionals can receive a sample to be analyzed (e.g., a cancer cell sample obtained from the patient, a genomic nucleic acid sample obtained from cancer cells obtained from the patient, or an enriched and/or amplified genomic nucleic acid sample obtained from cancer cells obtained from the patient) directly or indirectly from a clinician or medical professional. In some embodiments, the patients are treatment naïve patients.

Once a laboratory technician or laboratory professional or group of laboratory technicians or laboratory professionals detects the presence of a genomic DNA rearrangement (e.g., an LST) as described herein, the laboratory technician or laboratory professional (or group) can identify the patient whose cancer cells were detected as having a genomic DNA rearrangement as having cancer cells with a positive a genomic DNA rearrangement status. For example, one or more laboratory technicians or laboratory professionals can identify a patient having cancer cells that were detected to have a genomic DNA rearrangement as having cancer cells with a genomic DNA rearrangement by associating that a genomic DNA rearrangement or the result (or results or a summary of results) of the performed diagnostic analysis with the corresponding patient's name, medical record, symbolic/numerical identifier, or a combination thereof. In some cases, a laboratory technician or laboratory professional or group of laboratory technicians or laboratory professionals can identify a patient having cancer cells that were detected to have a genomic DNA rearrangement as having cancer cells potentially deficient in HR by associating the genomic DNA rearrangement, the potentially deficient in HR status, or the result (or results or a summary of results) of the performed diagnostic analysis with the corresponding patient's name, medical record, symbolic/numerical identifier, or a combination thereof. Such identification can be based solely on detecting the presence of a genomic DNA rearrangement or can be based at least in part on detecting the presence of a genomic DNA rearrangement.

For example, a laboratory technician or laboratory professional can identify a patient having cancer cells that were detected to have a genomic DNA rearrangement as having cancer cells potentially deficient in HR based on a combination of a genomic DNA rearrangement and the results of other genetic and biochemical tests performed at the testing laboratory. In some embodiments, the patients are treatment naïve patients.

In some cases, a laboratory technician or laboratory professional or group of laboratory technicians or laboratory professionals can identify a patient having cancer cells that were detected to have a genomic DNA rearrangement (e.g., an LST) as having cancer cells potentially containing a genetic mutation in one or more genes in the HR pathway by associating the genomic DNA rearrangement, the potential presence of a genetic mutation in one or more genes in the HR pathway, or the result (or results or a summary of results) of the performed diagnostic analysis with the corresponding patient's name, medical record, symbolic/numerical identifier, or a combination thereof. Such identification can be based solely on detecting the presence of a genomic DNA rearrangement or can be based at least in part on detecting the presence of a genomic DNA rearrangement. For example, a laboratory technician or laboratory professional can identify a patient having cancer cells that were detected to have a genomic DNA rearrangement as having cancer cells potentially containing a genetic mutation in one or more genes in the HR pathway based on a combination of a genomic DNA rearrangement and the results of other genetic and biochemical tests performed at the testing laboratory. In some embodiments, the patients are treatment naïve patients.

In some cases, a laboratory technician or laboratory professional or group of laboratory technicians or laboratory professionals can identify a patient having cancer cells that were detected to have a genomic DNA rearrangement (e.g., an LST) as having cancer cells likely to respond to a particular cancer treatment regimen by associating the a genomic DNA rearrangement, a potentially deficient HR status, a potential presence of a deficient status in one or more genes in the HR pathway, or the result (or results or a summary of results) of the performed diagnostic analysis with the corresponding patient's name, medical record, symbolic/numerical identifier, or a combination thereof. Such identification can be based solely on detecting the presence of a genomic DNA rearrangement or can be based at least in part on detecting the presence of a genomic DNA rearrangement. For example, a laboratory technician or laboratory professional can identify a patient having cancer cells that were detected to have a genomic DNA rearrangement as having cancer cells likely to respond to a particular cancer treatment regimen based on a combination of a genomic DNA rearrangement and the results of other genetic and biochemical tests performed at the testing laboratory. In some embodiments, the patients are treatment naïve patients. Increased likelihood of responding can refer, for example, to an increased likelihood of response as compared to any reference patient/population, or an increased likelihood of responding as compared to a specific reference patient/population.

Once a laboratory technician or laboratory professional or group of laboratory technicians or laboratory professionals detects the absence of a genomic DNA rearrangement (e.g., an LST), the laboratory technician or laboratory professional (or group) can identify the patient whose cancer cells were detected as lacking a genomic DNA rearrangement as having cancer cells with a negative a genomic DNA rearrangement status. For example, one or more laboratory technicians or laboratory professionals can identify a patient having cancer cells that were detected to lack a genomic DNA rearrangement as having cancer cells with a negative genomic DNA rearrangement status by associating that negative genomic DNA rearrangement status or the result (or results or a summary of results) of the performed diagnostic analysis with the corresponding patient's name, medical record, symbolic/numerical identifier, or a combination thereof. In some cases, a laboratory technician or laboratory professional or group of laboratory technicians or laboratory professionals can identify a patient having cancer cells that were detected to lack a genomic DNA rearrangement as having cancer cells with potentially intact HR by associating the negative genomic DNA rearrangement status, the potentially intact HR status, or the result (or results or a summary of results) of the performed diagnostic analysis with the corresponding patient's name, medical record, symbolic/numerical identifier, or a combination thereof. In some embodiments, the patients are treatment naïve patients.

In some cases, a laboratory technician or laboratory professional or group of laboratory technicians or laboratory professionals can identify a patient having cancer cells that were detected to lack a genomic DNA rearrangement (e.g., an LST) as having cancer cells with potentially intact genes of the HR pathway by associating the negative genomic DNA rearrangement status, the potential absence of genetic mutations in genes of the HR pathway, or the result (or results or a summary of results) of the performed diagnostic analysis with the corresponding patient's name, medical record, symbolic/numerical identifier, or a combination thereof. In some embodiments, the patients are treatment naïve patients.

In some cases, a laboratory technician or laboratory professional or group of laboratory technicians or laboratory professionals can identify a patient having cancer cells that were detected to lack a genomic DNA rearrangement (e.g., an LST) as having cancer cells as less likely to respond to one particular treatment (e.g., a platinum-based chemotherapy drug such as cisplatin, carboplatin, oxalaplatin, or picoplatin, an anthracycline such as epirubincin or doxorubicin, a topoisomerase I inhibitor such as campothecin, topotecan, or irinotecan, a PARP inhibitor such as iniparib, olaparib, or velapirib, or radiation) and/or more likely to respond to a particular cancer treatment regimen (e.g., a cancer treatment regimen that includes the use of a cancer treatment agent not associated with HR) by associating the negative genomic DNA rearrangement status, a potentially intact HR status, a potential absence of genetic mutations in genes of the HR pathway, or the result (or results or a summary of results) of the performed diagnostic analysis with the corresponding patient's name, medical record, symbolic/numerical identifier, or a combination thereof. In some embodiments, the patients are treatment naïve patients. Increased likelihood of responding can refer, for example, to an increased likelihood of response as compared to any reference patient/population, or an increased likelihood of responding as compared to a specific reference patient/population.

Once a laboratory technician or laboratory professional or group of laboratory technicians or laboratory professionals detects the presence of a genomic DNA rearrangement (e.g., an LST), the laboratory technician or laboratory professional (or group) can identify the patient whose cancer cells were detected as having a genomic DNA rearrangement that covers the whole chromosome as likely having cancer cells with an intact BRCA1, BRCA2 and/or RAD51C status, or intact HR pathway. For example, one or more laboratory technicians or laboratory professionals can identify a patient having cancer cells that were detected to have a genomic DNA rearrangement as likely having cancer cells with an intact BRCA1 and BRCA2 status by associating the presence of an increased number genomic DNA rearrangements that cover the whole chromosome or the result (or results or a summary of results) of the performed diagnostic analysis with the corresponding patient's name, medical record, symbolic/numerical identifier, or a combination thereof. In some embodiments, the patients are treatment naïve patients.

The results of any analyses according to the invention will often be communicated to physicians, genetic counselors and/or patients (or other interested parties such as researchers) in a transmittable form that can be communicated or transmitted to any of the above parties. Such a form can vary and can be tangible or intangible. The results can be embodied in descriptive statements, diagrams, photographs, charts, images or any other visual forms. For example, graphs or diagrams showing genotype or a genomic DNA rearrangement (or HRD status) information can be used in explaining the results. The statements and visual forms can be recorded on a tangible medium such as papers, computer readable media such as floppy disks, compact disks, flash memory, etc., or in an intangible medium, e.g., an electronic medium in the form of email or website on internet or intranet. In addition, results can also be recorded in a sound form and transmitted through any suitable medium, e.g., analog or digital cable lines, fiber optic cables, etc., via telephone, facsimile, wireless mobile phone, internet phone and the like.

Thus, the information and data on a test result can be produced anywhere in the world and transmitted to a different location. As an illustrative example, when an assay is conducted outside the United States, the information and data on a test result may be generated, cast in a transmittable form as described above, and then imported into the United States. Accordingly, the present invention also encompasses a method for producing a transmittable form of information on a genomic DNA rearrangement for at least one patient sample. The method comprises the steps of (1) determining a genomic DNA rearrangement according to methods of the present invention; and (2) embodying the result of the determining step in a transmittable form. The transmittable form is a product of such a method.

By way of illustration, but not limitation, one embodiment described in this document is a method of predicting a cancer patient's response to a cancer treatment regimen comprising a DNA damaging agent, an anthracycline, a topoisomerase I inhibitor, radiation, and/or a PARP inhibitor, said method comprising: (1) detecting a number of rearrangements (e.g., LSTs) in the genomic DNA of a tumor sample obtained from said patient, wherein the number of rearrangements corresponds to the number (e.g., per genome), of breakpoints resulting in segments of at least 3, 4, 5, 6, 7, 8, 9, 10, 11, 12, 13, 14, 15, 16, 17, 18, 19, or 20 megabases; and (2) correlating said total number that is greater than a reference number with an increased likelihood that said cancer patient will respond to said cancer treatment regimen. According to the preceding paragraph, this description of this embodiment is understood to include a description of two related embodiments, e.g., a method of predicting a cancer patient's response to a cancer treatment regimen comprising a DNA damaging agent, an anthracycline, a topoisomerase I inhibitor, radiation, and/or a PARP inhibitor, said method comprising: (1) detecting a number of rearrangements in the genomic DNA of a tumor sample obtained from said patient, wherein the number of rearrangements corresponds to the number (e.g., per genome), of breakpoints resulting in segments of at least 3, 4, 5, 6, 7, 8, 9, 10, 11, 12, 13, 14, 15, 16, 17, 18, 19, or 20 megabases; and (2)(a) concluding that said patient has an increased likelihood that said cancer patient will respond to said cancer treatment regimen based at least in part on a total number that is greater than a reference number; or (2)(b) communicating that said patient has an increased likelihood that said cancer patient will respond to said cancer treatment regimen based at least in part on a total number that is greater than a reference number.

In each embodiment described in this document involving correlating a particular assay or analysis output (e.g., total number of rearrangements greater than a reference number, etc.) to some likelihood (e.g., increased, not increased, decreased, etc.) of some clinical feature (e.g., response to a particular treatment, cancer-specific death, etc.), or additionally or alternatively concluding or communicating such clinical feature based at least in part on such particular assay or analysis output, such correlating, concluding or communicating may comprise assigning a risk or likelihood of the clinical feature occurring based at least in part on the particular assay or analysis output. In some embodiments, such risk is a percentage probability of the event or outcome occurring. In some embodiments, the patient is assigned to a risk group (e.g., low risk, intermediate risk, high risk, etc.). In some embodiments "low risk" is any percentage probability below 5%, 10%, 15%, 20%, 25%, 30%, 35%, 40%, 45%, or 50%. In some embodiments "intermediate risk" is any percentage probability above 5%, 10%, 15%, 20%, 25%, 30%, 35%, 40%, 45%, or 50% and below 15%, 20%, 25%, 30%, 35%, 40%, 45%, 50%, 55%, 60%, 65%, 70%, or 75%. In some embodiments "high risk" is any percentage probability above 25%, 30%, 35%, 40%, 45%, 50%, 55%, 60%, 65%, 70%, 75%, 80%, 85%, 90%, 95%, or 99%.

As used herein, "communicating" a particular piece of information means to make such information known to another person or transfer such information to a thing (e.g., a computer). In some methods of the invention, a patient's prognosis or likelihood of response to a particular treatment is communicated. In some embodiments, the information used to arrive at such a prognosis or response prediction (e.g., a genomic DNA rearrangement according to the present invention, etc.) is communicated. This communication may be auditory (e.g., verbal), visual (e.g., written), electronic (e.g., data transferred from one computer system to another), etc. In some embodiments, communicating a cancer classification (e.g., prognosis, likelihood of response, appropriate treatment, etc.) comprises generating a report that communicates the cancer classification. In some embodiments the report is a paper report, an auditory report, or an electronic record. In some embodiments the report is displayed and/or stored on a computing device (e.g., handheld device, desktop computer, smart device, website, etc.). In some embodiments the cancer classification is communicated to a physician (e.g., a report communicating the classification is provided to the physician). In some embodiments the cancer classification is communicated to a patient (e.g., a report communicating the classification is provided to the patient). Communicating a cancer classification can also be accomplished by transferring information (e.g., data) embodying the classification to a server computer and allowing an intermediary or end-user to access such information (e.g., by viewing the information as displayed from the server, by downloading the information in the form of one or more files transferred from the server to the intermediary or end-user's device, etc.).

Wherever an embodiment of the invention comprises concluding some fact (e.g., a patient's prognosis or a patient's likelihood of response to a particular treatment regimen), this may include in some embodiments a computer program concluding such fact, typically after performing an algorithm that applies information on rearrangements according to the present invention.

In each embodiment described herein involving a number of genomic DNA rearrangements (e.g., LSTs), the present invention encompasses a related embodiment involving a test value or score (e.g., HRD score, etc.) derived from, incorporating, and/or, at least to some degree, reflecting such number or length. In other words, the bare rearrangement numbers need not be used in the various methods, systems, etc. of the invention; a test value or score derived from such numbers may be used. For example, one embodiment of the invention provides a method of treating cancer in a patient, comprising: (1) detecting a number of rearrangements in the genomic DNA of a tumor sample obtained from said patient, wherein the number of rearrangements corresponds to the number (e.g., per genome), of breakpoints resulting in segments of at least 3, 4, 5, 6, 7, 8, 9, 10, 11, 12, 13, 14, 15, 16, 17, 18, 19 or 20 megabases; (2) providing a test value derived from the number of said rearrangements; (3) comparing said test value to one or more reference values derived from the number of said rearrangements in a reference population (e.g., mean, median, terciles, quartiles, quintiles, etc.); and (4)(a) administering to said patient an anti-cancer drug, or recommending or prescribing or initiating a treatment regimen comprising chemotherapy and/or a synthetic lethality agent based at least in part on said comparing step revealing that the test value is greater (e.g., at least 2-, 3-, 4-, 5-, 6-, 7-, 8-, 9-, or 10-fold greater; at least 1, 2, 3, 4, 5, 6, 7, 8, 9, or 10 standard deviations greater) than at least one said reference value; or (4)(b) recommending or prescribing or initiating a treatment regimen not comprising chemotherapy and/or a synthetic lethality agent based at least in part on said comparing step revealing that the test value is not greater (e.g., not more than 2-, 3-, 4-, 5-, 6-, 7-, 8-, 9-, or 10-fold greater; not more than 1, 2, 3, 4, 5, 6, 7, 8, 9, or 10 standard deviations greater) than at least one said reference value. The invention encompasses, mutatis mutandis, corresponding embodiments where the test value or score is used to determine the patient's prognosis, the patient's likelihood of response to a particular treatment regimen, the patient's or patient's sample's likelihood of having a BRCA1, BRCA2, RAD51C or HR deficiency, etc.

Figure 8:
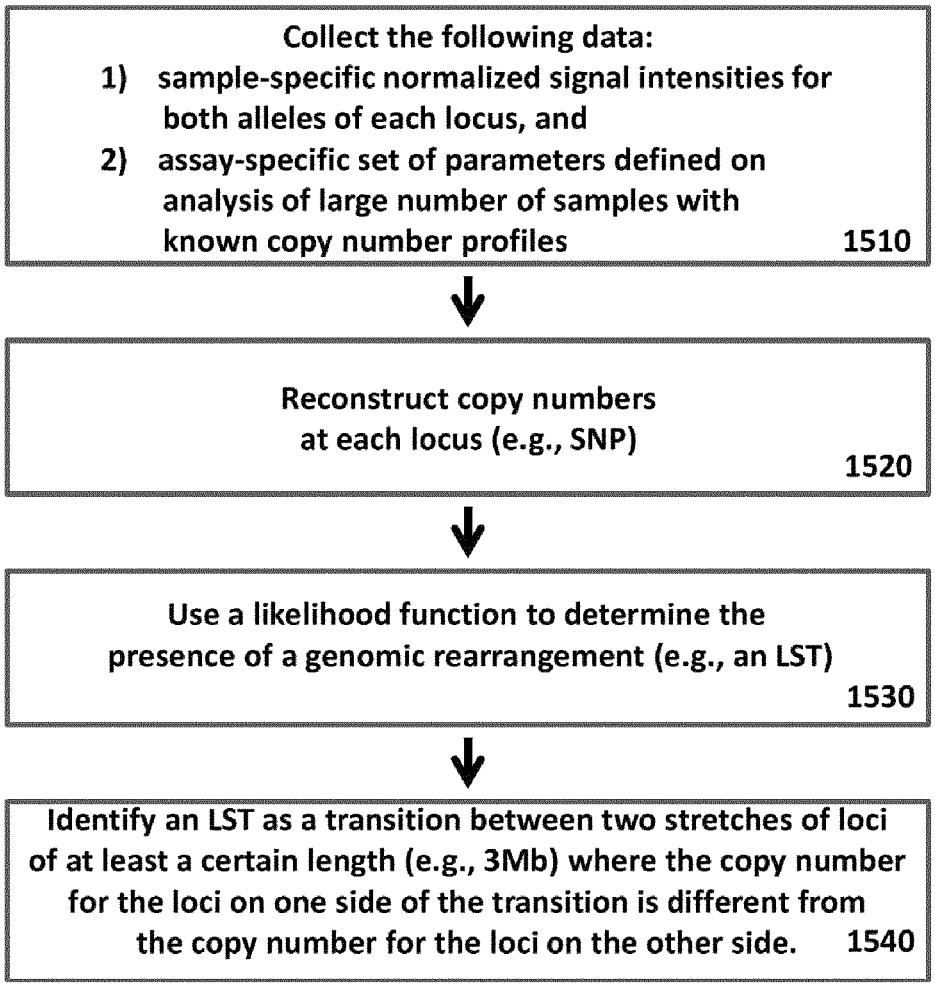
FIG. 8. Computational flow chart. Illustrated is a flow chart of an example computational process for identifying genomic DNA rearrangements.

The present invention provides computing systems. FIG. 8 shows an exemplary process by which a computing system (or a computer program (e.g., software) containing computer-executable instructions) can identify a genomic DNA rearrangement from genotype data as described herein. The process begins at box 1500, where the following data are collected by the computing system; (1) sample-specific normalized signal intensities for both alleles of each locus and (2) assay-specific (specific for different SNP arrays and for sequence based approach) set of parameters defined based on analysis of large number of samples with known ASCN profiles. As described herein, any appropriate assay such as a SNP array-based assay or sequencing-based assay can be used to assess loci along a chromosome for rearrangements. In some cases, a system including a signal detector and a computer can be used to collect data (e.g., fluorescent signals or sequencing results) regarding the nature of the plurality of loci (e.g., sample-specific normalized signal intensities for both alleles of each locus). At box 1510, allele specific copy numbers (ASCN) are reconstructed at each locus (e.g., each SNP). ASCNs are the numbers of copies of both paternal and maternal alleles. At box 1530, a likelihood function is used to determine whether a genomic DNA rearrangement is present. This can be conceptually analogous to a previously described algorithm designed to reconstruct total copy number (rather than ASCN) at each locus (e.g., SNP). See International Application No. PCT/US2011/026098 to Abkevich et al. The likelihood function can be maximized over ASCN of all loci, level of contamination with benign tissue, total copy number averaged over the whole genome, and sample specific noise level. At box 1540, a genomic DNA rearrangement is determined with one of the ASCNs (paternal or maternal) being zero. In some embodiments, the computer process further comprises a step of inquiring or determining whether a patient is treatment naïve.

Figure 9:
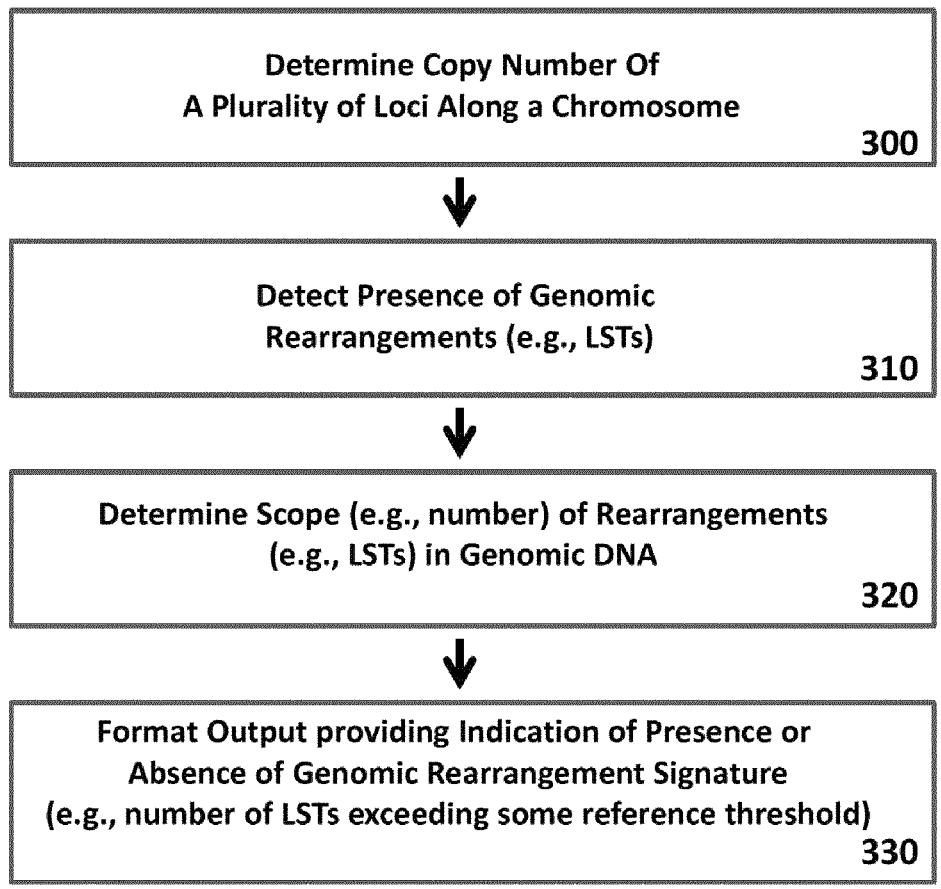
FIG. 9. Process flow chart. Illustrated is a flow chart of an example process for assessing the genome of a cell (e.g., a cancer cell) for a genomic DNA rearrangement.

FIG. 9 shows an exemplary process by which a computing system can determine the presence or absence of a genomic DNA rearrangement. The process begins at box 300, where data regarding the nature of a plurality of loci along a chromosome is collected by the computing system. As described herein, any appropriate assay such as a SNP array-based assay or sequencing-based assay can be used to assess loci along a chromosome. In some cases, a system including a signal detector and a computer can be used to collect data (e.g., fluorescent signals or sequencing results) regarding the nature of the plurality of loci. At box 310, data regarding the nature of a plurality of loci as well as the location or spatial relationship of each locus is assessed by the computing system to determine the presence of a genomic DNA rearrangement. At box 320, data regarding the genomic DNA rearrangements detected is assessed by determining the presence of a genomic DNA rearrangement. At box 330, the computing system formats an output providing an indication of the presence or absence of a genomic DNA rearrangement. Once formatted, the computing system can present the output to a user (e.g., a laboratory technician, clinician, or medical professional). As described herein, the presence or absence of a genomic DNA rearrangement can be used to provide an indication about a patient's likely HR status, an indication about the likely presence or absence of genetic mutations in genes of the HR pathway, and/or an indication about possible cancer treatment regimens.

Figure 10:
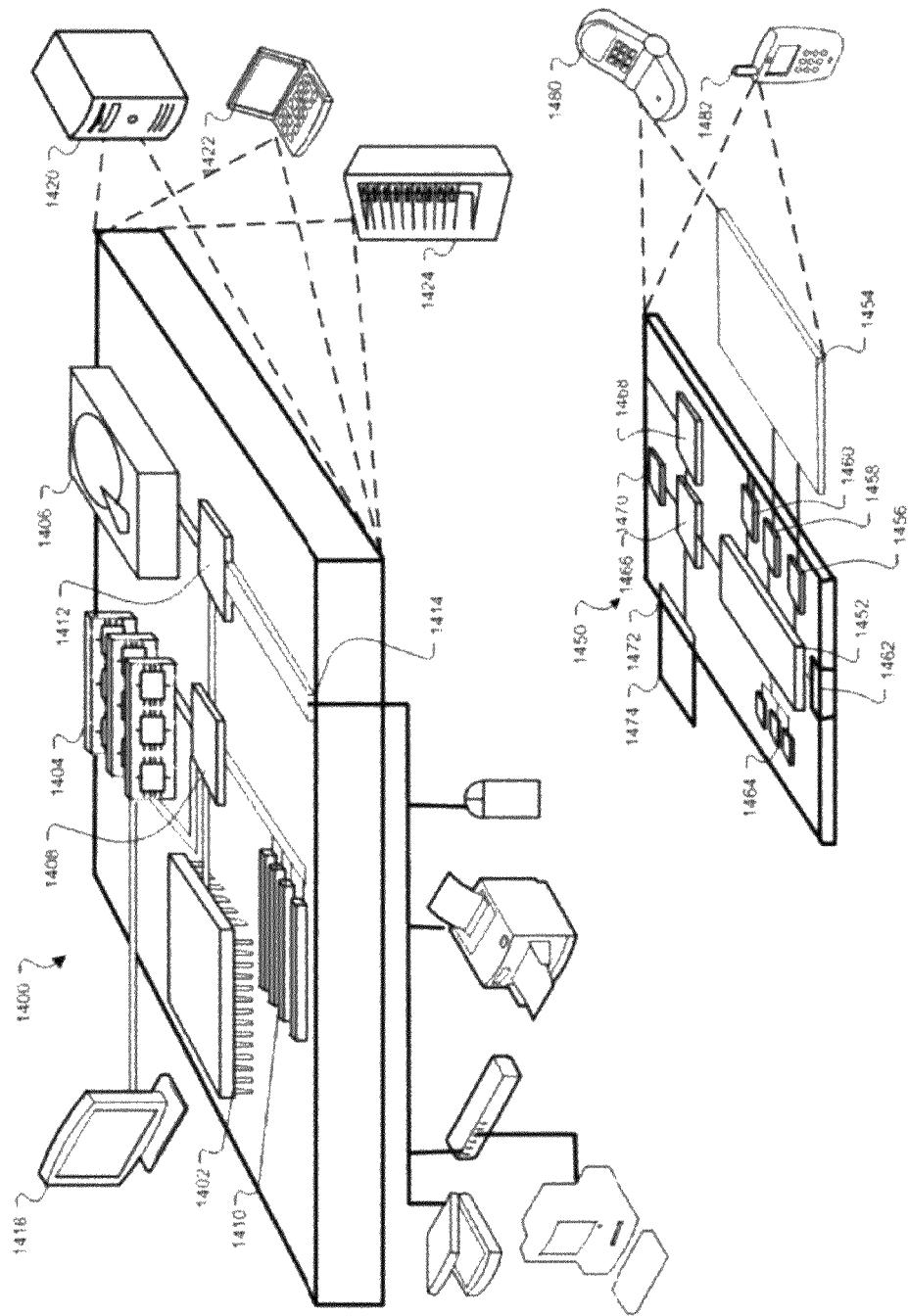
FIG. 10. Computer device diagram. Illustrated is a diagram of an example of a computer device and a mobile computer device that can be used to implement the techniques described herein.

FIG. 10 is a diagram of an example of a computer device 1400 and a mobile computer device 1450, which may be used with the techniques described herein. Computing device 1400 is intended to represent various forms of digital computers, such as laptops, desktops, workstations, personal digital assistants, servers, blade servers, mainframes, and other appropriate computers. Computing device 1450 is intended to represent various forms of mobile devices, such as personal digital assistants, cellular telephones, smart phones, and other similar computing devices. The components shown here, their connections and relationships, and their functions, are meant to be exemplary only, and are not meant to limit implementations of the inventions described and/or claimed in this document.

Computing device 1400 includes a processor 1402, memory 1404, a storage device 1406, a high-speed interface 1408 connecting to memory 1404 and high-speed expansion ports 1410, and a low speed interface 1415 connecting to low speed bus 1414 and storage device 1406. Each of the components 1402, 1404, 1406, 1408, 1410, and 1415, are interconnected using various busses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as display 1416 coupled to high speed interface 1408. In other implementations, multiple processors and/or multiple buses may be used, as appropriate, along with multiple memories and types of memory. Also, multiple computing devices 1400 may be connected, with each device providing portions of the necessary operations (e.g., as a server bank, a group of blade servers, or a multi-processor system).

The memory 1404 stores information within the computing device 1400. In one implementation, the memory 1404 is a volatile memory unit or units. In another implementation, the memory 1404 is a non-volatile memory unit or units. The memory 1404 may also be another form of computer-readable medium, such as a magnetic or optical disk.

The storage device 1406 is capable of providing mass storage for the computing device 1400. In one implementation, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described herein. The information carrier is a computer- or machine-readable medium, such as the memory 1404, the storage device 1406, memory on processor 1402, or a propagated signal.

The high speed controller 1408 manages bandwidth-intensive operations for the computing device 1400, while the low speed controller 1415 manages lower bandwidth-intensive operations. Such allocation of functions is exemplary only. In one implementation, the high-speed controller 1408 is coupled to memory 1404, display 1416 (e.g., through a graphics processor or accelerator), and to high-speed expansion ports 1410, which may accept various expansion cards (not shown). In the implementation, low-speed controller 1415 is coupled to storage device 1406 and low-speed expansion port 1414. The low-speed expansion port, which may include various communication ports (e.g., USB, Bluetooth, Ethernet, or wireless Ethernet) may be coupled to one or more input/output devices, such as a keyboard, a pointing device, a scanner, an optical reader, a fluorescent signal detector, or a networking device such as a switch or router, e.g., through a network adapter.

The computing device 1400 may be implemented in a number of different forms, as shown in the figure. For example, it may be implemented as a standard server 1420, or multiple times in a group of such servers. It may also be implemented as part of a rack server system 1424. In addition, it may be implemented in a personal computer such as a laptop computer 1422. Alternatively, components from computing device 1400 may be combined with other components in a mobile device (not shown), such as device 1450. Each of such devices may contain one or more of computing device 1400, 1450, and an entire system may be made up of multiple computing devices 1400, 1450 communicating with each other.

Computing device 1450 includes a processor 1452, memory 1464, an input/output device such as a display 1454, a communication interface 1466, and a transceiver 1468, among other components (e.g., a scanner, an optical reader, a fluorescent signal detector). The device 1450 may also be provided with a storage device, such as a microdrive or other device, to provide additional storage. Each of the components 1450, 1452, 1464, 1454, 1466, and 1468, are interconnected using various buses, and several of the components may be mounted on a common motherboard or in other manners as appropriate.

The processor 1452 can execute instructions within the computing device 1450, including instructions stored in the memory 1464. The processor may be implemented as a chipset of chips that include separate and multiple analog and digital processors. The processor may provide, for example, for coordination of the other components of the device 1450, such as control of user interfaces, applications run by device 1450, and wireless communication by device 1450.

Processor 1452 may communicate with a user through control interface 1458 and display interface 1456 coupled to a display 1454. The display 1454 may be, for example, a TFT LCD (Thin-Film-Transistor Liquid Crystal Display) or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452. In addition, an external interface 1462 may be provide in communication with processor 1452, so as to enable near area communication of device 1450 with other devices. External interface 1462 may provide, for example, for wired communication in some implementations, or for wireless communication in other implementations, and multiple interfaces may also be used.

The memory 1464 stores information within the computing device 1450. The memory 1464 can be implemented as one or more of a computer-readable medium or media, a volatile memory unit or units, or a non-volatile memory unit or units. Expansion memory 1474 may also be provided and connected to device 1450 through expansion interface 1472, which may include, for example, a SIMM (Single In Line Memory Module) card interface. Such expansion memory 1474 may provide extra storage space for device 1450, or may also store applications or other information for device 1450. For example, expansion memory 1474 may include instructions to carry out or supplement the processes described herein, and may include secure information also. Thus, for example, expansion memory 1474 may be provide as a security module for device 1450, and may be programmed with instructions that permit secure use of device 1450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described herein. The information carrier is a computer- or machine-readable medium, such as the memory 1464, expansion memory 1474, memory on processor 1452, or a propagated signal that may be received, for example, over transceiver 1468 or external interface 1462.

Device 1450 may communicate wirelessly through communication interface 1466, which may include digital signal processing circuitry where necessary. Communication interface 1466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1468. In addition, short-range communication may occur, such as using a Bluetooth, WiFi, or other such transceiver (not shown). In addition, GPS (Global Positioning System) receiver module 1470 may provide additional navigation- and location-related wireless data to device 1450, which may be used as appropriate by applications running on device 1450.

Device 1450 may also communicate audibly using audio codec 1460, which may receive spoken information from a user and convert it to usable digital information. Audio codec 1460 may likewise generate audible sound for a user, such as through a speaker, e.g., in a handset of device 1450. Such sound may include sound from voice telephone calls, may include recorded sound (e.g., voice messages, music files, etc.) and may also include sound generated by applications operating on device 1450.

The computing device 1450 may be implemented in a number of different forms, as shown in the figure. For example, it may be implemented as a cellular telephone 1480. It may also be implemented as part of a smartphone 1482, personal digital assistant, or other similar mobile device.

Various implementations of the systems and techniques described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, and Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described herein can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described herein can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described herein), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In some cases, a computing system provided herein can be configured to include one or more sample analyzers. A sample analyzer can be configured to produce a plurality of signals about genomic DNA of at least one pair of human chromosomes of a cancer cell. For example, a sample analyzer can produce signals that are capable of being interpreted in a manner that identifies the homozygous or heterozygous nature of loci along a chromosome. In some cases, a sample analyzer can be configured to carry out one or more steps of a SNP array-based assay or sequencing-based assay and can be configured to produce and/or capture signals from such assays. In some cases, a computing system provided herein can be configured to include a computing device. In such cases, the computing device can be configured to receive signals from a sample analyzer. The computing device can include computer-executable instructions or a computer program (e.g., software) containing computer-executable instructions for carrying out one or more of the methods or steps described herein. In some cases, such computer-executable instructions can instruct a computing device to analyze signals from a sample analyzer, from another computing device, from a SNP array-based assay, or from a sequencing-based assay. The analysis of such signals can be carried out to determine genotypes, homozygosity at certain loci, regions of homozygosity, the number genomic DNA rearrangements, to determine whether or not a sample is positive for a genomic DNA rearrangement, to determine the number of genomic DNA rearrangements in at least one pair of human chromosomes, to determine a likelihood of a deficiency in BRCA1 and/or BRCA2 genes, to determine a likelihood of a deficiency in HR, to determine a likelihood that a cancer patient will respond to a particular cancer treatment regimen (e.g., a regimen that includes a DNA damaging agent, an anthracycline, a topoisomerase I inhibitor, radiation, a PARP inhibitor, or a combination thereof), or to determine a combination of these items.

In some cases, a computing system provided herein can include computer-executable instructions or a computer program (e.g., software) containing computer-executable instructions for formatting an output providing an indication about a genomic DNA rearrangement, the size of a genomic DNA rearrangement, the number of genomic DNA rearrangements having a particular size or range of sizes, whether or not a sample is positive for a genomic DNA rearrangement, the number of genomic DNA rearrangements in at least one pair of human chromosomes, a likelihood of a deficiency in BRCA1 and/or BRCA2 genes, a likelihood of a deficiency in HR, a likelihood that a cancer patient will respond to a particular cancer treatment regimen (e.g., a regimen that includes a DNA damaging agent, an anthracycline, a topoisomerase I inhibitor, radiation, a PARP inhibitor, or a combination thereof), or a combination of these items. In some cases, a computing system provided herein can include computer-executable instructions or a computer program (e.g., software) containing computer-executable instructions for determining a desired cancer treatment regimen for a particular patient based at least in part on the presence or absence of a genomic DNA rearrangement.

In some cases, a computing system provided herein can include a pre-processing device configured to process a sample (e.g., cancer cells) such that a SNP array-based assay or sequencing-based assay can be performed. Examples of pre-processing devices include, without limitation, devices configured to enrich cell populations for cancer cells as opposed to non-cancer cells, devices configured to lyse cells and/or extract genomic nucleic acid, and devices configured to enrich a sample for particular genomic DNA fragments.

The present invention also provides kits for assessing samples (e.g., cancer cells) as described herein. For example, this document provides kits for assessing cancer cells for the presence of a genomic DNA rearrangement (e.g., an LST) in at least one pair of human chromosomes. A kit provided herein can include either SNP probes (e.g., an array of SNP probes for carrying out a SNP array-based assay described herein) or primers (e.g., primers designed for sequencing SNP regions via a sequencing-based assay) in combination with a computer program product containing computer-executable instructions for carrying out one or more of the methods or steps described herein (e.g., computer-executable instructions for determining the presence of a genomic DNA rearrangement having a particular size or range of sizes). In some cases, a kit provided herein can include at least 500, 1000, 10,000, 25,000, or 50,000 SNP probes capable of hybridizing to polymorphic regions of human genomic DNA. In some cases, a kit provided herein can include at least 500, 1000, 10,000, 25,000, or 50,000 primers capable of sequencing polymorphic regions of human genomic DNA. In some cases, a kit provided herein can include one or more other ingredients for performing a SNP array-based assay or a sequencing-based assay. Examples of such other ingredients include, without limitation, buffers, sequencing nucleotides, enzymes (e.g., polymerases), etc. This document also provides the use of any appropriate number of the materials provided herein in the manufacture of a kit for carrying out one or more of the methods or steps described herein. For example, this document provides the use of a collection of SNP probes (e.g., a collection of 10,000 to 100,000 SNP probes) and a computer program product provided herein in the manufacture of a kit for assessing cancer cells for the presence of a genomic DNA rearrangement. As another example, this document provides the use of a collection of primers (e.g., a collection of 10,000 to 100,000 primers for sequencing SNP regions) and a computer program product provided herein in the manufacture of a kit for assessing cancer cells for the presence of a genomic DNA rearrangement.

The invention will be further described by the following examples and figures, which are not intended to limit the scope of the protection defined by the claims.

EXAMPLES

Example 1

Materials and Methods
Patients and Tumors

A series of undifferentiated grade 3 BLCs was assembled from patients who had surgery at the Institut Curie. According to French regulations patients were informed of research and did not express opposition. High quality biological material was available at Institut Curie biobank for 85 tumor samples (some samples were described previously).[28-30] This series was enriched for tumors arisen in patients carrying deleterious BRCA1 mutations (35 tumors).

Immunohistochemistry

Immunostaining was performed on 4 μm tissue sections as described previously:[28,29] ER, PR and ERBB2 (Novocastra), EGFR and KRT8/18 (Zymed, Invitrogen), KRTS/6 (Dako) and KRT14 (Biogenex). Positivity for each marker was determined according to standardized guidelines.[31] Negativity was defined as total absence of staining for expression of ER and PR, and as less than 2+ staining for ERBB2.

The basal-like phenotype was defined according to morphological, phenotypic and/or molecular criteria including i) high grade (Elston-Ellis grading) and pushing margins, ii) triple-negative phenotype and expression of either KRTS/6/14/17 or EGFR assessed by immunohistochemistry.[32]

Methylation Status of BRCA1 Promoter

Methylation of the promoter of BRCA1 was assessed by methyl-specific PCR (MSP) after bisulfite conversion as described previously,[33] with minor modifications (primer sequences and protocols are available upon request).

BRCA1 Mutation Status

Pre-screen for mutations of the BRCA1 gene was performed using Enhanced Mismatch Mutation Analysis (EMMA, Fluigent[34]; EMMALYS software P/N: 5331254102). For abnormal EMMA profiles, the concerned BRCA1 exons were sequenced with dideoxynucleotides (BigDye Terminator V1.1, Applied Biosystems, Foster City, Calif.), according to standard protocols (primer sequences and protocols are available upon request). Sequences were examined with the Seqscape V2.5 (Applied Biosystems).

Analysis of Transcriptomic Data

Transcriptomic data was obtained on the Affymetrix U133plus2 platform in the Institut Curie according to the standard protocol. Normalization was performed with Brain-Array algorithm[35]. Unsupervised clustering was performed based on the intrinsic signature[36].

Processing the Genomic Profiles

Genomic profiling of 85 BLCs was performed using two platforms: Illumina (Illumina SNP HapMap 300K Duo, 33 cases) and Affymetrix (Affymetrix SNP Chip 6.0, 52 cases).

Illumina Platform:

Genomic profiling of the tumor samples was performed by a service provider (Integragen, Evry, France) on 300K Illumina SNP-arrays (Human Hap300-Duo). Raw data files were processed by BeadStudio 3.3 in standard settings using supporting data provided by Illumina (HumanHap300v2_A). Allele specific signals (X and Y in BeadStudio notation) were processed into Log R ratio and B allele frequency by tQN algorithm.[37]

Affymetrix Platform:

Hybridization was performed at Institut Curie on Affymetrix SNPChip6.0 array. Cell files were processed by Genotyping Console 3.0.2. Log 2Ratio and Allele Difference profiles resulted from Copy Number and LOH analysis performed with the reference model file HapMap270 (GenomeWideSNP_6.hapmap270.na29) provided by Affymetrix.

Quality Control:

20 SNP arrays were discarded due to: low hybridization quality (3 arrays); low tumor content and/or ambiguous profile interpretation (17 arrays).

Segmental Copy Number and Genotype Detection:

Both Illumina and Affymetrix SNP array data were mined using the GAP method described and validated previously: segmental copy numbers, allelic contents (major allele counts) and normal cell contamination were detected; segmentations were optimized with respect to the genomic status detected. [27]

Recognition of absolute copy number ranged from 0 to 8 copies with all segments exceeding 8-copy level been ascribed 8-copy status. Thus, 22 possible segmental genotypes were discriminated (copy number/major allele count): 1 copy A (or 1/1); 2 copies AA (2/2) and AB (2/1); 3 copies AAA (3/3), AAB (3/2); 4 copies AAAA (4/4), AAAB (4/3), AABB (4/2), etc . . .

Chromosome Number:

Number of chromosomes was estimated by the sum of the copy numbers detected at the pericentric regions. The status of the pericentric region of each chromosome arm was defined by the corresponding juxta-centromeric segment when the latter contained 500 SNPs or more. When not measurable, missing values were substituted by the modal copy number of the considered chromosome arm (3.4±2.2 out of 41 chromosome arms per genome were substituted in the series). Chromosome counting procedure was validated by comparing estimated chromosome numbers versus available numbers from karyotype or SKY data for 25 breast cancer cell lines {lgcstandards-atcc.org/}. Error rate was less than 2 chromosomes per sample (1.58±2.3).

Breakpoint Counts:

Number of breakpoints in each genomic profile was estimated based on the resulting interpretable copy number profile and after filtering less than 50 SNPs variation. Small interstitial alterations were defined as <3 Mb alterations surrounded by the segments with identical status for genotype and copy number. They were removed when estimating total number of breakpoints. Large-scale State Transitions (LSTs) were calculated after smoothing and filtering of variation less than 3 Mb in size.

Compilation of Validation Sets

The validation series comprises 55 samples including TNBC from a cohort of young women with breast cancer (17 cases); BLCs with medullary features (8 cases) and one BLC arisen in a BRCA2 mutation carrier; BRCA1 BLCs from GEO GSE19177 (12 cases)[38]; basal-like tumors from GEO GSE32530 (4 cases)[39]; BRCA1 BLCs from Institut Bergonié (5 cases).

Basal-like cell lines with available SNP array profile comprised 17 cases (15 cases hybridized in Institute Curie and 2 cases were obtained from the Wellcome Trust Sanger Institute Cancer Genome Project web site.

Results

BRCA1 Status of Basal-Like Carcinomas (BLCs)

A series of 65 well characterized basal-like breast carcinomas included 23 tumors arisen in patients carrying deleterious BRCA1 mutations (herein called "BRCA1 BLCs") and 42 BLCs arisen in patients without evidence of familial predisposition of breast/ovarian cancer or tested negative for BRCA1/2 mutations (herein called "sporadic BLCs"). Sporadic BLCs were tested for the methylation of the BRCA1 promoter and nearly 25% were found positive (11 out of 41 tested, herein called "meBRCA1 BLCs"). No evidence of methylation in the remaining 31 cases was found. BRCA1 status was confirmed by the gene expression in 35 out of 36 tested cases with available transcriptomic data. BRCA1 and meBRCA1 BLCs comprise the group of tumors with proven BRCA1 inactivation (34 cases), which were further compared to the group of presumably non-BRCA1 BLCs (31 cases).

Near-Diploidy in BLCs has 75% Positive Predictive Value of BRCA1 Inactivation

In order to get insight into the specific genomic alterations of BLCs, genomic profiling was performed using SNP-arrays, which provide two complementary measurements: copy number variation and allelic imbalance. Genome Alteration Print (GAP) methodology for mining SNP arrays[27] allowed us to obtain the segmental genotype profiles (e.g. exact copy numbers and allelic contents: A, AB, AA, AAB, AAA, . . . ) for each sample. General genomic characteristics such as number of chromosomes, DNA index, number of chromosome breaks, and proportions of genome in each genomic state were inferred from the segmental genotype profiles.

Estimated chromosome counts per genome showed a bimodal distribution (FIG. 1, top panel) similar to those demonstrated for the genomes in various types of cancers[40]. Tumor genomes carrying less than 50 chromosomes and with the DNA index close to 1 were considered to have ploidy of two and were thereafter called "near-diploid genomes" (23 cases). Following the hypothesis of the whole genome duplication during cancer progression explaining the second mode in chromosome distribution[40] tumor genomes carrying more than 50 chromosomes and DNA index higher than 1.2 were considered to have a ploidy of four and were thereafter called "over-diploid genomes" (42 cases).

Interestingly, the 23 near-diploid tumors almost consistently carried germline mutation or epigenetic inactivation of BRCA1 (20/23) in contrast to the over-diploid tumors, which were slightly enriched in non-BRCA1 BLCs (28/42) (FIG. 1, bottom panel). Taking into account the fact that BRCA1 germline mutation is responsible for near 10% of basal-like carcinomas[41] positive predictive value of genomic near-diploid status was estimated to be 75%.

Large-Scale Chromosomal Rearrangements Discriminate BRCA1 and Non-BRCA1 Basal-Like Carcinomas Total number of breakpoints detected in the cancer genome characterizes the level of genomic instability. However, overall comparison of BRCA1 versus non-BRCA1 tumors did not show any significant difference (p-value=0.28). In the subgroup of 42 over-diploid BLCs, 14 BRCA1-inactivated tumors displayed elevated total number of breakpoints (range [57-224], 140.6±45.7), while 28 non-BRCA1 tumors showed significant heterogeneity (range [8-213], 101.2±50.6) and were enriched in the low values compared to BRCA1 tumors (p<0.017, Wilcoxon rank test). However, large overlap in the breakpoint numbers precluded accurate demarcation.

In order to get a robust and discriminative estimation of the genomic instability we evaluated the number of Large-scale State Transitions (LSTs) by calculating chromosomal breaks between adjacent regions of at least 10 Mb (comprising ~3000 SNPs in Affymetrix SNP6.0).

Figure 2:
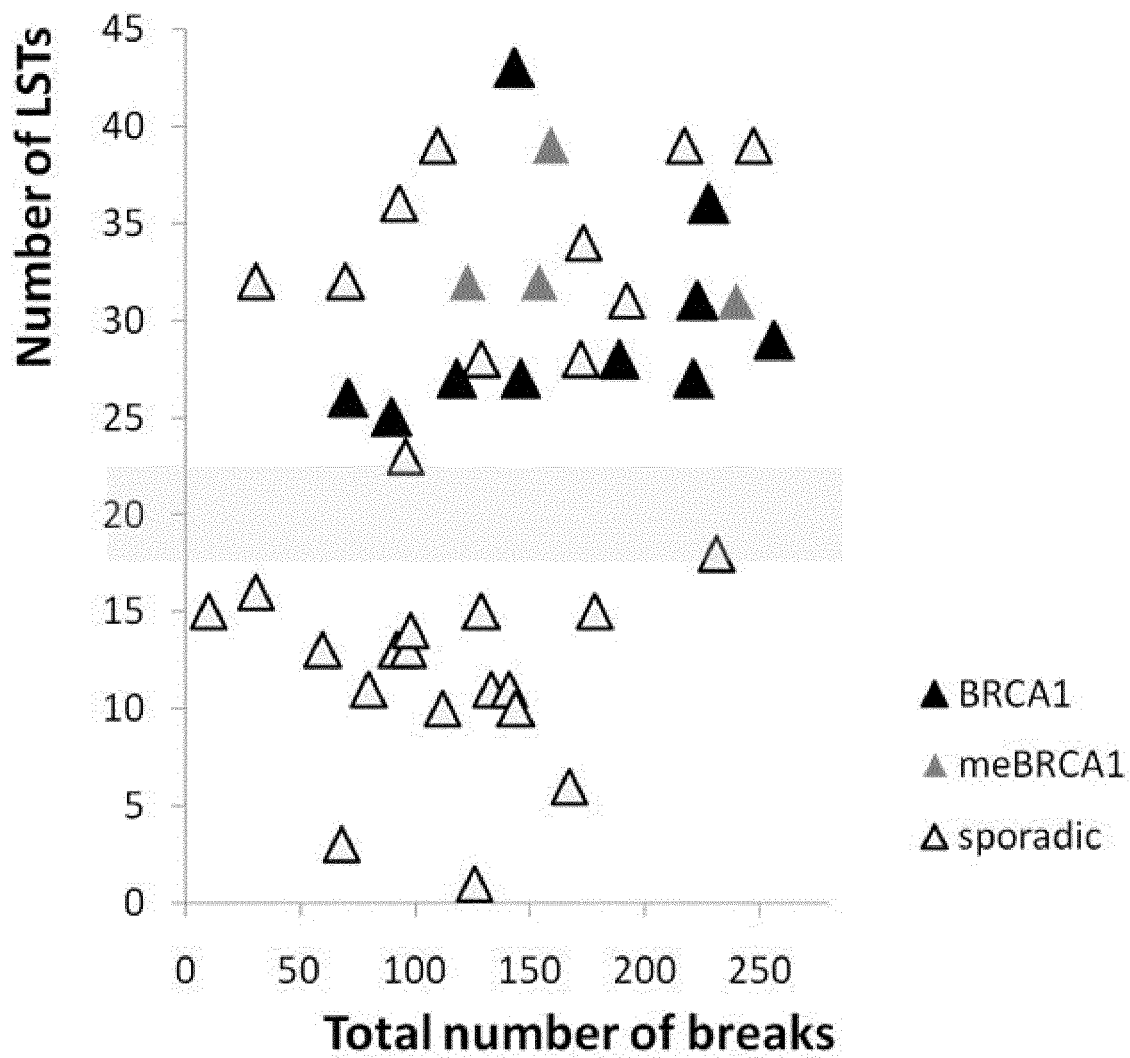
FIG. 2. Genomic instability in over-diploid BLCs as estimated by the total number of breaks and by LSTs. LST number clearly discriminated non-BRCA1 BLCs from BLCs with proven BRCA1 inactivation (p-value <0.001, Wilcoxon test). Total number of breaks was less significantly different between non-BRCA1 vs BRCA1 and meBRCA1 comparison (p-value <0.03, Wilcoxon test) and was not discriminative. BRCA1: germline BRCA1 mutation; meBRCA1: BRCA1 promoter methylation; sporadic=non-BRCA1: absence of evidence of BRCA1 inactivation.

Number of LSTs in the subgroup of over-diploid tumors had a bimodal distribution with a clear gap between two modes (12.5±4.9 and 35.5±6.7) separating 18 non-BRCA1 BLCs from the mixture containing 14 BRCA1-inactivated tumors and 10 tumors with neither BRCA1 germline mutation nor BRCA1 promoter methylation (FIG. 2). In the subgroup of 23 near-diploid BLCs, which mainly contained BRCA1 tumors, LSTs had unimodal distribution (28.0±6.5) with two non-BRCA1 tumors within one standard deviation (24 and 28 LSTs) and one non-BRCA1 BLC below two standard deviations from the average (12 LSTs). Interestingly, all tumors with low LSTs had no evidence of BRCA1 inactivation and displayed either few chromosomal breaks and a high level of aneuploidy (3 samples) or firestorm-like alterations (16 samples).

To conclude, LSTs reflected well the overall genomic patterns of the tumors, contrary to the total number of breakpoints, and provided the discriminative values for BRCA1 status prediction.

A Two-Step Decision Rule Consistently Detects BRCA1 Inactivation in BLCs.

Based on the LSTs distributions described above, two references for BRCAness prediction were applied, more than 15 LSTs per genome in the near-diploid cases and more than 20 LSTs in the over-diploid cases, predicting BRCAness with 100% sensitivity (p-value=4*10$^{-5}$, Fisher test).

Figure 3:
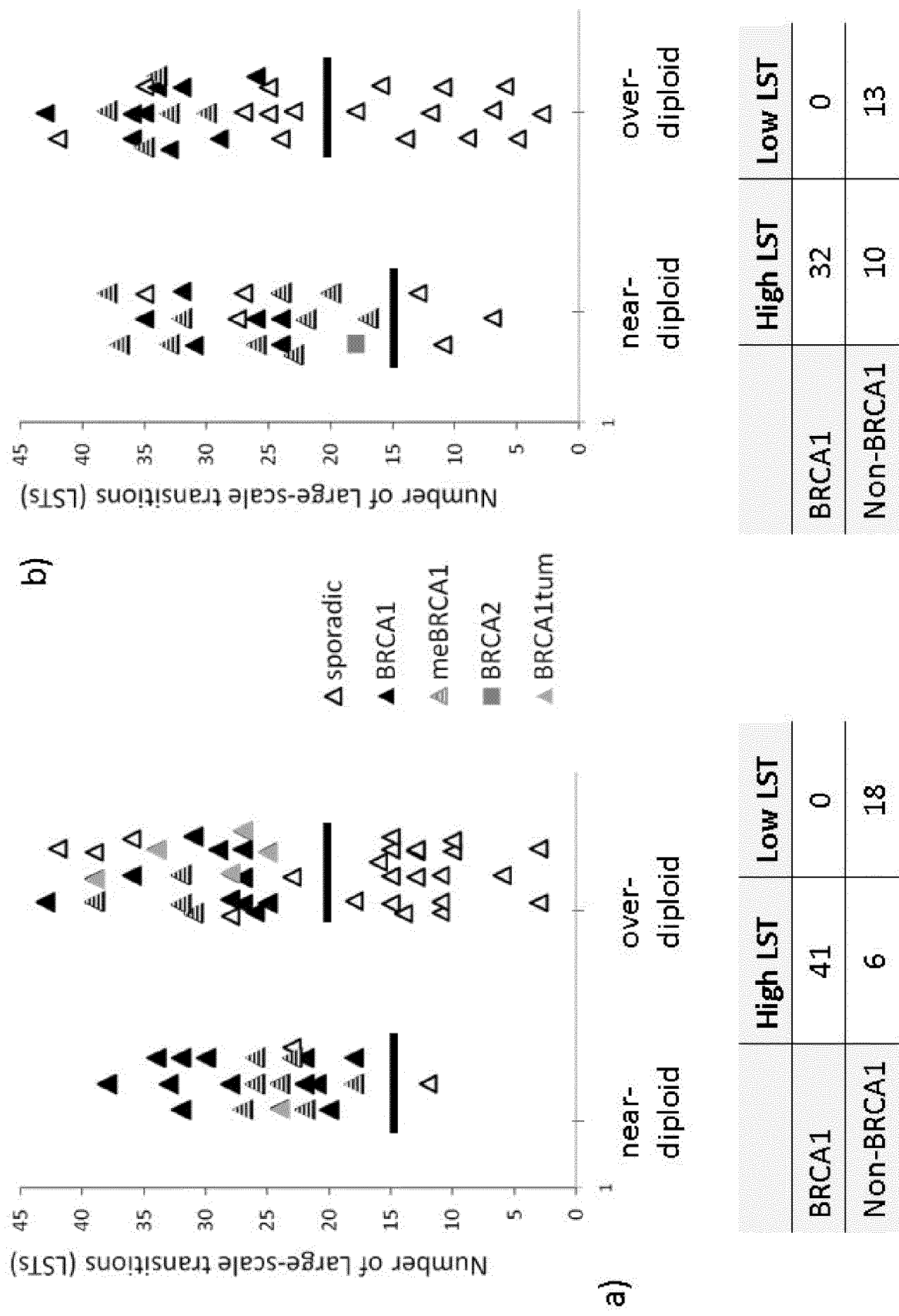
FIG. 3. Tumor ploidy and the number of large-scale transitions (LST) are discriminative of BRCA1 inactivation in the experimental (left) and validation (right) sets. Upper panel: number of LSTs per tumor is indicated in relation to ploidy categories. Near-diploid and near-tetraploid cutoffs are indicated by a bar. Known BRCA1 and BRCA2 statuses are indicated for germline mutations ("BRCA1" and "BRCA2"), methylation of the BRCA1 promoter ("meBRCA1") and mutations in the tumors ("tumBRCA1"). Tumors without evidence of BRCA1/2 inactivation are referred to as "non-BRCA1". Fisher's exact tests are indicated below the contingency tables; BRCA1 refers to all proven BRCA1-inactivated BLCs, non-BRCA1 refers to BLCs without evidence of BRCA1 inactivation.

Moreover, all "False Positive" cases (thereafter called "BRCA1-looking" BLCs) had similar high number of LSTs as the "True Positive" cases (with proven BRCA1-inactivated status), which actually questioned their false positive status and might evidence other mechanisms of homologous recombination defect including BRCA1 or BRCA2 mutations. Such mutations were searched in 28 sporadic BLCs with available material including 13 cases with the BRCA1-looking pattern. Deleterious BRCA1 mutations were found in six cases all belonging to BRCA1-looking tumors (p-value=0.02). Deleterious BRCA2 mutations were found in three cases all belonging to BRCA1-looking tumors. With these findings specificity reached 89% (p-value=1.4*10$^{-11}$, Fisher test) in the considered experimental set of BLCs (FIG. 3A).

A validation series of 55 BLC/TNBC was assembled, including 15 cases with BRCA1 germline mutations, 15 cases with BRCA1 promoter methylation, 1 case with a BRCA2 germline mutation, and 24 sporadic cases. SNP array data were processed using the same workflow. Prediction of the BRCA1 inactivation displayed sensitivity of 100% (all 30 BRCA1 inactivated cases were predicted to be BRCA1-looking) and specificity of 80% (11 cases were predicted to be BRCA1-looking with yet no evidence of BRCA1 inactivation) (FIG. 3B; p-value=1.7*10$^{-6}$, Fisher test). Noteworthy, the BRCA2 mutated tumor was near-diploid with a high LST number, thus clearly following a BRCA1-looking pattern.

Figure 4:
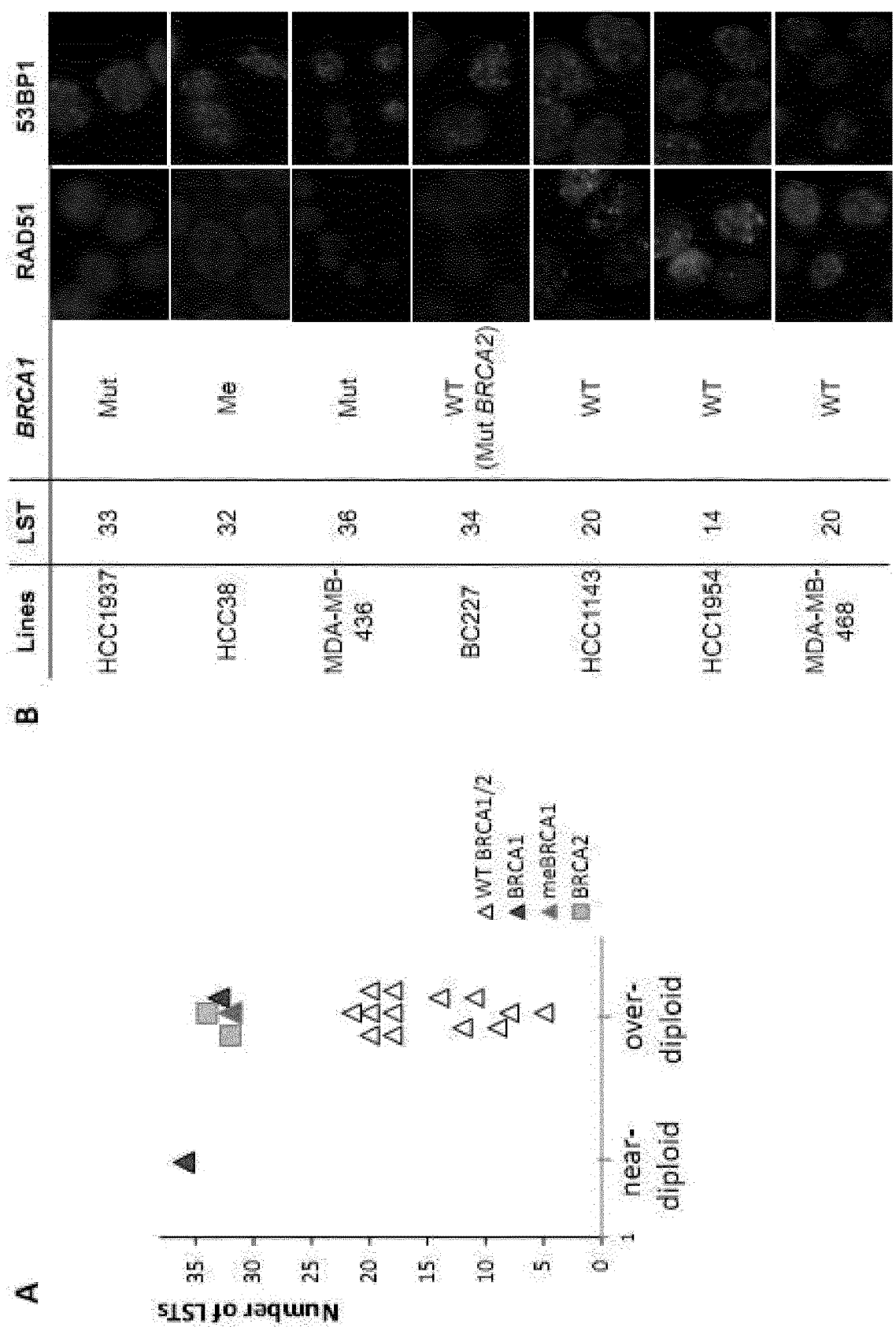
FIG. 4. Genomic and functional assessments of BRCAness in basal-like cell lines. A. Cell lines with basal-like phenotype display discriminative features of BRCAness similar to primary BLCs. Known status for BRCA1 and BRCA2 are indicated for germline mutations ("BRCA1" and "BRCA2") and methylation of BRCA1 promoter ("meBRCA1"). Cell lines without evidence of BRCA1/2 inactivation are described as "non-BRCA1/2". B. RAD51 foci formation 8 hours after 10 Gy irradiation illustrates active homologous recombination (HR) in non-BRCA1 cell lines, and conversely deficient HR in BRCA1 or BRCA2 mutated cell lines. 53BP1 foci in the same experiment are shown as a control for DNA damage response. Scale bars, 20 μm). Number of LST is indicated as well as BRCA1/2 status: mut, mutated; me, methylation of the promoter; wt, wildtype.

Model Systems Supported the Discriminative Features Observed in the Primary Tumors A series of 17 basal-like cell lines was analyzed, including MDA-MB-436 and HCC1937 bearing BRCA1 mutations[42] and HCC38 with BRCA1 promoter methylation[43]. The obtained results followed the trend found in primary tumors: firstly the only near-diploid cell line found was the BRCA1 mutated MDA-MB-436; secondly among over-diploid cell lines, HCC1937 and HCC38 carried the highest number of large-scale chromosomal breaks, which is again consistent with their BRCA1-inactivated status. Nevertheless, and as expected considering cell line establishment and long term maintenance in culture, the cutoff separating non-BRCA1 cell lines was found shifted to 23 LSTs (FIG. 4). One cell line HCC1599 had LST number very close to BRCA1 inactivated cell lines, whereas not associated with BRCA1/2 mutation[44]. To clarify the BRCA1 function and more precisely the homologous recombination pathway, RAD51 foci were measured 8 hours after ionizing radiations in BLC cell lines. All cell lines without BRCA1 looking pattern had the expected RAD51 foci accumulation, whereas no foci were observed in cell lines with BRCA1 looking pattern, including HCC1599 (data not shown).

In conclusion, the inventors have shown that it is possible to predict tumor deficiency in the DNA homologous recombination (HR) pathway in a patient suffering from cancer, by quantifying the number of rearrangements in the genomic DNA of a tumor sample obtained from said patient, wherein the number of rearrangements corresponds to the number, per genome, of breakpoints resulting in segments of at least 10 megabases.

Similar results were obtained by using a cutoff value between 3 megabases and 20 megabases for the definition of Large Scale Transitions.

Example 2—Performance of LST Number Predicting BRCAness in all Types of Breast Carcinomas The series of 426 breast tumors (invasive ductal carcinomas including HER2-positive tumors, luminal (eg expressing receptors for estrogen or progesterone), triple negative/basal-like breast carcinoma (eg expressing no hormone receptors and not overexpressing HER2) as well as rare subtypes such as medullary carcinomas or micropapillary carcinomas from Institut Curie) was considered. The series was enriched with BRCA1 and BRCA2 mutated tumors. The cut-offs on the LST number predicting BRCAness were inferred based on this series (Table 1). False Positive and True Positive Rates (FPR and TPR) show the quality of LST based predictor of BRCAness.

TABLE 1

Cut-offs for breast cancer BRCAness prediction based on the LST number

| LST_S | Ploidy 2: (P = 68, N = 182) | | | Ploidy 4: (P = 53, N = 123) | | |
|---|---|---|---|---|---|---|
| Mb, S | Cut-Off* | FPR | TPR | Cut-Off | FPR | TPR |
| 6 | 19 (17) | 0.04 | 0.99 | 32 (32) | 0.10 | 1 |
| 7 | 17 (15) | 0.05 | 0.99 | 29 (27) | 0.07 | 0.98 |
| 8 | 14 (14) | 0.06 | 1 | 26 (26) | 0.08 | 1 |
| 9 | 14 (11) | 0.04 | 0.99 | 25 (19) | 0.07 | 0.98 |
| 10 | 11 (11) | 0.07 | 1 | 22 (18) | 0.06 | 0.98 |

*Cut-offs correspond to max(TPR-FPR); cut-offs in parenthesis correspond to 100 sensitivity.
P: Number of positives, e.g. BRCA1/2 mutated tumors; N: Number of negatives, e.g. number of tumors with BRCA1/2 wild-type or status not available; TPR: True positive rate; FPR: False positive rate.

Example 3—the Number of LSTs is a Good Predictor of Response to Treatment

Two publically available data sets from clinical trial of Cisplatin treatment of patients with triple-negative breast tumors [GSE28330 GEO database][59] were processed and the number of LST_10 Mb was calculated for each tumor with good quality of measured profile. Genomic profiles were measured by two types of chip: Affymetrix Oncoscan 70K (Dataset 2) and Oncoscan 300K (Dataset 1). Information about mutational status of BRCA1/2 was available for some tumors. Response to treatment was measured by Miller-Payne score, where 4 and 5 were considered as "positive response", while scores <4 were considered as "no response" [59] Case by case and summary results are presented in Table 2 and Tables 3-5 (statistical comparisons were performed by the Fisher exact test). To conclude, (i)

almost all known BRCA1/2 inactivated cases (17/18) and 15 tumors with wild-type or unknown BRCA1/2 status were classified as LST_high (Table 3); (ii) BRCA1/2 inactivation does not always mean response to Cisplatin (Table 4); (iii) LST_10 Mb is a better cisplatin response predictor than the BRCA1/2 status (Table 4-5).

TABLE 2

Individual results

| Data set | ID | Recognition Quality | BRCA1/2 | Miller-Payne response | LST | Response |
|---|---|---|---|---|---|---|
| 1 | DFHCC_06.202_45R | good | | 5 | High | Yes |
| 1 | DFHCC_06.202_15 | good | mut | 5 | High | Yes |
| 1 | DFHCC_06.202_41 | good | | 5 | High | Yes |
| 1 | DFHCC_06.202_7 | good | mut | 5 | High | Yes |
| 1 | DFHCC_06.202_17 | good | | 5 | High | Yes |
| 2 | DFHCC_04.183_9T | good | non | 5 | High | Yes |
| 2 | DFHCC_04.183_18T | good | mut | 5 | High | Yes |
| 2 | DFHCC_04.183_3T | good | non | 5 | High | Yes |
| 2 | DFHCC_04.183_29T | good | non | 5 | High | Yes |
| 2 | DFHCC_04.183_5T | good | mut | 5 | High | Yes |
| 2 | DFHCC_04.183_17T | good | met | 5 | High | Yes |
| 1 | DFHCC_06.202_6 | good | met | 4 | High | Yes |
| 1 | DFHCC_06.202_48 | good | met | 4 | High | Yes |
| 2 | DFHCC_04.183_7T | good | met | 4 | High | Yes |
| 2 | DFHCC_04.183_8T | good | met | 4 | High | Yes |
| 1 | DFHCC_06.202_40 | good | | 4 | High | Yes |
| 2 | DFHCC_04.183_10T | good | non | 4 | High | Yes |
| 1 | DFHCC_06.202_3 | good | | 4 | High | Yes |
| 1 | DFHCC_06.202_27 | good | | 4 | Low | Yes |
| 1 | DFHCC_06.202_13 | good | met | 3 | High | No |
| 1 | DFHCC_06.202_5 | good | | 3 | Low | No |
| 1 | DFHCC_06.202_4 | good | met | 3 | High | No |
| 2 | DFHCC_04.183_23T | good | met | 3 | High | No |
| 2 | DFHCC_04.183_11T | good | non | 3 | High | No |
| 2 | DFHCC_04.183_25T | good | met | 3 | High | No |
| 2 | DFHCC_04.183_1T | good | met | 3 | High | No |
| 1 | DFHCC_06.202_37 | good | | 3 | Low | No |
| 1 | DFHCC_06.202_20 | good | mut | 2 | High | No |
| 1 | DFHCC_06.202_42 | good | mut | 2 | High | No |
| 1 | DFHCC_06.202_21 | good | | 2 | High | No |
| 2 | DFHCC_04.183_14T | good | non | 2 | High | No |
| 2 | DFHCC_04.183_24T | good | non | 2 | Low | No |
| 2 | DFHCC_04.183_22T | good | non | 2 | Low | No |
| 2 | DFHCC_04.183_28T | good | non | 2 | Low | No |
| 1 | DFHCC_06.202_24 | good | | 2 | Low | No |
| 1 | DFHCC_06.202_10 | good | | 1 | Low | No |
| 1 | DFHCC_06.202_32 | good | | 1 | Low | No |
| 1 | DFHCC_06.202_35 | good | | 1 | Low | No |
| 1 | DFHCC_06.202_46 | good | | 1 | Low | No |
| 2 | DFHCC_04.183_13T | good | non | 1 | Low | No |
| 1 | DFHCC_06.202_34 | good | | 1 | High | No |
| 1 | DFHCC_06.202_29 | good | | 1 | High | No |
| 1 | DFHCC_06.202_45L | good | | 1 | High | No |
| 2 | DFHCC_04.183_4T | good | non | 1 | High | No |
| 2 | DFHCC_04.183_12T | good | non | 1 | Low | No |
| 1 | DFHCC_06.202_18 | good | | 1 | Low | No |
| 1 | DFHCC_06.202_9 | good | | 1 | Low | No |
| 2 | DFHCC_04.183_16T | good | non | 1 | Low | No |
| 1 | DFHCC_06.202_14 | good | | 1 | Low | No |
| 2 | DFHCC_04.183_6T | good | | 1 | Low | No |
| 1 | DFHCC_06.202_28 | good | | 0 | Low | No |
| 2 | DFHCC_04.183_21T | good | non | 0 | High | No |
| 2 | DFHCC_04.183_27T | good | non | 0 | Low | No |
| 2 | DFHCC_04.183_26T | good | met | 0 | Low | No |
| 2 | DFHCC_04.183_15T | bad | met | 0 | | No |
| 2 | DFHCC_04.183_20T | bad | non | 2 | | No |
| 2 | DFHCC_06.202_33 | good | | NA | | |
| 2 | DFHCC_06.202_43 | good | | NA | | |
| 2 | DFHCC_06.202_50 | good | | NA | | |
| 2 | DFHCC_06.202_39 | bad | | 2 | | No |
| 2 | DFHCC_06.202_39 | bad | | 2 | | No |

TABLE 3

Summary of LST versus BRCA1/2

| ALL | LST_high | LST_low | |
|---|---|---|---|
| BRCA1/2 | 18 | 1 | $p < 0.0001$ |
| NON BRCA1/2 or NA | 15 | 20 | |

TABLE 4

Summary of BRCA1/2 versus Response

| ALL | Responders | Non Responders | |
|---|---|---|---|
| BRCA1/2 | 9 | 8 | $p < 0.06$ |
| NON BRCA1/2 or NA | 10 | 27 | |

TABLE 5

Summary of LST versus Response

| ALL | LST_high | LST_low | |
|---|---|---|---|
| Non Responders | 15 | 20 | $p < 0.0001$ |
| Responders | 18 | 1 | |

Example 4—LST in Ovarian Carcinoma

Figure 5:
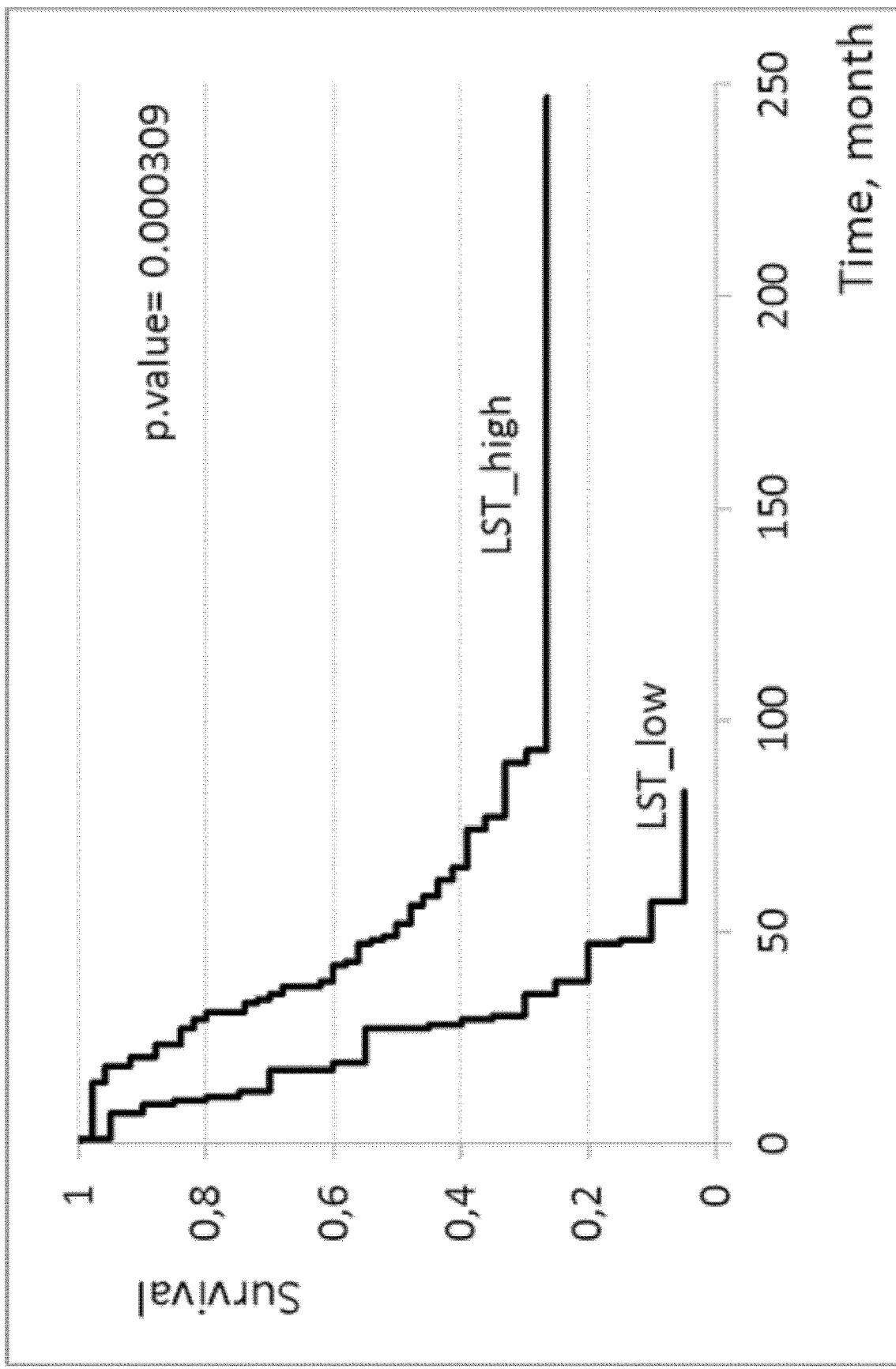
FIG. 5. Survival curves for LST_high and LST_low ovarian tumors. P-value was estimated by log-rank test statistic.
Figure 6:
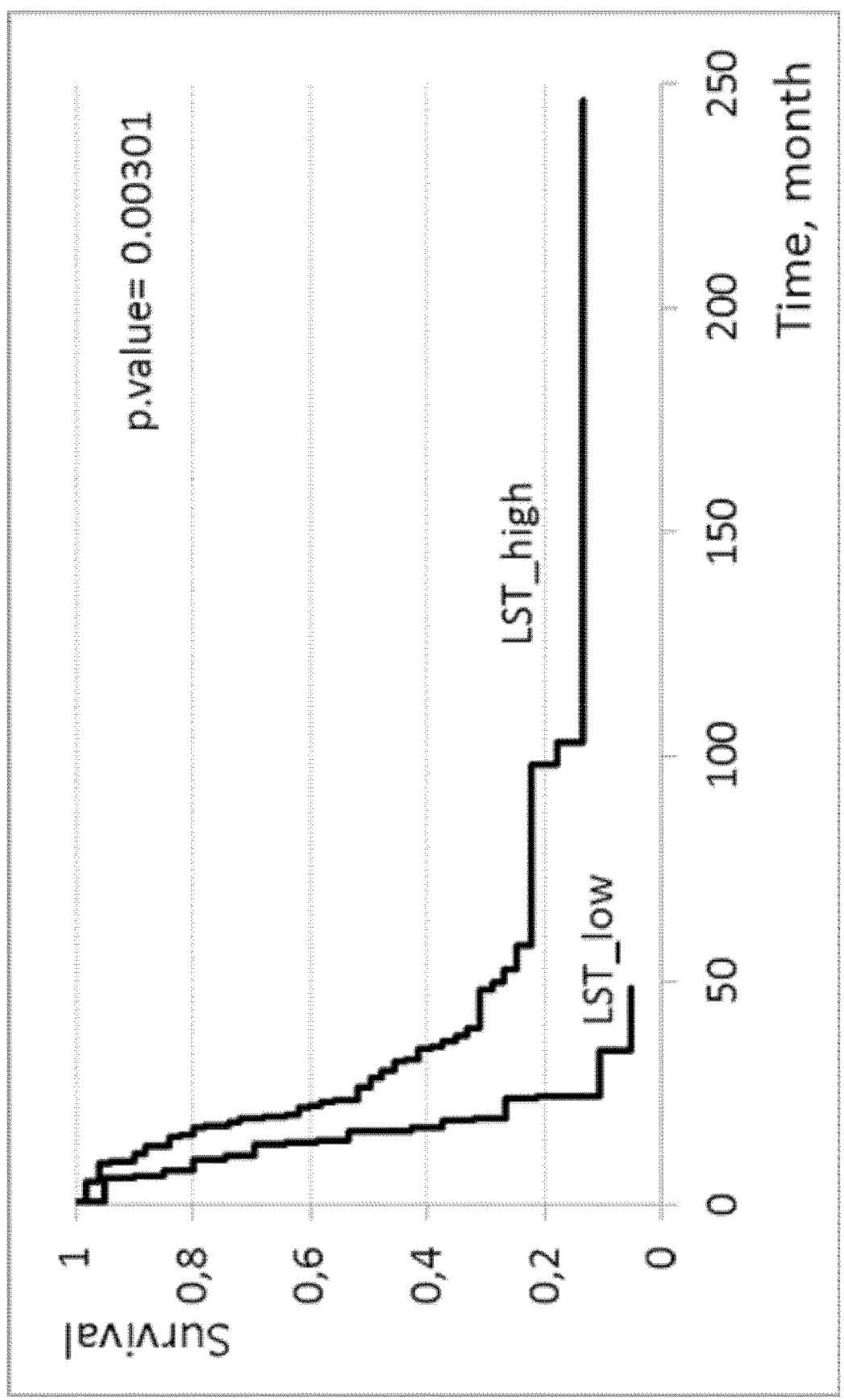
FIG. 6. Event free survival curves for LST_high and LST_low ovarian tumors. P-value was estimated by log-rank test statistic.

Series of high grade ovarian carcinoma from Institut Curie were profiled by SNP arrays (Affymetrix CytoScanHD). All patients were treated by chemotherapies including platinum salts. Tumor genomes were annotated as LST_high (50 cases) and LST_low (20 cases) based on the LST_6 Mb with the cutoffs 19 and 32 LSTs for near-diploid and near-tetraploid tumors respectively. Comparison of Overall Survival and Event Free Survival showed better outcome for patients with LST_high tumors, which indicates better response to treatment (FIGS. 5-6).

Example 5—LST in Tumor Cell Lines

Figure 7:
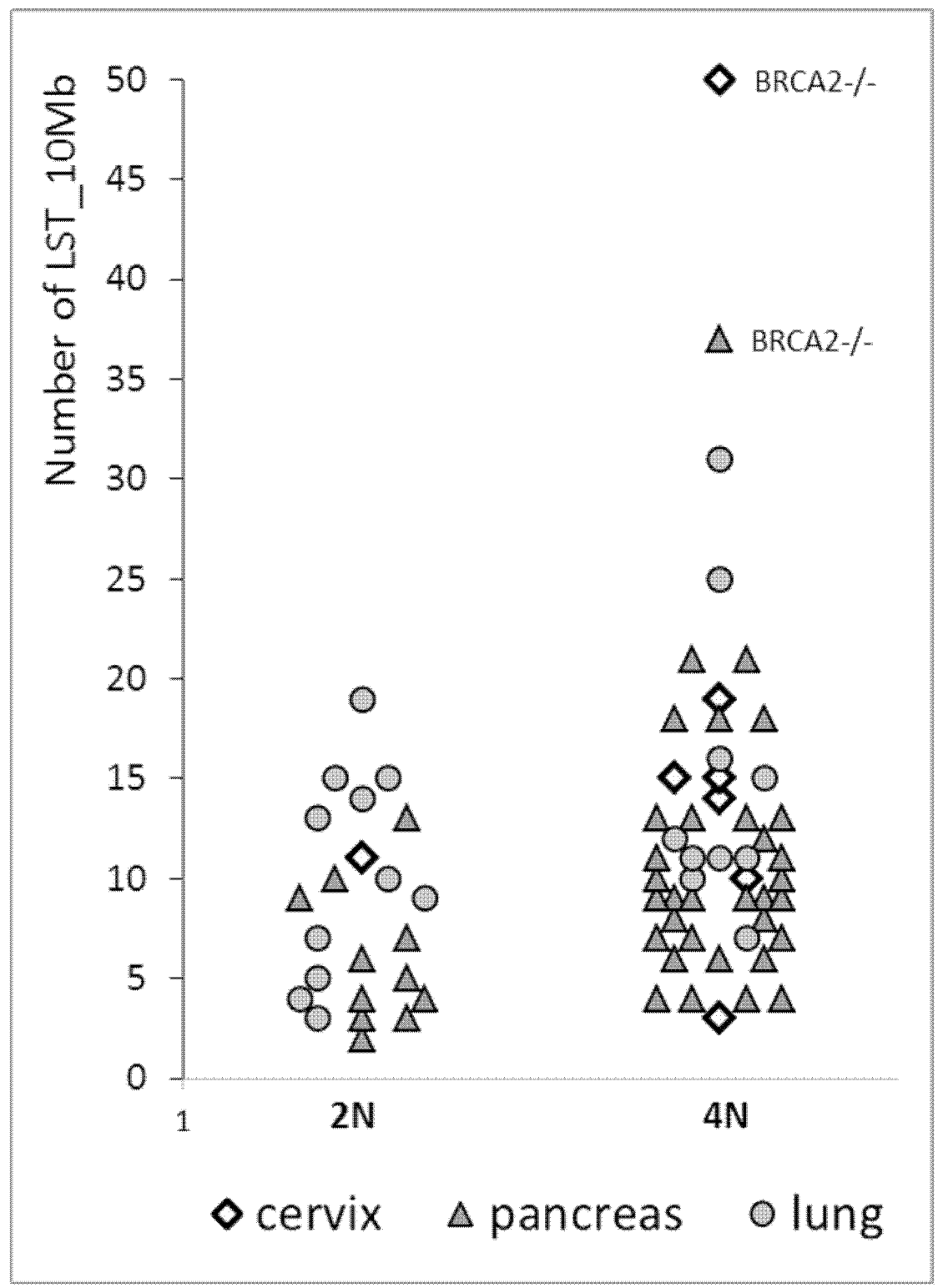
FIG. 7. LST_10 Mb in tumor cell lines. Calculated ploidy is indicated (2N pseudo-diploid, 4N pseudo-tetraploid). Triangle: wild-type or unknown BRCA1/2 status; square: BRCA2 mutated cell lines.

Series of tumor cell lines with known BRCA status and with available SNP-array data were analyzed. LST_10 Mb was calculated and samples with high LST were linked to BRCA2 inactivation in cervix and pancreatic carcinoma cell lines. Two lung cell lines without known BRCA1/2 mutations have a high level of LST, presumably due to BRCA1 methylation described in this disease [60] (FIG. 7).

This validation of the method in tumor cell lines of various origins and state of differentiation indicates that LST measurement and prediction of the BRCAness can be applied in all types of tumors.

Example 6—LST in Luminal and HER2-Overexpressing Tumors

This example demonstrates the high performance of the LST genomic signature for HRD detection in breast cancers and shows its potential as a biomarker for genetic testing, and patient stratification for clinical trials evaluating platinum salts and PARP inhibitors.

Materials and Methods
Patients and Tumors
  Discovery Cohort.
  A series of 456 invasive breast carcinomas with high quality SNP-arrays profiles was assembled using a published in-house series in order to contain sporadic and hereditary breast carcinomas of different phenotypes (61-65). This series contained 57 HER2 overexpressing (HER2+) tumors and 399 luminal tumors (i.e., expressing either estrogen or progesterone receptors or both) and included 43 hereditary breast cancers collected from germline mutations carriers (16 BRCA1 and 27 BRCA2) and 28 cases from patients with a familial history of breast cancer which tested negative for BRCA1/2.

Validation Cohorts.
  (i) TCGA cohort: 467 tumors with high quality SNP-array profile and available normal/tumor exome sequencing results in variant call format (vcf) from the TCGA Breast Invasive carcinoma dataset were used. (ii) In-house TNBC cohort: a series of 104 TNBC enriched in BRCAi germline mutated cased. (iii) the publically available data from Cisplatin-1 and Cisplatin-2 clinical trials cohorts: 54 TNBCs with suitable quality of Oncoscan (Affymetrix) array profile were obtained from public GEO repository GSE28330 (66).

SNP Array Processing and LST Number Evaluation
  SNP array data were processed using the GAP methodology to obtain absolute copy number (CN) and allelic content profiles. Allelic contents in BRCA1/2 genes loci were extracted. BRCA1/2 loci were checked for homozygous deletions. DNA index was calculated as the averaged CN. Tumor ploidy was set to 2 (near-diploid tumors) or 4 (near-tetraploid tumors) whether DNA index was below or above 1.3. Amplification was called when the copy number was equal or greater than 2 times the tumor ploidy. HRD was predicted based on the number of Large-scale State Transitions (LSTs). Briefly, an LST was defined as a chromosomal breakpoint (change in copy number or major allele counts) between adjacent regions each of at least 10 megabases (Mb) obtained after smoothing and filtering small-scale (less than 3 Mb) copy number variation. The number of LSTs was counted for each tumor. Two ploidy-specific cut-offs (15 and 20 for near-diploid and near-tetraploid genomes, respectively) were used to classify tumors as "LST$^{hi}$" (number of LSTs≥cut-off, HRD) or "LST$^{lo}$" (number of LSTs<cut-off, no HRD).

Sequence of BRCA1 and BRCA2 Genes in Tumor DNA
  BRCA1 (NM_007294.2) and BRCA2 (NM_000059.3) genes were screened by Enhanced Mismatch Mutation Analysis or by massive parallel sequencing. Variant validation was performed by Sanger sequencing according to standard protocols. Analysis was performed on hg18 version of the human genome. Pathogenicity of the missense mutations was assessed using the prediction algorithms (such as phyloP, Grantham, align GVGD, SIFT, MaxEnt and NNSPLICE HSF) available in the Alamut Visual software version 2.4 (Interactive Biosoftware, Rouen, France) and the prediction databases available on LOVD (67) and UMD (68). Mutations classified as Unknown Variant and of Uncertain Significance were not considered as pathogenic for analyses. Large rearrangements were searched by Multiplex Ligation-dependent Probe Amplification using SALSA MLPA probemix P002 BRCA1/2 kit (MRC-Holland).

Methylation of BRCA1 and RAD51C Promoters
  Methylation of the BRCA1 promoter was evaluated as previously described (28). Methylation of RAD51C promoter was evaluated by pyrosequencing according to the protocol in (69)

Transcriptomic Data
  Gene expression was analyzed on Affymetrix U133 Plus 2.0 whole-genome expression arrays and on Illumina Human WG-6 V3 BeadArrays, processed according to the corresponding protocols. Raw data for Affymetrix platform were normalized using the brainarray CDF and GC-RMA normalization. Illumina expression data were normalized using Illumina BeadStudio with standard settings. All other analyses were done with R 2.15.1 statistical computing suite.

Molecular Subtypes in TCGA Cohort

For molecular subtyping of TCGA invasive breast carcinomas RPKM (reads per kilobase of transcript per million reads mapped) gene expression summary from RNA-seq data were used. Triple-negative molecular subtype was identified based on the tumor clustering using the set of genes defined by Sorlie and Coll. (36). HER2+ tumors were identified based on the expression of ERBB2, taking into account the proliferation score and copy number at the gene locus. Proliferation scores were obtained using the first principal component scores of the analysis of the gene set containing E2F1 targets. Extreme gene overexpression or moderate overexpression and amplified gene locus called HER2+ subtype. TCGA tumor clinical annotation was used for confirmation. Discordant annotations comprised 6% (28/467).

Detection of BRCA1 or RAD51C Promoter Methylation in the TCGA Cohort

Probesets related to BRCA1 and RAD51C genes were extracted from HumanMethylation27 and HumanMethylation450 (Illumina Infinium Beadchip arrays) gene methylation TCGA datasets. High value of probe cg04658354 and BRCA1 extreme down-regulation together with high proliferation score called the sample as having BRCA1 promoter methylation. RAD51C methylation probeset signals were irrelevant to the measured feature and were ignored; RAD51C extreme down-regulation together with high proliferation score called samples with RAD51C promoter methylation.

Deleterious Mutation Call in TCGA

Each sequence variant detected in tumors by exome sequencing was considered together with alternative allele frequency (in normal and in tumor), tumor allelic content and contamination detected from SNP-arrays. Missense mutations classified as Unknown Variant and of Uncertain Significance were considered as non-pathogenic.

Statistics

Confidence intervals were calculated using Clopper-Pearson Exact method for proportions.

Results

High Number of LST Identifies HRD in Invasive Breast Carcinomas

In order to evaluate HRD in different subtypes of breast carcinomas, a discovery set of 57 HER2-amplified and 399 luminal tumors with high quality SNP-array profiles was assembled. This set contained 43 hereditary breast cancers collected from germline mutations carriers (16 and 27 BRCA1 and BRCA2, respectively) and 28 from patients with a familial history of breast cancer who tested negative for BRCA1/2. Tumor ploidy was inferred from the absolute copy number profiles, identifying 317 near-diploid and 139 near-tetraploid tumors. The number of Large-scale State Transitions (LSTs) was evaluated for each tumor. Based on ploidy-specific cut-offs defined for TNBC (i.e. 15 and 20 LSTs for near-diploid and near-tetraploid tumors, respectively), tumors were classified as $LST^{hi}$ (55 cases, 27 near-diploid and 28 near-tetraploid tumors) or as $LST^{lo}$ (401 cases, 290 near-diploid and 111 near-tetraploid tumors). The status of the BRCA1 and BRCA2 genes were investigated in both "$LST^{hi}$" and "$LST^{lo}$" groups, following the hypothesis that LST signature is a surrogate marker of HRD, defining genomic HRD ($LST^{hi}$) or non-HRD ($LST^{lo}$).

Exploring the Origin of HRD in Tumors Classified as $LST^{hi}$

The majority of $LST^{hi}$ tumors in the discovery cohort were related to known BRCA1 or BRCA2 germline mutation (36/55) and reciprocally, the majority of known BRCA1 or BRCA2 germline mutated tumors were classified as $LST^{hi}$ (16/16 BRCA1 and 20/27 BRCA2 cases). The status of the second allele of the corresponding gene was evaluated by re-sequencing and/or genotyping and confirmed to be inactivated in the majority of cases (13/16 and 19/20 for BRCA1 and BRCA2 cases, respectively). The origin of HRD was investigated in the 23 $LST^{hi}$ cases, including 4 cases with germline BRCA mutations and retention of heterozygosity (ROH) at the corresponding locus, 2 cases with familial history which tested negative for BRCA mutations, and 16 cases not tested for mutations. In one case, the origin of HRD was provided by the genomic profile displaying a clear bi-allelic deletion at the BRCA2 locus. BRCA1 and BRCA2 mutations were searched for by massively parallel sequencing or by a heteroduplex detection method in 15 tumors with available tumor DNA (14 not tested previously and 1 with germline BRCA2 mutation). Altogether 10 tumors were found and validated to have bi-allelic alteration in BRCA: 7 cases with deleterious mutations in BRCA2 and 1 case with missense BRCA1 mutation (of unknown significance), all associated with loss of the corresponding wild-type allele; 1 case with two BRCA2 nonsense mutations, presumably in trans; and 1 somatic BRCA2 deleterious mutation in addition to the germline one. No deleterious BRCA mutation or large rearrangements of these genes was found in the remaining five cases. BRCA1 promoter methylation was further searched for in 4 of these cases with available material and found positive in one case. Epigenetic inactivation of RAD51C was shown to occur in some high-grade serous ovarian carcinomas and associated with HRD (70), thus methylation of RAD51C promoter was also considered in this discovery cohort. The only two extreme down-regulated RAD51C cases corresponded to the 2 $LST^{hi}$ unexplained cases (2/326 with available transcriptomic data) and direct demonstration of methylation of RAD51C promoter was obtained in both cases. Interestingly, one of these cases was the tumor from a BRCA2 mutation carrier without BRCA2 inactivation due to the retention of the wild-type BRCA2 allele in the tumor. In conclusion, the large majority of the 48 extensively evaluated $LST^{hi}$ tumors carried an identified cause of HRD (44/48, 92%), including 12 de-novo cases without a familial history (out of 15 tested).

Exploring HRD in Tumors Classified as $LST^{lo}$

Figure 11:
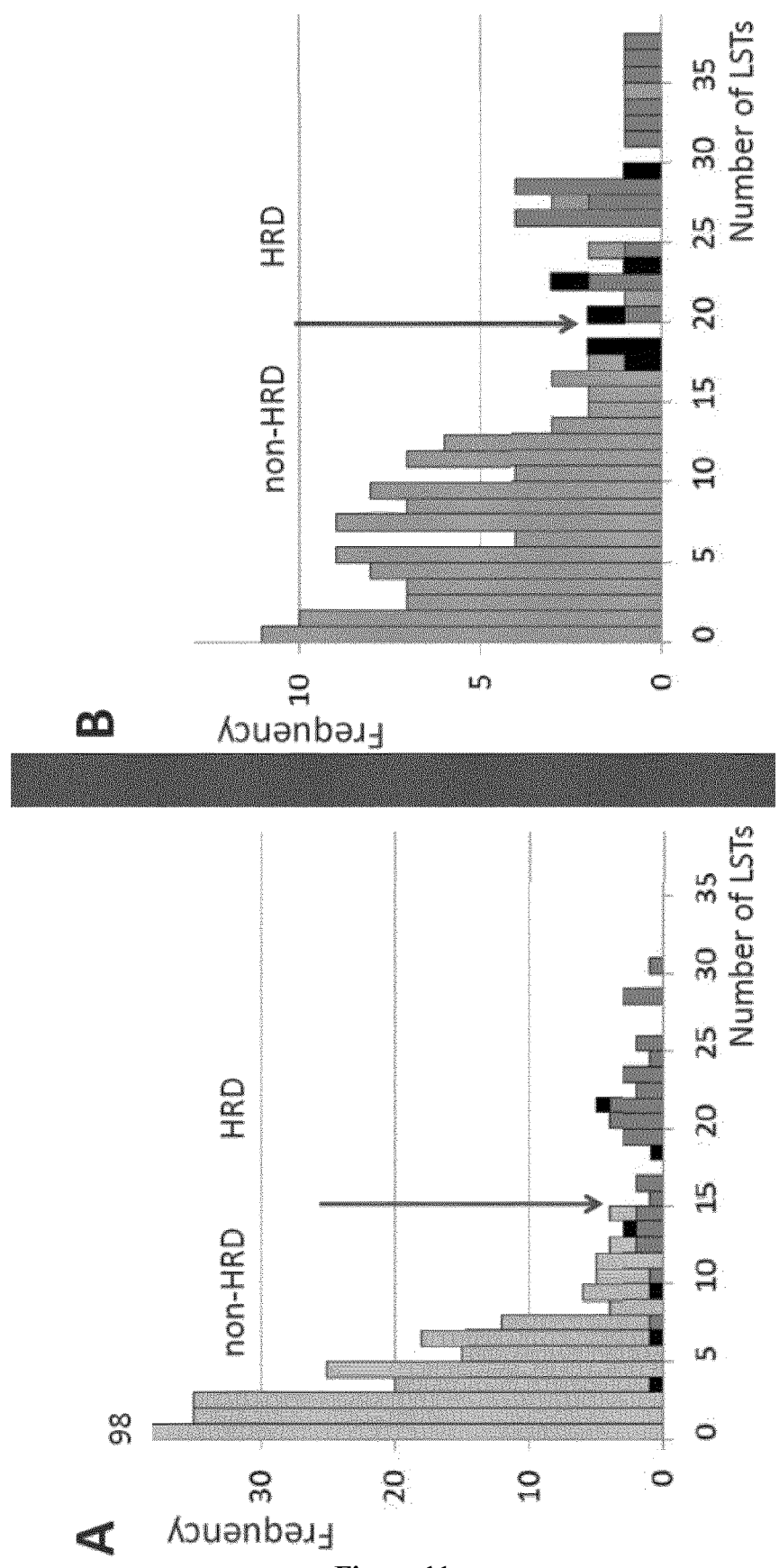
FIG. 11. LST number distribution in discovery cohort. Illustrated is a diagram showing number distribution in a discovery cohort of 456 breast carcinomas (399 luminal and 57 HER2-amplified tumors). X axis corresponds to the number of LSTs detected in the tumor genomic profile. Y axis corresponds to the number of cases. Arrow corresponds to the cut-off between non-HRD and HRD cases as previously defined in TNBC.

The vast majority of 401 $LST^{lo}$ tumors had no evidence of BRCA germline mutations, and no evidence of RAD51C down-regulation was found in this subgroup. Nevertheless, the $LST^{lo}$ subgroup contained 2 cases with a clear bi-allelic BRCA2 deletion and 7 cases from BRCA2 mutation carriers (none from BRCA1 mutation carrier). The status of the BRCA2 second allele was evaluated by re-sequencing and/or genotyping. In two cases, the BRCA2 locus displayed ROH and complete BRCA2 screening of the tumor DNA revealed no additional mutations. In one case, the BRCA2 locus displayed loss of heterozygosity (LOH) due to the loss of the mutated allele. In the 4 remaining cases, loss of the wildtype allele was confirmed. Interestingly, these 4 cases were near-diploid tumors with 12 or 13 LSTs, which were close to the HRD-defining cut-off of 15 LSTs. Consequently, additional effort was made to characterize cases with LST number immediately below the ploidy-specific cut-offs. Ten cases with available material were investigated by massively parallel sequencing. Two cases were found mutated for BRCA2 (with LOH at the corresponding locus): one nonsense mutation and one missense mutation with unknown significance. BRCA1 promoter methylation was examined in six of these borderline cases and found positive in one case. No evidence of inactivation of BRCA1 or BRCA2 was found in the 7 remaining tumors. Overall, only 8 cases with evidence of BRCA inactivation were found among the 401 $LST^{lo}$ tumors, including 6 near-diploid tumors with LST number close to the cut-off defining genomic HRD and 2 exceptional cases with bi-allelic BRCA2 deletions but with low LST number (7 and 10) (FIG. 11; Table 6).

lar characterization with comprehensive sequencing data available represent major advantages of this series. TCGA data were analyzed using the same approach as the one used on the discovery set that is genomic classification of tumors into HRD (59 $LST^{hi}$) and non-HRD (408 $LST^{lo}$) completed by assessment of the mutational status of the BRCA1/2 genes and by the level of expression/promoter methylation of BRCA1 and RAD51C.

The $LST^{hi}$ group contained 59 total cases divided into: 16 cases with BRCA1 promoter methylation; 14 cases with deleterious BRCA1 (9 cases) or BRCA2 (5 cases) mutations

TABLE 6

HRD in luminal and HER2+ breast tumors in the discovery cohort

| | | $LST^{hi}$ true positive | | $LST^{lo}$ false positive |
|---|---|---|---|---|
| Proven HRD | 31 | BRCA GL mutation + wt allele loss | 4 | BRCA GL mutation + wt allele loss |
| | 1 | *BRCA GL mutation + somatic mutation | | |
| | 7 | BRCA tum mutation + wt allele loss | 1 | BRCA tum mutation + wt allele loss |
| | 1 | *2BRCA2 mutations in tumor | | |
| | 1 | BRCA2 bi-allelic deletion | 2 | BRCA2 bi-allelic deletion |
| | 1 | BRCA1 promoter methylation | 1 | BRCA1 promoter methylation |
| | 2 | **RAD51C promoter methylation | | |
| | 44 | total | 8 | total |

| | | false positive | | true negative |
|---|---|---|---|---|
| No detected HRD (or not tested) | 3 | BRCA GL mutation + retention of wt allele | 2 | BRCA GL mutation + retention of wt allele |
| | | | 1 | BRCA GL mutation + mutated allele loss |
| | | | 1 | ***BRCA tumor mutation + missense |
| | 2 | ***BRCA missense mutation + wt allele loss | 1 | ***BRCA missense mutation + wt allele loss |
| | 2 | ****neither BRCA nor RAD51C alteration | 2 | Neither BRCA nor RAD51C alteration |
| | 4 | Not determined or not tested | 386 | Not determined or not tested |
| | 11 | Total | 393 | Total |
| Total | 55 | | 401 | |

*presumably mutations in trans
**including one case with germline mutation and ROH
***mutations of unknown significance
****no large rearrangement
GL: Germline;
wt: wild-type;
mutation: deleterious sequence variant if not otherwise specified;
HRD: homologous recombination deficiency.

Figure 12:
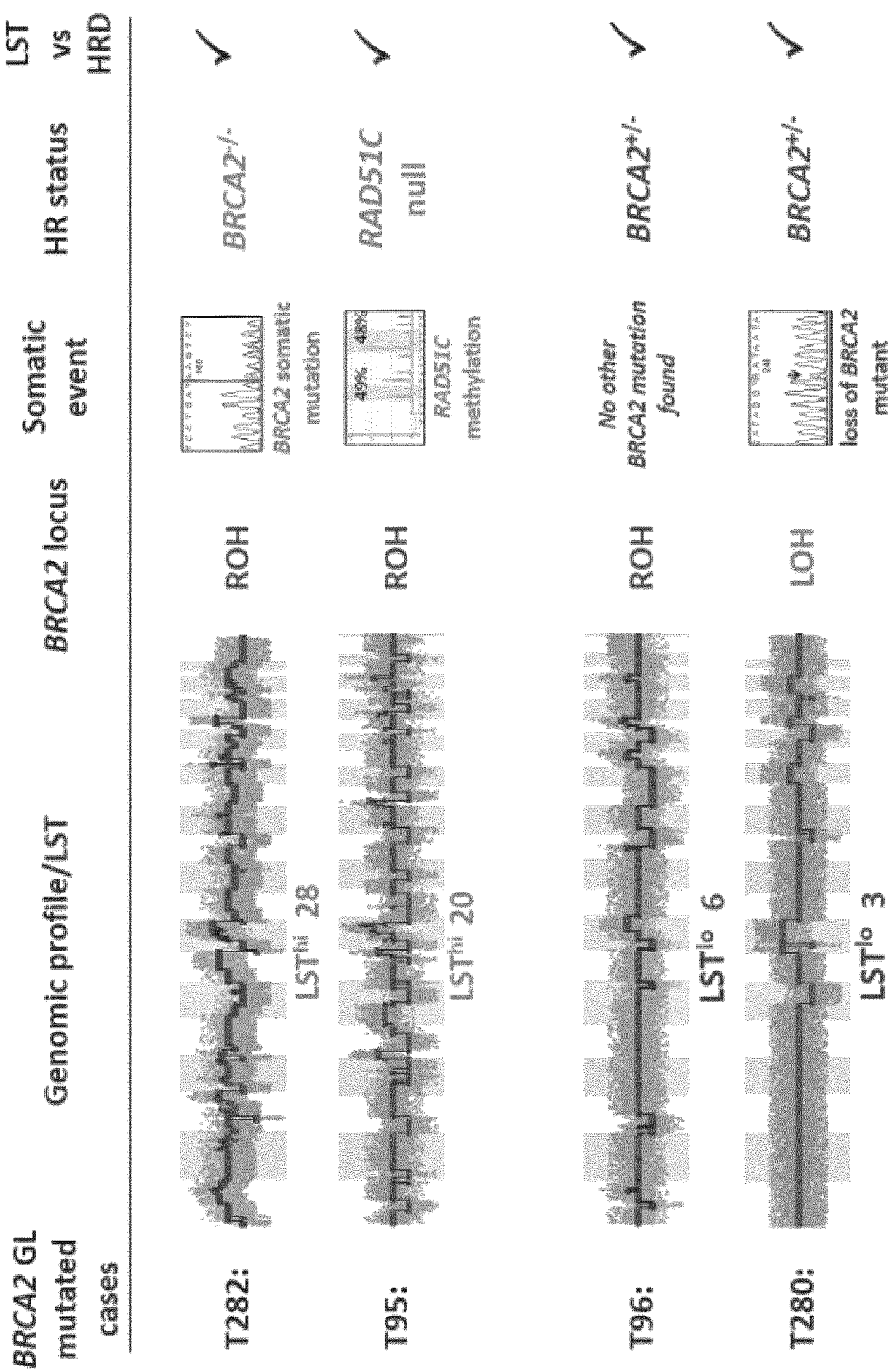
FIG. 12. Tumor status for HRD assessment. Illustrated is four examples of tumors with germline BRCA2 mutations clarified by LST status in which the genomic profile outline is shown with corresponding LST number. From top to bottom, (i) a case with $LST^{hi}$ status, Retention of Heterozygosity (ROH) status of BRCA2 in the tumor and a somatic deleterious mutation of the BRCA2 second allele; (ii) a case with $LST^{hi}$ status, ROH of BRCA2, no somatic BRCA2 mutation and methylation of the RAD51C promoter (pyrosequencing profile is shown); (iii) a case with $LST^{lo}$ status, ROH in the BRCA2 locus and no additional mutation found; (iv) a case with $LST^{lo}$ status, Loss of Heterozygosity (LOH) of the BRCA2 locus and the loss of the mutated allele (electophoregram is shown).

Thus, 44/55 (80%) $LST^{hi}$ tumors and 8/401 (2%) $LST^{lo}$ were found inactivated for BRCA1, BRCA2 or RAD51C in this large discovery set, including 11 BRCA inactivated $LST^{hi}$ cases without a familial history and conversely, 3 $LST^{lo}$ cases in BRCA1 or BRCA2 mutant carriers with retention of the corresponding wild-type allele in the tumor (FIG. 12).

The LST Signature Identifies HRD in the Validation Set

In order to validate the findings, the subset of 467 tumors with high quality SNP-array, methylation and expression profiles as well as tumor/normal sequencing data were selected from TCGA invasive breast carcinoma dataset. The wide diversity of histological subtypes, such as basal-like/ triple negative, mucinous, lobular, medullary and papillary carcinomas included in this series and the extensive molecutogether with loss of the wildtype allele of the corresponding gene (both supported by the appropriate mutated allele frequency in the exome sequencing data and by LOH in the genomic profiles); 1 case with 2 deleterious mutations in BRCA2 (presumably in trans); 4 cases with homozygous deletions of BRCA1 (2 cases) or BRCA2 (2 cases); 3 cases with BRCA1 deleterious missense mutations and LOH; 3 cases with RAD51C downregulation presumably due to promoter methylation and 1 RAD51C germline truncating mutation with loss of the wild-type allele; and 17 unexplained cases, including 1 case with BRCA2 variant of unknown significance and LOH. In order to explain these unexplained $LST^{hi}$ cases with neither BRCA1/2 nor RAD51C inactivation, deleterious mutations associated with LOH were searched for in a set of genes involved in DNA damage response such as BRIP1, PALB2, RAD51 paralogs, ATM, ATR and WRN. No inactivation of these genes was found in the 17 $LST^{hi}$ unexplained cases. The few cases compatible with bi-allelic inactivation of FANCM (1 case), RAD51B (1 case), WRN (1 case) and ATM (6 cases) belonged to the $LST^{lo}$ subgroup. One tumor with an ATM deleterious mutation was also inactivated for BRCA1, which is the most probable explanation for its $LST^{hi}$ status. 36 cases were found amplified in EMSY (c11orf30) loci, which has been described associated with BRCA2 function (71). However, only two cases with EMSY amplification belonged to the $LST^{hi}$ subgroup, each with BRCA1 or BRCA2 inactivation (Table 7).

Overall, $LST^{hi}$ status was associated with identified cause of HRD in 73% (43/59) cases; while only 1.2% (5/408) of the tumors classified as $LST^{lo}$ were altered in BRCA1/2 genes. Thus, the performance of the LST signature in the whole TCGA cohort of invasive breast carcinomas was 73% sensitivity and 98% specificity.

HRD in the Main Breast Cancer Histological Subtypes

The incidence and origin of HRD as well as the performance of the LST genomic signature in HRD prediction were assessed for each of the main breast cancer subtypes, namely triple negative, luminal and HER2+ tumors (Table 8). Analyses were independently performed in the discovery

TABLE 7

HRD in the TCGA validation cohort in all major subtypes of breast tumors: TNBC, luminal and HER2+

|  | | $LST^{hi}$ true positive | | $LST^{lo}$ false positive |
|---|---|---|---|---|
| Proven HRD | 14 | BRCA GL mutation + wt allele loss | 3 | BRCA mutation + wt allele loss |
|  | 1 | 2 BRCA mutations | 1 | *BRCA mutation + missense |
|  | 4 | BRCA bi-allelic deletion | | |
|  | 3 | *BRCA missense mutation + wt allele loss | | |
|  | 16 | BRCA1 promoter methylation | 1 | BRCA1 promoter methylation |
|  | 3 | RAD51C promoter methylation | | |
|  | 1 | **RAD51C mutation + wt allele loss | | |
|  | 42 | total | 5 | total |

|  | | false positive | | true negative |
|---|---|---|---|---|
| No detected HRD | 1 | BRCA GL mutation + retention of wt allele | 1 | BRCA mutation + retention of wt allele |
|  | 3 | **BRCA missense mutation + wt allele loss | 6 | **BRCA missense mutation + wt allele loss |
|  |  |  | 1 | **BRCA in-frame deletion + wt allele loss |
|  |  |  | 2 | **BRCA missense mutations |
|  | 13 | neither BRCA nor RAD51C alteration | 393 | Neither BRCA nor RAD51C alteration |
|  | 17 | Total | 403 | Total |
| Total |  | 59 |  | 408 |

*classified as deleterious
**mutations of unknown significance
wt: wild-type;
mutation: deleterious sequence variant if not otherwise specified;
HRD: homologous recombination deficiency.

The $LST^{lo}$ subgroup contained 5 cases with evidence of BRCA1 and BRCA2 alterations, namely one case with BRCA1 methylation and 4 mutated cases with losses of the corresponding wild-type allele: a BRCA2 in-frame deletion, a BRCA2 nonsense mutation (Y3308*), a BRCA1 splicing mutation and a BRCA2 frameshift mutation. No evidence of BRCA associated HRD was found in the 403 remaining cases.

(in-house) and TCGA cohorts. The rates and causes of HRD were found to be similar in the TCGA and discovery cohorts, when cases with familial history of disease were removed from the latter (no significant difference by Fisher's and Chi-square tests in the rates and distributions). For clarity, results are further described from the combined cohorts (Table 8).

TABLE 8

Rate and origin of HRD in breast cancer subtypes

| | | BRCA1 mut/del | BRCA1 meth | BRCA2 mut/del | RAD51C meth/mut | ND** | Total LST$^{hi}$ | Total LST$^{lo}$ (FN) | Rate HRD |
|---|---|---|---|---|---|---|---|---|---|
| | Discovery* | 14 | 8 | 5 | 0 | 6 | 33 | 20 (0) | 33/53 (62%) |
| | TCGA | 10 | 13 | 3 | 3 | 6 | 36 | 43 (1) | 36/79 (46%) |
| TNBC | | | | | | | | | 69/132 |
| | Total | 24 (35%) | 21 (30%) | 8 (12%) | 3 (4%) | 13 (19%) | 69 | 63 (1) | 52% |
| | | | | | | | | | 95% CI 43-61% |
| | Discovery* | 1 | 0 | 7 | 1 | 3 | 12 | 320 (3) | 12/332 (4%) |
| | TCGA | 5 | 1 | 5 | 1 | 6 | 18 | 311 (4) | 18/329 (5%) |
| Luminal | | | | | | | | | 30/661 |
| | Total | 6 (20%) | 1 (3%) | 12 (40%) | 2 (7%) | 9 (30%) | 30 | 631 (6) | 5% |
| | | | | | | | | | 95% CI 3-6% |
| | Discovery* | 0 | 0 | 2 | 0 | 3 | 5 | 48 (0) | 2/53 (4%)*** |
| | TCGA | 1 | 0 | 0 | 0 | 4 | 5 | 54 (1) | 1/59 (2%)*** |
| HER2+ | | | | | | | | | 3/112*** |
| | Total | 1 (10%) | 0 | 2 (20%) | 0 | 7 (70%) | 10 | 102 (1) | 3%*** |
| | | | | | | | | | 95% CI 1-8%*** |

*Cases with familial history were removed from the Discovery cohort.
**Including missense BRCA mutations with unknown significance, also predicted pathogenic.
***Rates of proven HRD are indicated.
TNBC: triple negative breast carcinoma; HER2+: tumors with HER2 amplification/over-expression; Meth: methylation of promoter; mut: mutated; ND: not determined; FN: false negative; HRD: homologous recombination deficiency; CI: confidence interval.

TNBC.

HRD defined by the LST genomic signature was found at a rate of 52% (69/132, 95% CI: 43-61%). Most of the HRD cases were associated with inactivation of BRCA1, either by mutations/deletions (24/69, 35%) or by promoter methylation (23/69, 33%), and rarely by inactivation of BRCA2 (9/69, 13%) or RAD51C methylation (3/69, 4%). Prediction of LST signature obtained for TNBC corresponded to 85% sensitivity and 98% specificity (i.e. a single false negative case with BRCA1 methylation). Unexplained HRD comprised 10 cases (15%), which could include cases with undetected inactivation of HR genes.

Luminal Breast Tumors.

In the 661 luminal tumors, genomic HRD was detected in nearly 5% (30/661, 95% CI: 3-6%) of the cases. The most frequent cause of HRD was bi-allelic mutations and/or deletions of BRCA2 (12/30, 40%), then inactivation of BRCA1 (8/30, 26%) mostly by promoter methylation (6 out the 8 cases), and RAD51C promoter methylation (2/30, 7%). Results obtained for luminal breast tumors by the LST signature corresponded to 74% sensitivity and 99% specificity. The unexplained HRD ("false positives") comprised 8 cases, which included BRCA variants with unknown significance and BRCA2 deleterious mutations without loss of wild-type allele. Two false negative cases were actually not incompatible with intact BRCA1/2 function: a combination of deleterious missense and nonsense mutations (with low allelic frequency, possibly clonal) in BRCA1 and a BRCA2 variant with unknown clinical consequence (Y3308*). However, 5 false negative cases had proven inactivation of BRCA (2 BRCA2 homozygous deletions and 3 deleterious mutations with LOH) despite the absence of genomic HRD.

HER2 Breast Tumors.

Among 112 HER2-overexpressing tumors, genomic HRD was detected in 10 cases (10/112, 9%), including 3 cases with BRCA2 deleterious mutations (2 cases) and BRCA1 promoter methylation (1 case) (3/112 proven HRD cases, 95% CI: 1-8%). The performance of the LST signature in HER2+ tumors has a rather low sensitivity (3/10, 33%) due to rarity of HER2+ tumors with HRD and high proportion of false positives. The majority of false positives (5/7) represented the cases with LST number slightly above the threshold for HRD call. Comparison of the number of LSTs in high grade HER2+ tumors and high grade luminal tumors demonstrated an overall higher level of LSTs in HER2+ tumors, which may explain the high rate of false positive calls. One BRCA1 missense mutation, one BRCA2 missense mutations and one small in-frame deletion in BRCA2 (all with unknown significance and associated with loss of the wild-type corresponding allele) were classified as LST$^{lo}$, providing 100% specificity of the LST classifier in HER2+ tumors.

Most TNBC Responders to Cisplatin Pre-Operative Treatment Carry a High Number of LST HRD is linked to the response to platinum based chemotherapy. Birkbak et al. analyzed SNParray profiles from a series of 79 patients with TNBC, including 28 patients treated by cisplatin prior to surgery (Cisplatin-1 trial) and 51 patients treated with cisplatin in addition to bevacizumab (Cisplatin-2 trial) (59). The LST number was calculated for 54 tumors with acceptable quality of genomic profiles and showed 33 $LST^{hi}$ and 21 $LST^{lo}$ tumors. Comparison between LST number and the response to cisplatin preoperative treatment showed that the vast majority of the responders (assessed by the investigators as 4-5 in Miller-Payne response score) were classified as HRD displaying a high LST number (18/33 vs 1/21, p-value <0.0001, Fisher's exact test); pathological Complete Response (pCR) occurred for 11 tumors, all classified as $LST^{hi}$ (p-value <0.003, Fisher's exact test) (Table 9).

TABLE 4

Cisplatin response in TNBC neo-adjuvant setting

| Miller Payne Response Score | HRD/$LST^{hi}$ | HRD/$LST^{lo}$ | |
|---|---|---|---|
| Non Responders (0-3) | 15 | 20 | P < 0.0001 |
| Responders (4-5) | 18 | 1 | |
| 4 (CR) | 7 | 1 | |
| 5 (pCR) | 11 | 0 | |

REFERENCES

1. Rakha E A, Reis-Filho J S, Ellis I O: Basal-like breast cancer: a critical review. J Clin Oncol 26:2568-81, 2008
2. Dawson S J, Provenzano E, Caldas C: Triple negative breast cancers: clinical and prognostic implications. Eur J Cancer 45 Suppl 1:27-40, 2009
3. Foulkes W D, Stefansson I M, Chappuis P O, et al: Germline BRCA1 mutations and a basal epithelial phenotype in breast cancer. J Natl Cancer Inst 95:1482-5, 2003
4. Bergamaschi A, Kim Y H, Wang P, et al: Distinct patterns of DNA copy number alteration are associated with different clinicopathological features and gene-expression subtypes of breast cancer. Genes Chromosomes Cancer 45:1033-40, 2006
5. Melchor L, Honrado E, Garcia M J, et al: Distinct genomic aberration patterns are found in familial breast cancer associated with different immunohistochemical subtypes. Oncogene 27:3165-75, 2008
6. Natrajan R, Weigelt B, Mackay A, et al: An integrative genomic and transcriptomic analysis reveals molecular pathways and networks regulated by copy number aberrations in basal-like, HER2 and luminal cancers. Breast Cancer Res Treat, 2009
7. Gudmundsdottir K, Ashworth A: The roles of BRCA1 and BRCA2 and associated proteins in the maintenance of genomic stability. Oncogene 25:5864-74, 2006
8. Roy R, Chun J, Powell S N: BRCA1 and BRCA2: different roles in a common pathway of genome protection. Nat Rev Cancer 12:68-78, 2012
9. Turner N, Tutt A, Ashworth A: Hallmarks of 'BRCAness' in sporadic cancers. Nat Rev Cancer 4:814-9, 2004
10. Chin S F, Teschendorff A E, Marioni J C, et al: High-resolution aCGH and expression profiling identifies a novel genomic subtype of ER negative breast cancer. Genome Biol 8:R215, 2007
11. Stefansson O A, Jonasson J G, Johannsson O T, et al: Genomic profiling of breast tumours in relation to BRCA abnormalities and phenotypes. Breast Cancer Res 11:R47, 2009
12. Joosse S A, Brandwijk K I, Mulder L, et al: Genomic signature of BRCA1 deficiency in sporadic basal-like breast tumors. Genes Chromosomes Cancer 50:71-81, 2011
13. Farmer H, McCabe N, Lord C J, et al: Targeting the DNA repair defect in BRCA mutant cells as a therapeutic strategy. Nature 434:917-21, 2005
14. Bryant H E, Schultz N, Thomas H D, et al: Specific killing of BRCA2-deficient tumours with inhibitors of poly(ADP-ribose) polymerase. Nature 434:913-7, 2005
15. Fong P C, Boss D S, Yap T A, et al: Inhibition of poly(ADP-ribose) polymerase in tumors from BRCA mutation carriers. N Engl J Med 361:123-34, 2009
16. Vollebergh M A, Jonkers J, Linn S C: Genomic instability in breast and ovarian cancers: translation into clinical predictive biomarkers. Cell Mol Life Sci 69:223-45, 2012
17. Focken T, Steinemann D, Skawran B, et al: Human BRCA1-Associated Breast Cancer: No Increase in Numerical Chromosomal Instability Compared to Sporadic Tumors. Cytogenet Genome Res 135:84-92, 2011
18. Johannsdottir H K, Jonsson G, Johannesdottir G, et al: Chromosome 5 imbalance mapping in breast tumors from BRCA1 and BRCA2 mutation carriers and sporadic breast tumors. Int J Cancer 119:1052-60, 2006
19. Tirkkonen M, Johannsson O, Agnarsson B A, et al: Distinct somatic genetic changes associated with tumor progression in carriers of BRCA1 and BRCA2 germ-line mutations. Cancer Res 57:1222-7, 1997
20. Melchor L, Alvarez S, Honrado E, et al: The accumulation of specific amplifications characterizes two different genomic pathways of evolution of familial breast tumors. Clin Cancer Res 11:8577-84, 2005
21. Wessels L F, van Welsem T, Hart A A, et al: Molecular classification of breast carcinomas by comparative genomic hybridization: a specific somatic genetic profile for BRCA1 tumors. Cancer Res 62:7110-7, 2002
22. Waddell N, Arnold J, Cocciardi S, et al: Subtypes of familial breast tumours revealed by expression and copy number profiling. Breast Cancer Res Treat, 2009
23. Jonsson G, Staaf J, Vallon-Christersson J, et al: Genomic subtypes of breast cancer identified by array-comparative genomic hybridization display distinct molecular and clinical characteristics. Breast Cancer Res 12:R42, 2010
24. Joosse S A, van Beers E H, Tielen I H, et al: Prediction of BRCA1-association in hereditary non-BRCA1/2 breast carcinomas with array-CGH. Breast Cancer Res Treat 116:479-89, 2009
25. Lips E H, Mulder L, Hannemann J, et al: Indicators of homologous recombination deficiency in breast cancer and association with response to neoadjuvant chemotherapy. Ann Oncol 22:870-6, 2011
26. Vollebergh M A, Lips E H, Nederlof P M, et al: An aCGH classifier derived from BRCA1-mutated breast cancer and benefit of high-dose platinum-based chemotherapy in HER2-negative breast cancer patients. Ann Oncol 22:1561-70, 2011
27. Popova T, Manie E, Stoppa-Lyonnet D, et al: Genome Alteration Print (GAP): a tool to visualize and mine complex cancer genomic profiles obtained by SNP arrays. Genome Biol 10:R128, 2009
28. Manie E, Vincent-Salomon A, Lehmann-Che J, et al: High frequency of TP53 mutation in BRCA1 and sporadic basal-like carcinomas but not in BRCA1 luminal breast tumors. Cancer Res 69:663-71, 2009
29. Vincent-Salomon A, Gruel N, Lucchesi C, et al: Identification of typical medullary breast carcinoma as a 29. genomic sub-group of basal-like carcinomas, a heterogeneous new molecular entity. Breast Cancer Res 9:R24, 2007
30. Marty B, Maire V, Gravier E, et al: Frequent PTEN genomic alterations and activated phosphatidylinositol 3-kinase pathway in basal-like breast cancer cells. Breast Cancer Res 10:R101, 2008
31. Azoulay S, Lae M, Freneaux P, et al: KIT is highly expressed in adenoid cystic carcinoma of the breast, a basal-like carcinoma associated with a favorable outcome. Mod Pathol 18:1623-31, 2005
32. Nielsen T O, Hsu F D, Jensen K, et al: Immunohistochemical and clinical characterization of the basal-like subtype of invasive breast carcinoma. Clin Cancer Res 10:5367-74, 2004
33. Esteller M, Silva J M, Dominguez G, et al: Promoter hypermethylation and BRCA1 inactivation in sporadic breast and ovarian tumors. J Natl Cancer Inst 92:564-9, 2000
34. Houdayer C, Moncoutier V, Champ J, et al: Enhanced mismatch mutation analysis: simultaneous detection of point mutations and large scale rearrangements by capillary electrophoresis, application to BRCA1 and BRCA2. Methods Mol Biol 653:147-80, 2010
35. Dai M, Wang P, Boyd A D, et al: Evolving gene/transcript definitions significantly alter the interpretation of GeneChip data. Nucleic Acids Res 33:e175, 2005
36. Sorlie T, Tibshirani R, Parker J, et al: Repeated observation of breast tumor subtypes in independent gene expression data sets. Proc Natl Acad Sci USA 100:8418-23, 2003
37. Staaf J, Vallon-Christersson J, Lindgren D, et al: Normalization of Illumina Infinium whole-genome SNP data improves copy number estimates and allelic intensity ratios. BMC Bioinformatics 9:409, 2008
38. Waddell N, Arnold J, Cocciardi S, et al: Subtypes of familial breast tumours revealed by expression and copy number profiling. Breast Cancer Res Treat 123:661-77, 2010
39. DeRose Y S, Wang G, Lin Y C, et al: Tumor grafts derived from women with breast cancer authentically reflect tumor pathology, growth, metastasis and disease outcomes. Nat Med 17:1514-20, 2011
40. Storchova Z, Kuffer C: The consequences of tetraploidy and aneuploidy. J Cell Sci 121:3859-66, 2008
41. Young S R, Pilarski R T, Donenberg T, et al: The prevalence of BRCA1 mutations among young women with triple-negative breast cancer. BMC Cancer 9:86, 2009
42. Elstrodt F, Hollestelle A, Nagel J H, et al: BRCA1 mutation analysis of 41 human breast cancer cell lines reveals three new deleterious mutants. Cancer Res 66:41-5, 2006
43. Xu J, Huo D, Chen Y, et al: CpG island methylation affects accessibility of the proximal BRCA1 promoter to transcription factors. Breast Cancer Res Treat 120:593-601, 2010
44. Sjoblom T, Jones S, Wood L D, et al: The consensus coding sequences of human breast and colorectal cancers. Science 314:268-74, 2006
45. Garcia A I, Buisson M, Bertrand P, et al: Downregulation of BRCA1 expression by miR-146a and miR-146b-5p in triple negative sporadic breast cancers. EMBO Mol Med 3:279-90, 2011
46. Moskwa P, Buffa F M, Pan Y, et al: miR-182-mediated downregulation of BRCA1 impacts DNA repair and sensitivity to PARP inhibitors. Mol Cell 41:210-20, 2011
47. Plo I, Laulier C, Gauthier L, et al: AKT1 inhibits homologous recombination by inducing cytoplasmic retention of BRCA1 and RAD51. Cancer Res 68:9404-12, 2008
48. Van Loo P, Nordgard S H, Lingjaerde O C, et al: Allele-specific copy number analysis of tumors. Proc Natl Acad Sci USA 107:16910-5, 2010
49. Pujana M A, Han J D, Starita L M, et al: Network modeling links breast cancer susceptibility and centrosome dysfunction. Nat Genet 39:1338-49, 2007
50. Xu X, Weaver Z, Linke S P, et al: Centrosome amplification and a defective G2-M cell cycle checkpoint induce genetic instability in BRCA1 exon 11 isoform-deficient cells. Mol Cell 3:389-95, 1999
51. Brodie K M, Henderson B R: Characterization of BRCA1 centrosome targeting, dynamics and function: A role for the nuclear export signal, CRM1 and Aurora A kinase. J Biol Chem, 2012
52. Kais Z, Parvin J D: Regulation of centrosomes by the BRCA1-dependent ubiquitin ligase. Cancer Biol Ther 7:1540-3, 2008
53. Moller P, Hagen A I, Apold J, et al: Genetic epidemiology of BRCA mutations—family history detects less than 50% of the mutation carriers. Eur J Cancer 43:1713-7, 2007
54. O'Shaughnessy J, Telli M, Swain S, et al: Phase 3 Study of Iniparib (I) Plus Gemcitabine (G) and Carboplatin (C) in Metastatic Triple-negative Breast Cancer (mTNBC)—Results of an Exploratory Analysis by Prior Therapy European Journal of Cancer 47:S338, 2011
55. Miki Y, Swensen J, Shattuck-Eidens D, Futreal P A, Harshman K, Tavtigian S, Liu Q, Cochran C, Bennett L M, Ding W and et al. (1994). A strong candidate for the breast and ovarian cancer susceptibility gene BRCA1. Science, 266, 66-71.
56. Wooster R, Bignell G, Lancaster J, Swift S, Seal S, Mangion J, Collins N, Gregory S, Gumbs C and Micklem G. (1995). Identification of the breast cancer susceptibility gene BRCA2. Nature, 378, 789-92.
57. Esteller M, Silva J M, Dominguez G, Bonilla F, Matias-Guiu X, Lerma E, Bussaglia E, Prat J, Harkes I C, Repasky E A, Gabrielson E, Schutte M, Baylin S B and Herman J G. (2000). Promoter hypermethylation and BRCA1 inactivation in sporadic breast and ovarian tumors. J Natl Cancer Inst, 92, 564-9.
58. Stephens P J, McBride D J, Lin M L, Varela I, Pleasance E D, Simpson J T, Stebbings L A, Leroy C, Edkins S, Mudie L J, Greenman C D, Jia M, Latimer C, Teague J W, Lau K W, Burton J, Quail M A, Swerdlow H, Churcher C, Natrajan R, Sieuwerts A M, Martens J W, Silver D P, Langerod A, Russnes H E, Foekens J A, Reis-Filho J S, van 't Veer L, Richardson A L, Borresen-Dale A L, Campbell P J, Futreal P A and Stratton M R. (2009). Complex landscapes of somatic rearrangement in human breast cancer genomes. Nature, 462, 1005-10.
59. Birkbak, N. J., Wang, Z. C., Kim, J. Y., Eklund, A. C., Li, Q., Tian, R., Bowman-Colin, C., Li, Y., Greene-Colozzi, A., Iglehart, J. D., et al. (2012). Telomeric allelic imbalance indicates defective DNA repair and sensitivity to DNA-damaging agents. Cancer Discovery 2, 366-375.
60. Lee, M.-N., Tseng, R.-C., Hsu, H.-S., Chen, J.-Y., Tzao, C., Ho, W. L., and Wang, Y.-C. (2007). Epigenetic inactivation of the chromosomal stability control genes BRCA1, BRCA2, and XRCC5 in non-small cell lung cancer. Clin. Cancer Res. 13, 832-838.
61. Pecuchet N, Popova T, Manie E, Lucchesi C, Battistella A, Vincent-Salomon A, et al. Loss of heterozygosity at 13q13 and 14q32 predicts BRCA2 inactivation in luminal breast carcinomas. Int J Cancer. 2013; 133:2834-42.
62. Popova T, Hebert L, Jacquemin V, Gad S, Caux-Moncoutier V, Dubois-d'Enghien C, et al. Germline BAP1 mutations predispose to renal cell carcinomas. Am J Hum Genet. 2013; 92:974-80.
63. Vincent-Salomon A, Gruel N, Lucchesi C, MacGrogan G, Dendale R, Sigal-Zafrani B, et al. Identification of typical medullary breast carcinoma as a genomic subgroup of basal-like carcinomas, a heterogeneous new molecular entity. Breast Cancer Res. 2007; 9:R24.
64. Servant N, Bollet M A, Halfwerk H, Bleakley K, Kreike B, Jacob L, et al. Search for a gene expression signature of breast cancer local recurrence in young women. Clin Cancer Res. 2012; 18:1704-15.
65. Vincent-Salomon A, Benhamo V, Gravier E, Rigaill G, Gruel N, Robin S, et al. Genomic instability: a stronger prognostic marker than proliferation for early stage luminal breast carcinomas. PLoS One. 2013; 8:e76496.
66. Birkbak N J, Wang Z C, Kim J Y, Eklund A C, Li Q, Tian R, et al. Telomeric allelic imbalance indicates defective DNA repair and sensitivity to DNA-damaging agents. Cancer Discov. 2012; 2:366-75.
67. Fokkema I F, Taschner P E, Schaafsma G C, Celli J, Laros J F, den Dunnen J T. LOVD v.2.0: the next generation in gene variant databases. Hum Mutat. 2011; 32:557-63.
68. Caputo S, Benboudjema L, Sinilnikova O, Rouleau E, Beroud C, Lidereau R, et al. Description and analysis of genetic variants in French hereditary breast and ovarian cancer families recorded in the UMD-BRCA1/BRCA2 databases. Nucleic Acids Res. 2012; 40:D992-1002.
69. Hansmann, T. Pliushch G, Leubner MKroll P, Endt D, Gehrig A, et al. Constitutive promoter methylation of BRCA1 and RAD51C in patients with familial ovarian cancer and early-onset sporadic breast cancer. Hum Mol Genet. 2012; 21:4669-79.
70. Abkevich V, Timms K M, Hennessy B T, Potter J, Carey M S, Meyer L A, et al. Patterns of genomic loss of heterozygosity predict homologous recombination repair defects in epithelial ovarian cancer. Br J Cancer. 2012; 107:1776-82.
71. Haber D A. The BRCA2-EMSY connection: implications for breast and ovarian tumorigenesis. Cell. 2003; 115:507-8.

The invention claimed is:

1. A method for treating cancer in a patient in need thereof, the method comprising:
   i) quantifying the number of large-scale transitions in the genomic DNA of a tumor sample obtained from said patient, a large-scale transition being a somatic copy number transition along the length of a chromosome between two genomic regions each at least 10 megabases in length after filtering out transitions between genomic regions shorter than 3 megabases in length;
   ii) sequencing genomic DNA of said tumor sample to determine the presence of germline or somatic DNA mutations in breast cancer 1 (BRCA1) and breast cancer 2 (BRCA2); and
   iii) administering a PARP inhibitor and/or an alkylating agent to said patient having a tumor sample comprising a cancer cell having at least 11 large-scale transitions per genome and a germline or somatic DNA mutation in either the BRCA1 gene or the BRCA2 gene.

2. A method for treating cancer in a patient in need thereof, the method comprising:
   i) quantifying the number of large-scale transitions in the genomic DNA of a tumor sample obtained from said patient, a large-scale transition being a somatic copy number transition along the length of a chromosome between two genomic regions each at least 10 megabases in length after filtering out transitions between genomic regions shorter than 3 megabases in length;
   ii) sequencing genomic DNA of said tumor sample to determine the presence of germline or somatic DNA mutations in BRCA1 and BRCA2; and
   iii) administering a PARP inhibitor and/or an alkylating agent to said patient having a tumor sample identified as comprising a cancer cell having at least 11 large-scale transitions per genome and a germline or somatic DNA mutation in either the BRCA1 gene or the BRCA2 gene.

3. A method for treating cancer in a patient in need thereof, the method comprising:
   i) quantifying the number of large-scale transitions in the genomic DNA of a tumor sample obtained from said patient, a large-scale transition being a somatic copy number transition along the length of a chromosome between two genomic regions each at least 10 megabases in length after filtering out transitions between genomic regions shorter than 3 megabases in length;
   ii) sequencing genomic DNA of said tumor sample to determine the presence of germline or somatic DNA mutations in BRCA1 and BRCA2; and
   iii) administering a PARP inhibitor and/or an alkylating agent to said patient having at least 11 large-scale transitions detected in step i) and a germline or somatic DNA mutation in either the BRCA1 gene or the BRCA2 gene has been detected in step ii).

4. The method of claim 1, wherein the cancer is selected from breast cancer, ovary cancer, pancreas cancer, head and neck carcinoma and melanoma.

5. The method of claim 2, wherein the cancer is selected from breast cancer, ovary cancer, pancreas cancer, head and neck carcinoma and melanoma.

6. The method of claim 3, wherein the cancer is selected from breast cancer, ovary cancer, pancreas cancer, head and neck carcinoma and melanoma.

7. The method of claim 1, wherein the cancer is breast cancer.

8. The method of claim 2, wherein the cancer is breast cancer.

9. The method of claim 3, wherein the cancer is breast cancer.

10. The method of claim 1, wherein the PARP inhibitor and/or alkylating agent is selected from the group consisting of olaparib, rucaparib, CEP 9722, MK 4827, BMN-673, 3-aminobenzamide, platinium complexes such as cisplatin, carboplatin and oxaliplatin, chlormethine, chlorambucil, melphalan, cyclophosphamide, ifosfamide, estramustine, carmustine, lomustine, fotemustine, streptozocin, busulfan, pipobroman, procarbazine, dacarabazine, thiotepa and temozolomide.

11. The method of claim 2, wherein the PARP inhibitor and/or alkylating agent is selected from the group consisting of olaparib, rucaparib, CEP 9722, MK 4827, BMN-673, 3-aminobenzamide, platinium complexes such as cisplatin, carboplatin and oxaliplatin, chlormethine, chlorambucil, melphalan, cyclophosphamide, ifosfamide, estramustine, carmustine, lomustine, fotemustine, streptozocin, busulfan, pipobroman, procarbazine, dacarabazine, thiotepa and temozolomide.

12. The method of claim 3, wherein the PARP inhibitor and/or alkylating agent is selected from the group consisting of olaparib, rucaparib, CEP 9722, MK 4827, BMN-673, 3-aminobenzamide, platinum complexes such as cisplatin, carboplatin and oxaliplatin, chlormethine, chlorambucil, melphalan, cyclophosphamide, ifosfamide, estramustine, carmustine, lomustine, fotemustine, streptozocin, busulfan, pipobroman, procarbazine, dacarabazine, thiotepa and temozolomide.

13. The method of claim 2, wherein step i) comprises quantifying the number of copy number variations per genome by sequencing, comparative genomic hybridization array or single nucleotide polymorphism array.

14. The method of claim 3, wherein step i) comprises quantifying the number of copy number variations per genome by sequencing, comparative genomic hybridization array or single nucleotide polymorphism array.

15. The method of claim 7, wherein said breast cancer is basal-like, luminal, or HER2-overexpressing breast carcinoma.

16. The method of claim 8, wherein said breast cancer is basal-like, luminal, or HER2-overexpressing breast carcinoma.

17. The method of claim 9, wherein said breast cancer is basal-like, luminal, or HER2-overexpressing breast carcinoma.

18. A method for treating cancer in a patient in need thereof, the method comprising:
   i) quantifying the number of large-scale transitions in the genomic DNA of a tumor sample obtained from said patient, a large-scale transition being a somatic copy number transition along the length of a chromosome between two genomic regions each at least 3 megabases in length;
   ii) sequencing genomic DNA of said tumor sample to determine the presence of germline or somatic DNA mutations in BRCA1, BRCA2 and at least one other gene of the homologous recombination (HR) pathway selected from partner and localizer of BRCA2 (PALB2/FANCN), BRCA1-interacting protein 1 (BRIP1/FANCJ), BRCA1-associated RING domain protein 1 gene (BARD1), Rad51 recombinase (RAD51) and RAD51 paralogs which are RAD51B, RAD51C, RAD51D, X-Ray Repair Cross Complementing 2 (XRCC2) and X-Ray Repair Cross Complementing 3 (XRCC3); and
   iii) administering a PARP inhibitor and/or an alkylating agent to said patient having a tumor sample comprising a cancer cell having at least one large-scale transition per genome or a germline or somatic DNA mutation in at least one of the HR pathway genes in step ii).

19. The method of claim 18, wherein the cancer is selected from breast cancer, ovary cancer, pancreas cancer, head and neck carcinoma and melanoma.

20. The method of claim 18, wherein the cancer is breast cancer.

21. The method of claim 18, wherein the PARP inhibitor and/or alkylating agent is selected from the group consisting of olaparib, rucaparib, CEP 9722, MK 4827, BMN-673, 3-aminobenzamide, platinum complexes such as cisplatin, carboplatin and oxaliplatin, chlormethine, chlorambucil, melphalan, cyclophosphamide, ifosfamide, estramustine, carmustine, lomustine, fotemustine, streptozocin, busulfan, pipobroman, procarbazine, dacarabazine, thiotepa and temozolomide.

22. The method of claim 18, wherein step i) comprises quantifying the number of copy number variations per genome by sequencing, comparative genomic hybridization array or single nucleotide polymorphism array.

23. The method of claim 18, wherein said breast cancer is basal-like, luminal, or HER2-overexpressing breast carcinoma.

24. The method of claim 18, wherein step iii) comprises administering a PARP inhibitor and/or an alkylating agent to said patient if at least 11 large-scale transitions have been detected in step i) or a germline or somatic DNA mutation in at least one of the HR pathway genes has been detected in step ii).

25. A method for treating cancer in a patient in need thereof, the method comprising:
   i) quantifying the number of large-scale transitions in the genomic DNA of a tumor sample obtained from said patient, a large-scale transition being a somatic copy number transition along the length of a chromosome between two genomic regions each at least 10 megabases in length after filtering out transitions between genomic regions shorter than 3 megabases in length;
   ii) sequencing genomic DNA of said tumor sample to determine the presence of germline or somatic DNA mutations in BRCA1, BRCA2 and at least one other gene of the homologous recombination (HR) pathway selected from partner and localizer of BRCA2 (PALB2/FANCN), BRCA1-interacting protein 1 (BRIP1/FANCJ), BRCA1-associated RING domain protein 1 gene (BARD1), Rad51 recombinase (RAD51) and RAD51 paralogs which are RAD51B, RAD51C, RAD51D, X-Ray Repair Cross Complementing 2 (XRCC2) and X-Ray Repair Cross Complementing 3 (XRCC3); and
   iii) administering a PARP inhibitor and/or an alkylating agent to said patient having a tumor sample comprising a cancer cell having at least 11 large-scale transitions per genome or a germline or somatic DNA mutation in at least one of the HR pathway genes in step ii).

26. A method for treating cancer in a patient in need thereof, the method comprising:
   i) quantifying the number of large-scale transitions in the genomic DNA of a tumor sample obtained from said patient, a large-scale transition being a somatic copy number transition along the length of a chromosome between two genomic regions each at least 10 megabases in length after filtering out transitions between genomic regions shorter than 3 megabases in length;
   ii) sequencing genomic DNA of said tumor sample to determine the presence of germline or somatic DNA mutations in BRCA1, BRCA2 and at least one other gene of the HR pathway selected from PALB2/FANCN, BRIP1/FANCJ, BARD1, RAD51 and RAD51 paralogs which are RAD51B, RAD51C, RAD51D, XRCC2, XRCC3; and
   iii) administering a PARP inhibitor and/or an alkylating agent to said patient having a tumor sample identified as comprising a cancer cell having at least 11 large-scale transitions per genome or a germline or somatic DNA mutation in at least one of the HR pathway genes in step ii).

27. A method for treating cancer in a patient in need thereof, the method comprising:
  i) quantifying the number of large-scale transitions in the genomic DNA of a tumor sample obtained from said patient, a large-scale transition being a somatic copy number transition along the length of a chromosome between two genomic regions each at least 10 megabases in length after filtering out transitions between genomic regions shorter than 3 megabases in length;
  ii) sequencing genomic DNA of said tumor sample to determine the presence of germline or somatic DNA mutations in BRCA1, BRCA2 and at least one other gene in of the HR pathway selected from PALB2/FANCN, BRIP1/FANCJ, BARD1, RAD51 and RAD51 paralogs which are RAD51B, RAD51C, RAD51D, XRCC2, XRCC3; and
  iii) administering a PARP inhibitor and/or an alkylating agent to said patient having at least 11 large-scale transitions detected in step i) or a germline or somatic DNA mutation in at least one of the HR pathway genes has been detected in step ii).

28. The method of claim 25, wherein the cancer is selected from breast cancer, ovary cancer, pancreas cancer, head and neck carcinoma and melanoma.

29. The method of claim 26, wherein the cancer is selected from breast cancer, ovary cancer, pancreas cancer, head and neck carcinoma and melanoma.

30. The method of claim 27, wherein the cancer is selected from breast cancer, ovary cancer, pancreas cancer, head and neck carcinoma and melanoma.

31. The method of claim 25, wherein the cancer is breast cancer.

32. The method of claim 26, wherein the cancer is breast cancer.

33. The method of claim 27, wherein the cancer is breast cancer.

34. The method of claim 25, wherein the PARP inhibitor and/or alkylating agent is selected from the group consisting of olaparib, rucaparib, CEP 9722, MK 4827, BMN-673, 3-aminobenzamide, platinium complexes such as cisplatin, carboplatin and oxaliplatin, chlormethine, chlorambucil, melphalan, cyclophosphamide, ifosfamide, estramustine, carmustine, lomustine, fotemustine, streptozocin, busulfan, pipobroman, procarbazine, dacarabazine, thiotepa and temozolomide.

35. The method of claim 26, wherein the PARP inhibitor and/or alkylating agent is selected from the group consisting of olaparib, rucaparib, CEP 9722, MK 4827, BMN-673, 3-aminobenzamide, platinium complexes such as cisplatin, carboplatin and oxaliplatin, chlormethine, chlorambucil, melphalan, cyclophosphamide, ifosfamide, estramustine, carmustine, lomustine, fotemustine, streptozocin, busulfan, pipobroman, procarbazine, dacarabazine, thiotepa and temozolomide.

36. The method of claim 27, wherein the PARP inhibitor and/or alkylating agent is selected from the group consisting of olaparib, rucaparib, CEP 9722, MK 4827, BMN-673, 3-aminobenzamide, platinium complexes such as cisplatin, carboplatin and oxaliplatin, chlormethine, chlorambucil, melphalan, cyclophosphamide, ifosfamide, estramustine, carmustine, lomustine, fotemustine, streptozocin, busulfan, pipobroman, procarbazine, dacarabazine, thiotepa and temozolomide.

37. The method of claim 26, wherein step i) comprises quantifying the number of copy number variations per genome by sequencing, comparative genomic hybridization array or single nucleotide polymorphism array.

38. The method of claim 27, wherein step i) comprises quantifying the number of copy number variations per genome by sequencing, comparative genomic hybridization array or single nucleotide polymorphism array.

39. The method of claim 31, wherein said breast cancer is basal-like, luminal, or HER2-overexpressing breast carcinoma.

40. The method of claim 32, wherein said breast cancer is basal-like, luminal, or HER2-overexpressing breast carcinoma.

41. The method of claim 33, wherein said breast cancer is basal-like, luminal, or HER2-overexpressing breast carcinoma.

* * * * *